United States Patent [19]

Chen

[11] Patent Number: 5,962,479
[45] Date of Patent: Oct. 5, 1999

[54] CORTICOTROPIN RELEASING FACTOR ANTAGONISTS

[75] Inventor: Yuhpyng Liang Chen, Waterford, Conn.

[73] Assignee: Pfizer Inc., New York, N.Y.

[21] Appl. No.: 08/765,110

[22] PCT Filed: Jun. 6, 1995

[86] PCT No.: PCT/IB95/00439

§ 371 Date: Dec. 6, 1996

§ 102(e) Date: Dec. 6, 1996

[87] PCT Pub. No.: WO95/33750

PCT Pub. Date: Dec. 14, 1995

Related U.S. Application Data

[63] Continuation-in-part of application No. 08/255,514, Jun. 8, 1994, abandoned.

[51] Int. Cl.$^6$ .......................... A61K 31/44; A61K 31/47; A61K 31/505; A61K 31/495; C07D 213/62
[52] U.S. Cl. .......................... 514/348; 514/255; 514/256; 514/269; 514/272; 514/274; 514/275; 514/312; 514/314; 514/332; 514/333; 514/335; 514/336; 514/337; 514/338; 514/339; 514/340; 514/341; 514/342; 514/343; 514/344; 514/345; 514/349; 514/350; 514/351; 514/352; 514/354; 514/355; 514/356; 514/357; 546/153; 546/155; 546/156; 546/157; 546/159; 546/167; 546/255; 546/256; 546/261; 546/262; 546/263; 546/264; 546/265; 546/266; 546/267; 546/278.4; 546/296; 546/297; 546/307; 544/295; 544/296; 544/397; 544/300; 544/310; 544/316; 544/317; 544/319; 544/320; 544/326; 544/328; 544/329; 544/331; 544/333; 544/405
[58] Field of Search .......................... 544/295, 296, 544/297, 300, 310, 316, 317, 319, 320, 326, 328, 329, 331, 333, 405; 514/255, 256, 269, 272, 274, 275, 312, 314, 332, 333, 335, 336, 337, 339, 338, 340, 341, 342, 343, 344, 345, 348, 349, 350, 351, 352, 354, 355, 356, 357; 546/153, 155, 156, 157, 159, 167, 255, 256, 261, 262, 263, 264, 265, 266, 267, 278.4, 296, 297, 307

[56] References Cited

U.S. PATENT DOCUMENTS

| 4,605,642 | 8/1986 | Rivier et al. | 514/12 |
| 4,839,353 | 6/1989 | Hosoi et al. | 514/212 |
| 5,063,245 | 11/1991 | Abren et al. | 514/404 |
| 5,691,364 | 11/1997 | Buckman et al. | 514/341 |

FOREIGN PATENT DOCUMENTS

| 0475411 | 3/1992 | European Pat. Off. |
| 0482804 | 4/1992 | European Pat. Off. |
| 3145287 | 5/1983 | Germany |
| WO 95/10506 | 4/1995 | WIPO |

OTHER PUBLICATIONS

Cossey et al., Pyridines and Pyridinium Salts from Cyanoacetamides, Australian Journal of Chemistry, vol. 29, No. 5, pp. 1039–1050, May 1976.

De Souza, Corticotropin–Releasing Factor Receptors: Physiology, Pharmacology, Biochemistry and Role in Central Nervous System and Immune Disorders, Psychoneuroendocrinology, vol. 20, No. 8, pp. 789–819, 1995.

Fackelmann, K.A., and Raloff, J., Psychological Stress Linked to Cancer, Science News (Sep. 25, 1993) vol. 144, p. 196.

Lyons, M.K., et al., Corticotropin releasing factor antagonist reduces ischemic hippocampal neuronal injury, Brain Research, vol. 545 Issue 1–2, pp. 339–342 (1991).

Stratakis, C.A., and Chrousos G.P., Hypothalamic Hormones GnRH, TRH, GHRH, SRIF, CRH, and Dopamine, Endocrinology: Basic and Clinical Principles, pp. 185–209, (Humana Press, Tofowa, NJ, 1997).

(List continued on next page.)

Primary Examiner—Mukund J. Shah
Assistant Examiner—Brenda Coleman
Attorney, Agent, or Firm—Peter C. Richardson; Paul H. Ginsburg; Kristina L. Konstas

[57] ABSTRACT

Corticotropin-releasing factor (CRF) antagonists having formulae (I), (II) or (III) wherein the dashed lines, A, B, Y, Z, G, $R_3$, $R_4$, $R_5$, $R_6$, $R_{16}$ and $R_{17}$ are as defined in the description, and processes for preparing them. These compounds and their pharmaceutically acceptable salts are useful in the treatment of CNS and stress-related disorders.

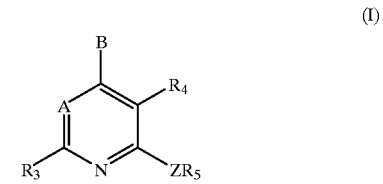

(I)

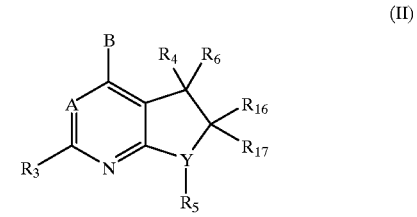

(II)

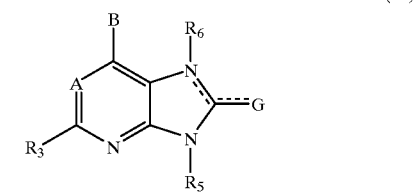

(III)

16 Claims, No Drawings

OTHER PUBLICATIONS

Strijbos, P.J.L.M., et al., Brain Res. 656, pp. 405–408 (1991).

Chalmers D.T., et al., Corticotrophin–releasing factors molecular biology to drug design, Trends in Pharmacological Sciences, vol. 17, pp. 166–172 (1996).

Owens et al. *Pharm. Rev.,* vol. 43 (1991), pp. 425–473.

*Chem. Abstr.,* vol. 72 (1970), Abstract No. 11080v.

Robbins, et al., *Can. J. Chem.,* vol. 55 (1977) pp. 1251–1259.

CORTICOTROPIN RELEASING FACTOR ANTAGONISTS

This application is the National Stage of international Application No. PCT/IB95/00439, filed Jun. 6, 1995, and is a continuation-in-part of and claims the benefit of U.S. application Ser. No. 08/255,514, filed Jun. 8, 1994, now abandoned.

BACKGROUND OF THE INVENTION

This invention relates to pyridines, pyrimidines, purinones, pyrrolopyrimidinones and pyrrolopyridinones, processes for preparing them, pharmaceutical compositions containing them, and methods of using them to treat certain central nervous system (CNS) and other disorders.

CRF antagonists are mentioned in U.S. Pat. Nos. 4,605,642 and 5,063,245 referring to peptides and pyrazolinones, respectively. The importance of CRF antagonists is set out in the literature, e.g., as discussed in U.S. Pat. No. 5,063,245, which is incorporated herein by reference. A recent outline of the different activities possessed by CRF antagonists is found in M. J. Owens et al., *Pharm. Rev.*, Vol. 43, pages 425 to 473 (1991), also incorporated herein by reference. Based on the research described in these two and other references, CRF antagonists are effective in the treatment of a wide range of stress-related illnesses, such as depression, anxiety, headache, irritable bowel syndrome, inflammatory diseases, immune suppression, Alzheimer's disease, gastrointestinal diseases, anorexia nervosa, hemorrhagic stress, drug and alcohol withdrawal symptoms, drug addiction, infertility, head trauma, stroke, and stress-induced infections in humans and animals.

SUMMARY OF THE INVENTION

The present invention relates to a compound of the formula

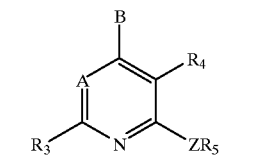

I

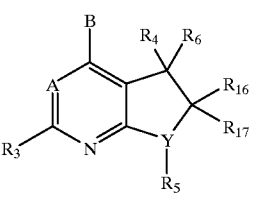

II or

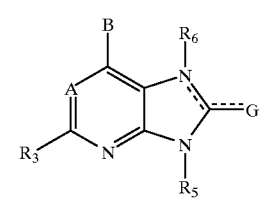

III or a pharmaceutically acceptable salt thereof, wherein the dashed lines represent optional double bonds;

A is —$CR_7$ or N;

B is —$NR_1R_2$, —$CR_1R_2R_{11}$, —$C(=CR_2R_{12})R_1$, —$NHCHR_1R_2$, —$OCHR_1R_2$, —$SCHR_1R_2$, —$CHR_2OR_{12}$, —$CHR_2SR_{12}$, —$C(S)R_2$ or —$C(O)R_2$;

G is oxygen, sulfur, NH, $NCH_3$, hydrogen, methoxy, ethoxy, trifluoromethoxy, methyl, ethyl, thiomethoxy, $NH_2$, $NHCH_3$, $N(CH_3)_2$ or trifluoromethyl;

Y is —CH or N;

Z is NH, O, S, —N($C_1$–$C_2$ alkyl) or —$C(R_{13}R_{14})$, wherein $R_{13}$ and $R_{14}$ are each, independently, hydrogen, trifluoromethyl or methyl, or one of $R_{13}$ and $R_{14}$ is cyano and the other is hydrogen or methyl;

$R_1$ is $C_1$–$C_6$ alkyl which may optionally be substituted with one or two substituents $R_8$ independently selected from the group consisting of hydroxy, fluoro, chloro, bromo, iodo, $CF_3$, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$ alkyl), —N($C_1$–$C_4$alkyl)CO($C_1$–$C_4$ alkyl), —NHCO($C_1$–$C_4$ alkyl), —COO($C_1$–$C_4$ alkyl), —CONH($C_1$–$C_4$ alkyl), —CON($C_1$–$C_4$ alkyl)($C_1$–$C_2$ alkyl), CN, $NO_2$, —SO($C_1$–$C_4$ alkyl) and —$SO_2$($C_1$–$C_4$ alkyl), and wherein said $C_1$–$C_6$ alkyl and the ($C_1$–$C_4$)alkyl moieties in the foregoing $R_1$ groups may optionally contain one carbon-carbon double or triple bond;

$R_2$ is $C_1$–$C_{12}$ alkyl, aryl or —($C_1$–$C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or —($C_1$–$C_6$ alkylene)cycloalkyl, wherein one or two of the ring carbons of said cycloalkyl having at least 4 ring members and the cycloalkyl moiety of said —($C_1$–$C_6$ alkylene)cycloalkyl having at least 4 ring members may optionally be replaced by an oxygen or sulfur atom or by N—$R_9$ wherein $R_9$ is hydrogen or $C_1$–$C_4$ alkyl; and wherein each of the foregoing $R_2$ groups may optionally be substituted with from one to three substituents independently selected from chloro, fluoro and $C_1$–$C_4$ alkyl, or with one substituent selected from bromo, iodo, $C_1$–$C_6$ alkoxy, —O—CO—($C_1$–$C_6$ alkyl), —O—CO—N($C_1$–$C_4$ alkyl)($C_1$–$C_2$ alkyl), —S($C_1$–$C_6$ alkyl), CN, $NO_2$, —SO($C_1$–$C_4$ alkyl), and —$SO_2$($C_1$–$C_4$ alkyl), and wherein said $C_1$–$C_{12}$ alkyl and the $C_1$–$C_4$ alkylene moiety of said —($C_1$–$C_4$ alkylene)aryl may optionally contain one carbon-carbon double or triple bond;

or —$NR_1R_2$ or —$CR_1R_2R_{11}$ may form a saturated 5- to 8-membered carbocyclic ring which may optionally contain one or two carbon-carbon double bonds and in which one or two of the ring carbons may optionally be replaced by an oxygen or sulfur atom;

$R_3$ is methyl, ethyl, fluoro, chloro, bromo, iodo, cyano, methoxy, $OCF_3$, methylthio, methylsulfonyl, $CH_2OH$, or $CH_2OCH_3$;

$R_4$ is hydrogen, $C_1$–$C_4$ alkyl, fluoro, chloro, bromo, iodo, $C_1$–$C_4$ alkoxy, trifluoromethoxy, —$CH_2OCH_3$, —$CH_2OCH_2CH_3$, —$CH_2CH_2OCH_3$, —$CH_2OF_3$, $CF_3$, amino, nitro, —NH($C_1$–$C_4$ alkyl), —N($CH_3$)$_2$, —$NHCOCH_3$, —$NHCONHCH_3$, —$SO_n$($C_1$–$C_4$ alkyl) wherein n is 0, 1 or 2, cyano, hydroxy, —CO($C_1$–$C_4$ alkyl), —CHO, cyano or —COO($C_1$–$C_4$ alkyl) wherein said $C_1$–$C_4$ alkyl may optionally contain one double or triple bond and may optionally be substituted with one substituent selected from hydroxy, amino, —NHCOCH$_3$, —NH(C$_1$–C$_2$ alkyl), —N(C$_1$–C$_2$ alkyl)$_2$, —COO(C$_1$–C$_4$ alkyl), —CO(C$_1$–C$_4$ alkyl), C$_1$–C$_3$ alkoxy, C$_1$–C$_3$ thioalkyl, fluoro, chloro, cyano and nitro;

R$_5$ is phenyl, naphthyl, thienyl, benzothienyl, pyridyl, quinolyl, pyrazinyl, pyrimidyl, furanyl, benzofuranyl, benzothiazolyl, or indolyl, wherein each of the above groups R$_5$ is substituted with from one to three substituents independently selected from fluoro, chloro, C$_1$–C$_6$ alkyl, and C$_1$–C$_6$ alkoxy, or with one substituent selected from hydroxy, iodo, bromo, formyl, cyano, nitro, trifluoromethyl, amino, —(C$_1$–C$_6$ alkyl)O(C$_1$–C$_6$)alkyl, —NHCH$_3$, —N(CH$_3$)$_2$, —COOH, —COO(C$_1$–C$_4$ alkyl), —CO(C$_1$–C$_4$ alkyl), —SO$_2$NH(C$_1$–C$_4$ alkyl), —SO$_2$N(C$_1$–C$_4$ alkyl)(C$_1$–C$_2$ alkyl), —SO$_2$NH$_2$, —NHSO$_2$(C$_1$–C$_4$ alkyl), —S(C$_1$–C$_6$ alkyl) and —SO$_2$(C$_1$–C$_6$ alkyl), and wherein the C$_1$–C$_4$ alkyl and C$_1$–C$_6$ alkyl moieties of the foregoing R$_5$ groups may optionally be substituted with one or two fluoro groups or with one substituent selected from hydroxy, amino, methylamino, dimethylamino and acetyl;

R$_6$ is hydrogen or C$_1$–C$_6$ alkyl, wherein said C$_1$–C$_6$ alkyl may optionally be substituted with one hydroxy, methoxy, ethoxy or fluoro group;

R$_7$ is hydrogen, methyl, fluoro, chloro, bromo, iodo, cyano, hydroxy, —O(C$_1$–C$_4$ alkyl), —C(O)(C$_1$–C$_4$ alkyl), —C(O)O(C$_1$–C$_4$ alkyl), —OCF$_3$, CF$_3$, —CH$_2$OH, —CH$_2$OCH$_3$ or —CH$_2$OCH$_2$CH$_3$;

R$_{11}$ is hydrogen, hydroxy, fluoro, or methoxy;

R$_{12}$ is hydrogen or C$_1$–C$_4$ alkyl; and

R$_{16}$ and R$_{17}$ are each, independently, hydrogen, hydroxy, methyl, ethyl, methoxy, or ethoxy, except that R$_{16}$ and R$_{17}$ are not both methoxy or ethoxy;

or R$_{16}$ and R$_{17}$ together form an oxo (=O) group;

with the proviso that when G is oxygen, sulfur, NH or NCH$_3$, it is double bonded to the five membered ring of structure III, and with the further proviso that R$_6$ is absent when the nitrogen to which it is attached is double bonded to an adjacent ring carbon atom.

More specific embodiments of this invention include compounds of the formula I, II or III wherein: (a) B is —NR$_1$R$_2$, —NHCHR$_1$R$_2$, —SCHR$_1$R$_2$ or —OCHR$_1$R$_2$; R$_1$ is C$_1$–C$_6$ alkyl, which may optionally be substituted with one hydroxy, fluoro, CF$_3$, or C$_1$–C$_2$ alkoxy group and may optionally contain one double or triple bond; and R$_2$ is benzyl or C$_1$–C$_6$ alkyl which may optionally contain one carbon-carbon double or triple bond, wherein said C$_1$–C$_6$ alkyl or the phenyl moiety of said benzyl may optionally be substituted with fluoro, CF$_3$, C$_1$–C$_2$ alkyl, or C$_1$–C$_2$ alkoxy; or (b) B is —CR$_1$R$_2$R$_{11}$ wherein R$_1$ is C$_1$–C$_6$ alkyl which may optionally be substituted with one C$_1$–C$_2$ alkoxy, CF$_3$, fluoro or hydroxy group; R$_2$ is benzyl or C$_1$–C$_6$ alkyl wherein said C$_1$–C$_6$ alkyl or the phenyl moiety of said benzyl may optionally be substituted with one C$_1$–C$_2$ alkyl, CF$_3$, C$_1$–C$_2$ alkoxy, fluoro, chloro or bromo group; and R$_{11}$ is hydrogen or fluoro.

Other more specific embodiments of this invention include compounds of the formula I, II or III wherein R$_1$ is C$_1$–C$_6$ alkyl which may optionally be substituted by fluoro, CF$_3$, hydroxy, C$_1$–C$_2$ alkyl or C$_1$–C$_2$ alkoxy and may optionally contain one carbon-carbon double or triple bond, and R$_2$ is C$_1$–C$_4$ alkyl which may optionally be substituted with fluoro, chloro, CF$_3$, C$_1$–C$_4$ alkyl or C$_1$–C$_4$ alkoxy.

Other more specific embodiments of this invention include compounds of the formula I, II or III wherein R$_3$ is methyl, chloro, or methoxy, R$_4$ is methyl, —CH$_2$OH, cyano, trifluoromethoxy, methoxy, trifluoromethyl, chloro, —COOCH$_3$, —CH$_2$OCH$_3$, —CH$_2$Cl, —CH$_2$F, amino or nitro; R$_6$ is hydrogen, methyl or ethyl and R$_5$ is phenyl or pyridyl wherein said phenyl or pyridyl is substituted by two or three substituents independently selected from fluoro, chloro, bromo, iodo, C$_1$–C$_4$ alkoxy, trifluoromethyl, C$_1$–C$_6$ alkyl which may optionally be substituted with one hydroxy, C$_1$–C$_2$ alkoxy or fluoro group and may optionally contain one carbon-carbon double or triple bond, -(C$_1$–C$_4$ alkylene)O(C$_1$–C$_2$ alkyl), C$_1$–C$_3$ hydroxyalkyl, hydroxy, formyl, —COO(C$_1$–C$_2$ alkyl), —(C$_1$–C$_2$ alkylene)amino, and —(C(O)(C$_1$–C$_4$ alkyl).

Examples of preferred compounds of this invention are:

4-(1-ethyl-propoxy)-2,5-dimethyl-6-(2,4,6-trimethyl-benzyl)-pyrimidine;

2-(4-bromo-2,6-dimethyl-phenoxy)4-(1-ethyl-propoxy)-3,6-dimethyl-pyridine;

2-(4-ethyl-2,6-dimethyl-phenoxy)4-(1-ethyl-propoxy)-3,6-dimethyl-pyridine;

3-ethyl-4-(1-ethyl-propoxy)-6-methyl-2-(2,4,6-trimethyl-phenoxy)-pyridine;

2-(2,6-dimethyl-4-propyl-phenoxy)4-(1-ethyl-propoxy)-3,6-dimethyl-pyridine;

4-(1-ethyl-propoxy)-2-(4-methoxy-2,6-dimethyl-phenoxy)-3,6-dimethyl-pyridine;

2-(4-ethoxy-2,6-dimethyl-phenoxy)4-(1-ethyl-propoxy)-3,6-dimethyl-pyridine;

2-(4-chloro-2,6-dimethyl-phenoxy)4-(1-ethyl-propoxy)-3,6-dimethyl-pyridine;

4(1-methoxymethyl-propoxy)-3,6-dimethyl-2-(2,4,6-trimethyl-phenoxy)-pyridine;

[3,6-dimethyl-2-(2,4,6-trimethyl-phenoxy)-pyridin-4-yl]-diethyl-amine;

[3,6-dimethyl-2-(2,4,6-trimethyl-phenoxy)-pyridin-4-yl]-ethyl-propyl-amine;

[2,5-dimethyl-6-(2,4,6-trimethyl-phenoxy)-pyrimidin-4-yl](1-ethyl-propyl)-amine;

butyl-[3,6-dimethyl-2-(2,4,6-trimethyl-phenoxy)-pyridin-4-yl]-ethyl-amine;

4-(1-ethyl-propoxy)-3,6-dimethyl-2-(2,4,6-trimethyl-phenylsulfanyl)-pyridine;

butyl-[2-(4-chloro-2,6-dimethyl-phenoxy)-3,6-dimethyl-pyridin4-yl] -ethyl-amine;

4-(1-ethyl-propylamino)-6-methyl-2-(2,4,6-trimethyl-phenoxy)-nicotinic acid methyl ester;

[3,6-dimethyl-[2-(2,4,6-trimethyl-phenylsulfanyl)-pyridin-4-yl]-ethyl-propyl-amine;

4-(1-ethyl-propylamino)-6-methyl-2-(2 ,4,6-trimethyl-phenoxy)-pyridin-3-yl]-methanol;

[2-(4-chloro-2,6-dimethyl-phenoxy)-3,6-dimethyl-pyridin4-yl]-ethyl-propyi-amine;

1-(ethyl-propyl)-[6-methyl-3-nitro-2-(2,4,6-trimethyl-phenoxy)-pyridin-4-yl]-amine;

N4-(1-ethyl-propyl)-6-methyl-3-nitro—N2-(2,4,6-trimethyl-phenyl)-pyridine-2,4-diamine;

N4-(1-ethyl-propyl)-6-methyl-2-(2,4,6-trimethyl-phenoxy)-pyridine-3,4-diamine;

3,6-dimethyl-2-(2,4,6-trimethyl-phenoxy)-pyridin-4-yl]-ethyl-(2,2,2-trifluoro-ethyl)-amine;

N4-(1-ethyl-propyl)-6-methyl—N2-(2,4,6-trimethyl-phenyl)-pyridin2,3,4-triamine;

[3-chloromethyl-methyl-2-(2,4,6-trimethyl-phenoxy) pyridin-4yl]-(1-ethyl-propyl)-amine;

[3,6-dimethyl-2-(2,4,6-trimethyl-phenoxy)-pyridin-4-yl]-(1-ethyl-propyl)-amine;

(1-ethyl-propyl)-[2-methyl-5-nitro-6-(2,4,6-trimethyl-pyridin-3-yloxy)-pyrimidin yl]-amine;

(1-ethyl-propyl)-[3-methoxymethyl-methyl-2-(2,4,6-trimethyl-phenoxy)-pyrdin-4-yl]-amine;

(N-(1-ethyl-propyl)-2-methyl-5-nitro—N '-(2,4,6-trimethyl-pyrimidin-yl)-pyrimidine4,6-diamine;

[2-(4-chloro-2,6-dimethyl-phenoxy)-3,6-dimethyl-pyridin-4-yl]-diethyl-amine;

4-(1-ethyl-propoxy)-3,6-dimethyl-2-(2,4,6-trimethylphenoxy)-pyridine;

butyl-[2,5-dimethyl-7-(2,4,6-trimethyl phenyl)-6,7-dihydro-5H-pyrrolo[2,3-d]pyrimidin-4-yl]-ethyl-amine;

4-(butyl-ethylamino)-2,5-dimethyl-7-(2,4,6-trimethylphenyl)-5,7-dihydro-pyrrolo[2,3-d]pyrimidin-6-one;

4-(1-ethylpropoxy)-2,5-dimethyl-6-(2 ,4,6-trimethylphenoxy)-pyrimidine;

N-butyl—N-ethyl-2,5-dimethyl—N'-(2,4,6-trimethylphenyl)-pyrimidine-4,6-diamine;

(1-ethyl-propyl)-[5-methyl-3-(2,4,6trimethyl-phenyl)-3H-imidazo[4,5b]pyridin-7-yl]-amine;

[2,5-dimethyl-3-(2,4,6-trimethyl-phenyl)-3H-imidazo [4,5-b]pyridin-7-yl]-(1-ethyl-propyl)-amine;

N4-(1-ethyl-propyl)-6,N3-dimethyl-2-(2,4,6-trimethyl-phenoxy)-pyridine-3,4-diamine;

N4-(1-ethyl-propyl)-6,N3, N3-trimethyl-2-(2,4,6-trimethyl-phenoxy)-pyridine-3,4-diamine;

6(1-ethyl-propoxy)-2-methyl—N4-(2,4,6-trimethyl-phenyl)-pyrimidine4,5-diamine;

[4-(1-ethyl-propoxy)-3,6-dimethyl-pyridin-2-yl]-(2,4,6-trimethylphenyl)-amine; and 6-(ethyl-propyl-amino)-2,7-dimethyl-9-(2,4,6-trim ethyl phenyl)-7 ,9-dihydro-purin-8-one.

The invention also relates to a pharmaceutical composition for the treatment of (a) a disorder the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer; irritable bowel syndrome, Crohn's disease; spastic colon; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; and hypoglycemia in a mammal, including a human, comprising an amount of a compound of the formula I, II or III, or a pharmaceutically acceptable salt thereof, that is effective in the treatment of such disorder, and a pharmaceutically acceptable carrier.

The invention further includes a method for the treatment of (a) a disorder the treatment of which can be effected or facilitated by antagonizing CRF, including but not limited to disorders induced or facilitator by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer; irritable bowel syndrome; Crohn's disease; spastic colon; human immunodeficiency Virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e, cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; and hypoglycemia in a mammal, including a human, comprising administering to a subject in need of said treatment an amount of a compound of the formula I, II or III or a pharmaceutically acceptable salt thereof, that is effective in treating such disorder.

The invention further includes intermediate compounds of formula

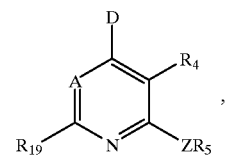

IV

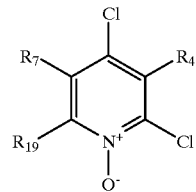

XI and

-continued

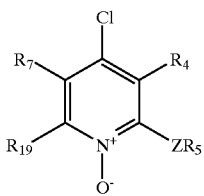

X wherein $R_4$ and $R_7$ are defined as they are for formula I above; D is chloro, hydroxy or cyano; $R_{19}$ is methyl or ethyl; $R_5$ is phenyl or pyridyl and $R_5$ is substituted by two or three substituents independently selected from $C_1$–$C_4$ alkyl, chloro and bromo, except that no more than one such substituent can be bromo; A is N, CH or CCH$_3$; and Z is O, NH, N(CH$_3$), S or CH$_2$, with the proviso that when A is CH or CCH$_3$, then Z must be O or S.

More specific embodiments of this invention relate to compounds of the formula X or XI wherein $R_7$ is hydrogen or methyl.

This invention further include intermediate compounds of formula

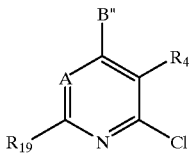

XII wherein $R_{19}$ is methyl or ethyl; A is N, CH or CCH$_3$; and wherein when A is N, then B" and $R_4$ are defined, respectively, as B and $R_4$ are defined for formula I, and when A is CH or CH$_3$, then B" is —NR$_1$R$_2$, —NHR$_1$R$_2$, —OCHR$_1$R$_2$ or cyano and $R_4$ is an electron deficient group such as NO$_2$, —COO(C$_1$–C$_4$ alkyl), —C(═O)CH$_3$, —COOH or CN.

A more specific embodiment of this invention relates to compounds of the formula XII wherein B" is —NR$_1$R$_2$ or —NHCHR$_1$R$_2$ and A is CH or CH$_3$.

This invention also relates to a process for preparing a compound of the formula I,

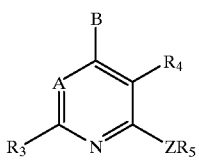

I or a pharmaceutically acceptable salt thereof, wherein

A is —CR$_7$ or N;

B is —NR$_1$R$_2$, —NHCHR$_1$R$_2$, —OCHR$_1$R$_2$ or —SCHR$_1$R$_2$;

Z is NH, O, S, —N(C$_1$–C$_2$ alkyl) or —C(R$_{13}$R$_{14}$), wherein R$_{13}$ and R$_{14}$ are each, independently, hydrogen, trifluoromethyl or methyl, or one of R$_{13}$ and R$_{14}$ is cyano and the other is hydrogen or methyl;

R$_1$ is C$_1$–C$_6$ alkyl which may optionally be substituted with one or two substituents R$_8$ independently selected from the group consisting of hydroxy, fluoro, chloro, bromo, iodo, CF$_3$ and C$_1$–C$_4$ alkoxy, and wherein said C$_1$–C$_6$ alkyl and the (C$_1$–C$_4$)alkyl moiety of said C$_1$–C$_4$ alkoxy may optionally contain one carbon-carbon double or triple bond;

R$_2$ is C$_1$–C$_{12}$ alkyl, aryl or —(C$_1$–C$_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or —(C$_1$–C$_6$ alkylene) cycloalkyl, wherein one or two of the ring carbons of said cycloalkyl having at least 4 ring members and the cycloalkyl moiety of said —(C$_1$–C$_6$ alkylene) cycloalkyl having at least 4 ring members may optionally be replaced by an oxygen or sulfur atom or by N—R$_9$ wherein R$_9$ is hydrogen or C$_1$–C$_4$ alkyl; and wherein each of the foregoing R$_2$ groups may optionally be substituted with from one to three substituents independently selected from chloro, fluoro and C$_1$–C$_4$ alkyl, or with one substituent selected from bromo, iodo, C$_1$–C$_6$ alkoxy, —O—CO—(C$_1$–C$_6$ alkyl), —O—CO—N(C$_1$–C$_4$ alkyl)(C$_1$–C$_2$ alkyl), —S(C$_1$–C$_6$ alkyl), CN, NO$_2$, —SO(C$_1$–C$_4$ alkyl), and —SO$_2$ (C$_1$–C$_4$ alkyl), and wherein said C$_1$–C$_{12}$ alkyl and the C$_1$–C$_4$ alkylene moiety of said —(C$_1$–C$_4$ alkylene)aryl may optionally contain one carbon-carbon double or triple bond;

or —NR$_1$ R$_2$ may form a saturated 5- to 8-membered carbocyclic ring which may optionally contain one or two carbon—carbon double bonds and in which one or two of the ring carbons may optionally be replaced by an oxygen or sulfur atom;

R$_3$ is methyl or ethyl;

R$_4$ is hydrogen, C$_1$–C$_4$ alkyl, fluoro, chloro, bromo, iodo, C$_1$–C$_4$ alkoxy, trifluoromethoxy, —CH$_2$OCH$_3$, —CH$_2$OCH$_2$CH$_3$, —CH$_2$CH$_2$OCH$_3$, —CH$_2$OF$_3$,CF$_3$, amino, nitro, —NH(C$_1$–C$_4$ alkyl), —N(CH$_3$)$_2$, —NHCOCH$_3$, —NHCONHCH$_3$, —SO$_n$(C$_1$–C$_4$ alkyl) wherein n is 0, 1 or 2, cyano, hydroxy, —CO(C$_1$–C$_4$ alkyl), —CHO, cyano or —COO(C$_1$–C$_4$ alkyl) wherein said C$_1$–C$_4$ alkyl may optionally contain one double or triple bond and may optionally be substituted with one substituent selected from hydroxy, amino, —NHCOCH$_3$, —NH(C$_1$–C$_2$ alkyl), —N(C$_1$–C$_2$ alkyl) $_2$, —COO(C$_1$–C$_4$ elkyl), —CO(C$_1$–C$_4$ alkyl), C$_1$–C$_3$ alkoxy, C$_1$–C$_3$ thioalkyl, fluoro, chloro, cyano and nitro;

R$_5$ is phenyl or pyridyl, and R$_5$ is substituted with from one to three substituents independently selected from fluoro, chloro, C$_1$–C$_8$ alkyl, and C$_1$–C$_6$ alkoxy, or with one substituent selected from hydroxy, iodo, bromo, formyl, cyano, nitro, trifluoromethyl, amino, —(C$_1$–C$_6$ alkyl)O(C$_1$–C$_6$)alkyl, —NHCH$_3$, —N(CH$_3$)$_2$, —COOH, —COO(C$_1$–C$_4$ alkyl), —CO(C$_1$–C$_4$ alkyl), —SO$_2$NH(C$_1$–C$_4$ alkyl), —SO$_2$N(C$_1$–C$_4$ alkyl)(C$_1$–C$_2$ alkyl), —SO$_2$NH$_2$, —NHSO$_2$(C$_1$–C$_4$ alkyl), —S(C$_1$–C$_6$ alkyl) and —SO$_2$(C$_1$–C$_6$ alkyl), and wherein the C$_1$–C$_4$ alkyl and C$_1$–C$_6$ alkyl moieties of the foregoing R$_5$ groups may optionally be substituted with one or two fluoro groups or with one substituent selected from hydroxy, amino, methylamino, dimethylamino and acetyl; and R$_7$ is hydrogen or methyl;

or a pharmaceutically acceptable salt of such compound;

comprising reacting a compound of the formula

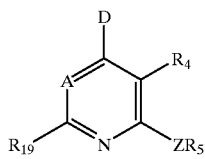

IV wherein $R_{19}$ is methyl or ethyl, D is chloro and A, Z, $R_4$ and $R_5$ are defined as above, with a compound of the formula BH, wherein B is defined as above, in the presence of a base; and then optionally converting the compound of formula I formed in such reaction into a pharmaceutically acceptable salt.

This invention also relates to a process for preparing a compound of the formula

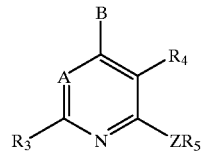

I or a pharmaceutically acceptable salt thereof, wherein

A is —CR7 or N;

B is —$NR_1R_2$, —$CR_1R_2R_{11}$, —$C(=CR_2R_{12})R_1$, —$NHCHR_1R_2$, —$OCHR_1R_2$, —$SCHR_1R_2$, —$CHR_2OR_{12}$, —$CHR_2SR_{12}$, —$C(S)R_2$ or —$C(O)R_2$;

Z is NH, O, S, —$N(C_1-C_2$ alkyl) or —$C(R_{13}R_{14})$, wherein $R_{13}$ and $R_{14}$ are each, independently, hydrogen, trifluoromethyl or methyl, or one of $R_{13}$ and $R_{14}$ is cyano and the other is hydrogen or methyl;

$R_1$ is $C_1$—$C_6$ alkyl which may optionally be substituted with one or two substituents $R_8$ independently selected from the group consisting of hydroxy, fluoro, chloro, bromo, iodo, $CF_3$ and $C_1-C_4$ alkoxy, and wherein said $C_1-C_6$ alkyl and the $(C_1-C_4)$alkyl moiety of said $C_1$—$C_4$ alkoxy may optionally contain one carbon-carbon double or triple bond;

$R_2$ is $C_1-C_{12}$ alkyl, aryl or —$(C_1-C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or —$(C_1-C_6$ alkylene) cycloalkyl, wherein one or two of the ring carbons of said cycloalkyl having at least 4 ring members and the cycloalkyl moiety of said —$(C_1-C_6$ alkylene) cycloalkyl having at least 4 ring members may optionally be replaced by an oxygen or sulfur atom or by N—$R_9$ wherein $R_9$ is hydrogen or $C_1-C_4$ alkyl; and wherein each of the foregoing $R_2$ groups may optionally be substituted with from one to three substituents independently selected from chloro, fluoro and $C_1-C_4$ alkyl, or with one substituent selected from bromo, iodo, $C_1-C_6$ alkoxy, —O —CO—($C_1-C_6$ alkyl), —O—CO—N($C_1-C_4$ alkyl)($C_1-C_2$ alkyl), —S($C_1-C_6$ alkyl), CN, $NO_2$, —SO($C_1-C_4$ alkyl), and —$SO_2$ ($C_1-C_4$ alkyl), and wherein said $C_1-C_{12}$ alkyl and the $C_1-C_4$ alkylene moiety of said —$(C_1-C_4$ alkylene)aryl may optionally contain one carbon-carbon double or triple bond;

or —$NR_1R_2$ may form a saturated 5- to 8-membered carbocyclic ring which may optionally contain one or two carbon-carbon double bonds and in which one or two of the ring carbons may optionally be replaced by an oxygen or sulfur atom;

$R_3$ is methyl, ethyl, fluoro, chloro, bromo, iodo, cyano, methoxy, $OCF_3$, methylthio, methylsulfonyl, $CH_2OH$, or $CH_2OCH_3$;

$R_4$ is hydrogen, $C_1-C_4$ alkyl, fluoro, chloro, bromo, iodo, $C_1$—$C_4$ alkoxy, trifluoromethoxy, —$CH_2OCH_3$, —$CH_2OCH_2CH_3$, —$CH_2CH_2OCH_3$, —$CH_2OF_3$, $CF_3$, amino, nitro, —$NH(C_1-C_4$ alkyl), —$N(CH_3)_2$, —$NHCOCH_3$, —$NHCONHCH_3$, —$SO_n(C_1-C_4$ alkyl) wherein n is 0, 1 or 2, cyano, hydroxy, —$CO(C_1-C_4$ alkyl), —CHO, cyano or —$COO(C_1$—$C_4$ alkyl) wherein said $C_1-C_4$ alkyl may optionally contain one double or triple bond and may optionally be substituted with one substituent selected from hydroxy, amino, —NHCOCH3, —$NH(C_1-C_2$ alkyl), —$N(C_1-C_2$ alkyl)$_2$, —$COO(C_1-C_4$ alkyl), —$CO(C_1-C_4$ alkyl), $C_1-C_3$ alkoxy, $C_1-C_3$ thioalkyl, fluoro, chloro, cyano and nitro;

$R_5$ is phenyl or pyridyl and $R_5$ is substituted with from one to three substituents independently selected from fluoro, chloro, $C_1-C_6$ alkyl, and $C_1-C_6$ alkoxy, or with one substituent selected from hydroxy, iodo, bromo, formyl, cyano, nitro, trifluoromethyl, amino, —($C_1-C_6$ alkyl)O($C_1-C_6$)alkyl, —$NHCH_3$, —$N(CH_3)_2$, —COOH, —$COO(C_1-C_4$ alkyl), —$CO(C_1-C_4$ alkyl), —$SO_2NH(C_1-C_4$ alkyl), —$SO_2N(C_1-C_4$ alkyl)($C_1-C_2$ alkyl), —$SO_2NH_2$, —$NHSO_2(C_1-C_4$ alkyl), —$S(C_1-C_6$ alkyl) and —$SO_2(C_1-C_6$ alkyl), and wherein the $C_1-C_4$ alkyl and $C_1-C_6$ alkyl moieties of the foregoing $R_5$ groups may optionally be substituted with one or two fluoro groups or with one substituent selected from hydroxy, amino, methylamino, dimethylamino and acetyl; and $R_7$ is hydrogen or methyl;

with the proviso that when A is CH or $CCH_3$, then $R_4$ is an electron deficient group such as $NO_2$, —COO ($C_1-C_4$)alkyl, —$C(=O)CH_3$, —COOH or CN;

or a pharmaceutically acceptable salt of such compound; comprising reacting a compound of the formula

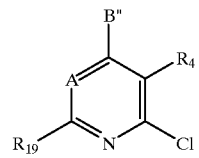

XII wherein $R_{19}$ is methyl or ethyl and A is N, CH or $CCH_3$; and wherein when A is N, then B" and $R_4$ are defined, respectively, as B and $R_4$ are defined in claim 1, and when A is CH or $CH_3$, then B" is —$NR_1R_2$, —$NHR_1R_2$, —$OCHR_1R_2$ or cyano and $R_4$ is an electron deficient group such as $NO_2$, —$COO(C_1-C_4$ alkyl), —$C(=O)CH_3$, —COOH or CN;

with a compound of the formula $R_5ZH$, wherein $R_5$ and Z are defined as above, and then optionally converting the compound of formula I formed by such reaction into a pharmaceutically acceptable salt.

This invention also relates to a process for preparing a compound of the formula

IV

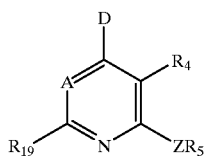

a wherein $R_{19}$ is methyl or ethyl;

D is chloro;

A is —$CR_7$ or N;

Z is NH, O, S, —$N(C_1$–$C_2$ alkyl) or —$C(R_{13}R_{14})$, wherein $R_{13}$ and $R_{14}$ are each, independently, hydrogen, trifluoromethyl or methyl, or one of $R_{13}$ and $R_{14}$ is cyano and the other is hydrogen or methyl;

$R_4$ is hydrogen, $C_1$–$C_4$ alkyl fluoro, chloro, bromo, iodo, $C_1$–$C_4$ alkoxy, trifluoromethoxy, —$CH_2OCH_3$, —$CH_2OCH_2CH_3$, —$CH_2CH_2OCH_3$, —$CH_2OF_3$, $CF_3$, amino, nitro, —$NH(C_1$–$C_4$ alkyl), —$N(CH_3)_2$, —$NHCOCH_3$, —$NHCONHCH_3$, —$SO_n(C_1$–$C_4$ alkyl) wherein n is 0, 1 or 2, cyano, hydroxy, —$CO(C_1$–$C_4$ alkyl), —CHO, cyano or —$COO(C_1$–$C_4$ alkyl) wherein said $C_1$–$C_4$ alkyl may optionally contain one double or triple bond and may optionally be substituted with one substituent selected from hydroxy, amino, —$NHCOCH_3$, —$NH(C_1$–$C_2$ alkyl), —$N(C_1$–$C_2$ alkyl)$_2$, —$COO(C_1$–$C_4$ alkyl), —$CO(C_1$–$C_4$ alkyl), $C_1$–$C_3$ alkoxy, $C_1$–$C_3$ thioalkyl, fluoro, chloro, cyano and nitro; and $R_5$ is phenyl or pyridyl, and $R_5$ is substituted with from one to three substituents independently selected from fluoro, chloro, $C_1$–$C_6$ alkyl, and $C_1$–$C_6$ alkoxy, or with one substituent selected from hydroxy, iodo, bromo, formyl, cyano, nitro, trifluoromethyl, amino, —$(C_1$–$C_6$ alkyl)$O(C_1$–$C_6)$alkyl, —$NHCH_3$, —$N(CH_3)_2$, —COOH, —$COO(C_1$—$C_4$ alkyl), —$CO(C_1$-$C_4$ alkyl), —$SO_2NH(C_1$-$C_4$ alkyl), —$SO_2N(C_1$-$C_4$ alkyl)($C_1$-$C_2$ alkyl), —$SO_2NH_2$, —$NHSO_2(C_1$-$C_4$ alkyl), —$S(C_1$-$C_6$ alkyl) and —$SO_2(C_1$-$C_6$ alkyl), and wherein the $C_1$–$C_4$ alkyl and $C_1$—$C_6$ alkyl moieties of the foregoing $R_5$ groups may optionally be substituted with one or two fluoro groups or with one substituent selected from hydroxy, amino, methylamino, dimethylamino and acetyl;

comprising reacting a compound of the formula

X

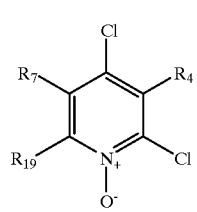

wherein $R_{19}$, $R_4$ and $R_5$ are defined as above and $R_7$ is hydrogen, methyl, fluoro, chloro, bromo, iodo, cyano, hydroxy, —$O(C_1$–$C_4$ alkyl), —$C(O)(C_1$–$C_4$ alkyl), —$C(O)O(C_1$–$C_4$ alkyl), —$OCF_3$, $CF_3CH_2OH$, —$CH_2OCH_3$ or —$CH_2OCH_2CH_3$, with phorphorus trichloride.

This invention also relates to a process for preparing a compound of the formula

X

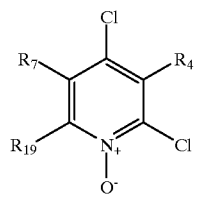

wherein $R_{19}$ is methyl or ethyl;

A is —$CR_7$ or N;

Z is O, S, or —$C(R_{13}R_{14})$, wherein $R_{13}$ and $R_{14}$ are each, independently, hydrogen, trifluoromethyl or methyl, or one of $R_{13}$ and $R_{14}$ is cyano and the other is hydrogen or methyl;

$R_4$ is hydrogen, $C_1$–$C_4$ alkyl, fluoro, chloro, bromo, iodo, $C_1$–$C_4$ alkoxy, trifluoromethoxy, —$CH_2OCH_3$, —$CH_2OCH_2CH_3$, —$CH_2CH_2OCH_3$, —$CH_2OF_3$, $CF_3$, amino, nitro, —$NH(C_1$–$C_4$ alkyl), —$N(CH_3)_2$, —$NHCOCH_3$, —$NHCONHCH_3$, —$SO_n(C_1$–$C_4$ alkyl) wherein n is 0, 1 or 2, cyano, hydroxy, —$CO(C_1$–$C_4$ alkyl), —CHO, cyano or —$COO(C_1$–$C_4$ alkyl) wherein said $C_1$–$C_4$ alkyl may optionally contain one double or triple bond and may optionally be substituted with one substituent selected from hydroxy, amino, —$NHCOCH_3$, —$NH(C_1$–$C_2$ alkyl), —$N(C_1$–$C_2$ alkyl)$_2$, —$COO(C_1$–$C_4$ alkyl), —$CO(C_1$–$C_4$ alkyl), $C_1$–$C_3$ alkoxy, $C_1$–$C_3$ thioalkyl, fluoro, chloro, cyano and nitro; and $R_5$ is phenyl or pyridyl, and $R_5$ is substituted with from one to three substituents independently selected from fluoro, chloro, $C_1$–$C_6$ alkyl, and $C_1$–$C_6$ alkoxy, or with one substituent selected from hydroxy, iodo, bromo, formyl, cyano, nitro, trifluoromethyl, amino, —$(C_1$–$C_6$ alkyl)$O(C_1$–$C_6)$alkyl, —$NHCH_3$, —$N(CH_3)_2$, —COOH, —$COO(C_1$—$C_4$ alkyl), —$CO(C_1$-$C_4$ alkyl), —$SO_2NH(C_1$-$C_4$ alkyl), —$SO_2N(C_1$-$C_4$ alkyl)($C_1$-$C_2$ alkyl), —$SO_2NH_2$, —$NHSO_2(C_1$-$C_4$ alkyl), —$S(C_1$-$C_6$ alkyl) and —$SO_2(C_1$-$C_6$ alkyl), and wherein the $C_1$–$C_4$ alkyl and $C_1$–$C_6$ alkyl moieties of the foregoing $R_5$ groups may optionally be substituted with one or two fluoro groups or with one substituent selected from hydroxy, amino, methylamino, dimethylamino and acetyl;

comprising reacting a compound of the formula

XI

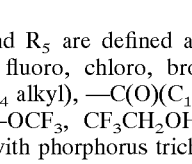

wherein $R_4$, $R_7$ and $R_{19}$ are defined as above, with a compound of the formula $R_5OH$ or $R_5SH$, wherein $R_5$ is defined as above, in the presence of a base.

DETAILED DESCRIPTION OF THE INVENTION

Methods of preparing the compounds and compositions of this invention are described below. In the discussion and reaction schemes that follow, $R_1$ through $R_9$, $R_{11}$, $R_{12}$, $R_{16}$, $R_{17}$, $R_{19}$, A, B, G, the dashed lines and structural formulae I, II, III, X, XI, XII and IV, unless otherwise indicated, are defined as above.

Whenever reference is made herein to $C_1$–$C_6$ alkyl, a straight or branched chain alkyl of one to six carbon atoms is meant, such as methyl, ethyl, isopropyl, t-butyl or hexyl.

Whenever $R_2$ or $R_5$ is a heterocyclic group, attachment of the group is through a carbon atom.

Whenever reference is made herein to $C_1$–$C_4$ alkyl or $C_1$—$C_6$ alkyl which "may contain one double or triple bond" in the definitions of $R_1$, $R_2$ and $R_3$, it is understood that at least two carbons are present in the alkyl for one double or triple bond.

Whenever reference is made herein to halo or halogen, fluoro, chloro, bromo or iodo is meant unless indicated otherwise.

Compounds of the formula I wherein B is —$NR_1R_2$, —$NHCHR_1R_2$, —$OCHR_1R_2$ or —$SCHR_1R_2$, and $R_3$ is methyl, ethyl or chloro (hereinafter $R_{19}$) may be prepared by reaction of a compound of the formula IV wherein D is Cl, and A, $R_4$, $R_5$, and Z are as defined above with reference to formula I, with a compound of the formula BH wherein B is as defined immediately above. The reaction is carried out in a solvent in the presence of a base at a temperature of between about 0° to about 230° C. Suitable solvents are organic solvents such as tetrahydrofuran (THF), acetonitrile, dimethylsulfoxide (DMSO), acetone, $C_2$–$C_{15}$ alkyl alcohol, chloroform (CHCl$_3$), benzene, xylene, toluene, sulfolane, pyridine, quinoline, 2,4,6-trimethylpyridine, acetamide, di-($C_1$–$C_2$)alkylacetamide or 1-methyl-2-pyrrolidinone.

A preferred method of preparing compounds of the formula I wherein A is —$CR_7$ and B is —$NR_1R_2$ or —$NHCHR_1R_2$ is the two step procedure described below. First, a compound of the formula IV is reacted with an excess of $R_1NH_2$ or $NH_3$ or an equivalent $NH_3$ precursor (e.g., $NaN_3$, $nBu_4N^+N_3^—$ or $NH_2OH$) at temperature from about 75° C. to about 250° C. and at a pressure from about 0 to about 300 psi, in an appropriate solvent, as described above, to form a compound of the formula I wherein B is —$NHR_1$, —$NH_2$, —$NH_2OH$ or —$N_3$. Compounds of the formula I wherein B is —$N_3$ or —$NH_2OH$ can be converted into the corresponding compounds of formula I wherein B is —$NH_2$ by methods well known in the art such as hydrogenation or reduction. Alkylation of a compound of the formula I wherein B is —$NHR_1$ or —$NH_2$ with an appropriate alkyl halide in the presence of an appropriate base such as lithium or sodium bistrimethylsilylamide, lithium or sodium diisopropylamide, n-butyllithium or potassium t-butoxide, in an appropriate solvent such as THF, dioxane or methylene chloride, will yield the corresponding compound of formula I wherein B is —$NR_1R_2$. Alternatively, reductive amination of a compound of the formula I wherein B is —NHR, or —$NH_2$, for example, acylation, followed by reduction with a borohydride (e., sodium borohydride) will form the corresponding compound of formula I wherein B is —$NR_1R_2$ or $NHCHR_1R_2$.

When B is —$NR_1R_2$ or —$NHCHR_1R_2$, an excess of BH may be used both as a reagent and as a base. Bases other than BH such as potassium carbonate, tri-($C_1$–$C_6$)alkylamine or sodium hydride may also be used. The reaction is carried out at a temperature of about 75° to 230° C. When the reaction is carried out in the presence of a base, such as sodium hydride, potassium $C_1$–$C_4$ alkoxide, or an organolithium compound such as n-butyllithium, a molar equivalent of the amine is used.

When B is —$OCHR_1R_2$ or —$SCHR_1R_2$, a base which is capable of deprotonating BH may be used, such as an alkali metal hydride such as sodium or potassium hydride, or an organometallic base such as sodium diisopropylamide, sodium bis(trimethylsilyl)amide,lithiumdiisopropylamide, lithiumbis(trimethylsilyl)amide, sodium or potassium $C_1$–$C_4$ alkoxide, or n-butyllithium. The solvent used can be, for example, tetrahydrofuran, acetonitrile, dimethylsulfoxide, acetone, methylene chloride, toluene, a $C_2$–$C_5$ alcohol, chloroform, benzene, xylene, or 1-methyl-2-pyrrolidinone, and the reaction temperature can range from about 0° C. to about 180° C., and is preferably from about 50° C to about 80° C.

Compounds of the formulae I, II and III wherein B is as defined with reference to formulae I, II and III and $R_3$ is defined with reference to the same except that $R_3$ is not methyl or ethyl (hereinafter $R_{20}$, which is defined as $R_3$ with the exception that it can not be methyl or ethyl) may be prepared by reacting a compound of the formulae I, II or III wherein $R_3$ is chloro with a nucleophile of the formula $R_{20}H$ with or without an organic or inorganic base. Suitable bases include sodium and sodium hydride, when $R_{20}H$ is an alkanol or an alkane thiol; and weaker bases such as potassium carbonate or triethylamine when $R_{20}H$ is an amine. The compounds of formula I wherein $R_{20}$ is fluoro may be prepared from the corresponding compounds wherein $R_{20}$ is chloro on reaction with tetrabutylammonium fluoride. Suitable solvents are dimethylsulfoxide, tetrahydrofuran, or methylene chloride, preferably tetrahydrofuran.

Compounds of the formula I wherein B is —$CR_1R_2R_{11}$, —$C(C=CR_2R_{12})R_1$, —$CHR_2OR_{12}$, —$CHR_2SR_{12}$, or —$C(O)R_2$, and $R_3$ is $R_{19}$, as defined above, may be prepared as depicted in Scheme I.

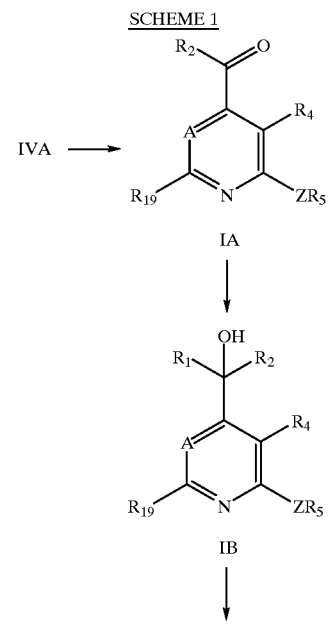

SCHEME 1

-continued

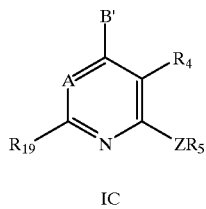

IC

Compounds of the formula IV wherein D is cyano and A, $R_4$, $R_5$, and $R_{19}$ are as defined above having formula IVA (not shown), prepared by reacting the corresponding compound wherein D is chloro with potassium cyanide or copper cyanide in dimethylsulfoxide, 1-methyl-2-pyrrolidinone, N,N-dimethylformamide (DMF) or acetamide, are reacted with a Grignard reagent containing group $R_2$, as defined above, to form the compounds of formula IA. Further reaction of the compound of formula IA with a Grignard reagent containing $R_1$ as defined above provides the compound of formula IB. Corresponding compounds of formula IC wherein B' is —$CR_1R_2R_{11}$, or —$C(C$=$CR_2R_{12})R_1$ may be prepared by conventional methods. Thus, reaction of IB with an acid, such as concentrated sulfuric acid in acetic acid, or Burgess inner salt, such as (carboxysulfamoyl) triethylammonium hydroxide methyl ester, gives a compound of -formula IC wherein B' is —$C(=CR_2R_{12})R_1$. Hydrogenation of a compound wherein B' is —$C(=CR_2R_{12})R_1$ using a palladium/carbon (Pd/C) or platinum dioxide catalyst gives a compound IC wherein B' is $CHR_1R_2$. Reaction of compound IB with diethylaminosulfur trifluoride or triphenylphosphine/carbontetrachloride affords a compound IC wherein B' is —$CR_1R_2F$ or —$CR_1R_2Cl$, respectively. Reduction of a compound of formula IA with sodium borohydride gives a compound I wherein B is —$CHR_2OH$. Alkylation of this —$CHR_2OH$ group with alkyl halide such as alkyl iodide in the presence of a base such as sodium hydride at room temperature affords a compound of formula I wherein B is —$CHR_2OR_{12}$.

Compounds of the formula 11 wherein $R_3$ is $R_{19}$ as defined above may be prepared from compounds of the formula IV wherein $R_{19}$, $R_4$, $R_5$ and A are as defined before, D is chloro, and $YR_{21}$ is NH or —$CHR_{21}$ wherein $R_{21}$ is cyano or —$COO(C_1-C_4$ alkyl), hereafter formula IVB, as shown in Scheme 2.

SCHEME 2

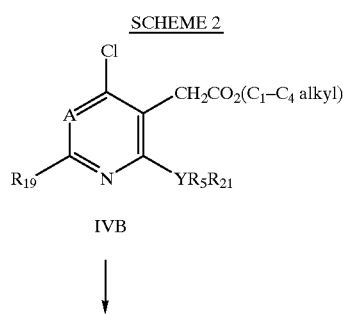

IVB

-continued

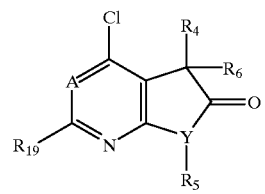

VII

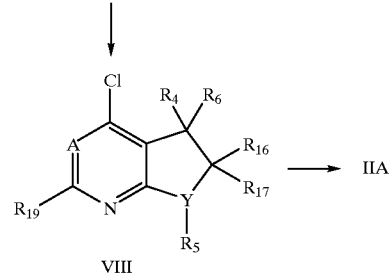

VIII

Compounds of the formula VII wherein $R_4$ and $R_6$ are each hydrogen and Y is N may be prepared by heating compounds of formula IVB with an acid catalyst in a suitable solvent such as toluene, benzene, t-butanol, acetonitrile and acetone, preferably toluene. The acid catalyst may be sulfuric acid, hydrochloric acid, p-toluene sulfonic acid, or methylsulfonic acid, preferably p-toluene sulfonic acid.

When Y in formula IVB is CH or N, a base may be used to deprotonate the proton of the compound of formula IVB. Suitable solvents are tetrahydrofuran, toluene, and methylene chloride, suitable reaction temperatures are between about −78° C. and 100° C., preferably −78° to 50° C., and suitable bases are sodium hydride, potassium hydride, potassium t-butoxide, lithium bis(trimethylsilyl) amide, and lithium or sodium diisopropylamide.

Compounds of the formula VII wherein $R_4$ and $R_6$ are each hydrogen may be deprotonated with a base such as sodium hydride, or an organometallic compound such as lithium bis(trimethylsilyl)amide followed by quenching with an electrophile compound containing the group $R_4$, such as $R_4L$ wherein L is a leaving group such as iodo, bromo, mesylate, tosylate or with p-tolyl—N-fluoro—N—$C_1$–$C_6$ alkyl sulfonamide, iodine, p-nitrobenzene, dimethylformamide, di($C_1$–$C_4$ alkyl)ketone, formaldehyde, ($C_1$–$C_4$ alkyl) aldehyde or bromine, to provide a compound of formula VII wherein $R_4$ is fluoro, chloro, bromo, iodo, hydroxy, $C_1$–$C_4$ alkyl, S($C_1$–$C_4$ alkyl), CHO, CH(OH)($C_1$–$C_4$ alkyl), C(OH)(di-$C_1$–$C_4$ alkyl) or $CH_2OH$. Further conventional alkylation of the hydroxy group or oxidation of the thioalkyl group leads to compounds of formula VII wherein $R_4$ is $C_1$–$C_4$ alkoxy and $SO_n(C_1$–$C_4$ alkyl) wherein n is 1 or 2, respectively. Oxidation of compounds of formula VII wherein $R_4$ is hydroxy and $R_6$ is hydrogen affords corresponding compounds wherein $CR_4R_6$ is C=O, which on reductive amination with an appropriate amine convert into corresponding compounds wherein $R_4$ is amino. The compounds of formula VII wherein $R_4$ is nitro or amino may be formed by reacting compounds of formula VII wherein $R_4$ and $R_6$ are both hydrogen with alkyl nitrite to form compounds wherein $CR_4R_6$ is C=NOH and oxidizing or reducing to give the compounds of formula VII wherein $R_4$ is nitro or amine, respectively.

Compounds of the formula VII, when one of $R_4$ and $R_6$ is hydrogen, may be converted into corresponding compounds wherein $R_{16}$ and $R_{17}$ are both hydrogen by reduction with a reducing agent such as lithium aluminum hydride in tetrahydrofuran. The same reduction leads to compounds wherein $R_{16}$ is hydrogen and $R_{17}$ is hydroxy, when both of $R_4$ and Re, are not hydrogen. Alkylation of $R_{17}$ is hydroxy with $C_1$–$C_4$ alkyl iodide in the presence of sodium hydride gives the corresponding compound wherein $R_{17}$ is $O(C_1$–$C_4$ alkyl). Reaction of compounds of formula VII with an organometallic compound such as di($C_1$–$C_6$ alkyl)zinc, $C_1$–$C_6$ alkyl lithium, or $C_1$–$C_6$ alkyl magnesiumbromide affords compounds of formula VII wherein one of $R_{16}$ or $R_{17}$ is $C_1$–$C_6$ alkyl and the other is hydroxy.

The conversion of compounds of formula VIII to corresponding compounds of formula IIA is by the methods described above for preparation of compounds of formula I.

The compounds of formula III wherein G is oxygen or sulfur and Re is hydrogen may be prepared by reacting compounds of formula I wherein $R_4$ is amino and Z is NH with phosgene, diphosgene, triphosgene or thiophosgene. The reaction is in the presence of a base such as tri($C_1$–$C_4$ alkyl)amine in a suitable solvent, preferable tetrahydrofurane at about –78° C. to about 50° C., preferably at 0° C. to room temperature. Standard alkylation of these compounds wherein $R_6$ is hydrogen with a suitable base such as sodium hydride in a suitable solvent such as dry tetrahydrofuran provides compounds of the formula III wherein Re is $C_1$–$C_4$ alkyl.

Compounds of the formula III wherein G is alkyl may be prepared by reacting a compound of the formula I wherein $R_4$ is amino and Z is NH with a compound of the formula $GC(OC_1$–$C_2$ alkyl)$_3$ in the presence of an acid such as p-toluenesulfonic acid (p-TsOH), methanesulfonic acid (MsOH), hydrogen chloride gas ($HCl_g$) or concentrated sulfuric acid ($H_2SO_4$) in an appropriate sovlent such as toluene, xylene, benzene, dioxane or THF at a tempeature from about room temperature to about 140° C., preferably from about 50° C. to about the reflux temperature. Alternatively, a compound of the formula I wherein $R_4$ is amino and Z is NH can be reacted with [G(C=O)]$_2$O, G(C=O)Cl or G(C=O)F in the presence of a base such as pyridine, a derivative of pyridine or a tri-($C_1$–$C_4$) alkylamine, in an appropriate solvent such as $CH_2Cl_2$, $CHCl_3$, THF, dioxane, toluene or benzene, at a temperature from about 0° C. to about the reflux temperature of the reaction mixture, preferably from about 0° C. to about room temperature, followed by ring cyclization under acidic conditions (e., with pTSOH, MSOH, $HCl_g$, hydrogen bromide gas ($HBr_g$) or concentrated $H_2SO_4$). The ring cyclization can be carried out in an appropriate solvent such as a $C_1$–$C_5$ alcohol, toluene, xylene, benzene, dioxane or THF. Suitable temperatures for this reaction can range from about room temperature to about 140° C. Preferably, the reaction temperature is between about 50° C. and about the reflux temperature.

Compounds of the formula III wherein G is —O—($C_1$–$C_2$ alkyl) or —$OCF_3$ may be prepared by reacting a compound of the formula III wherein G is oxygen and $R_6$ is hydrogen with a compound of the formula $GOSO_2CF_3$ in the presence of a base such as tri($C_1$–$C_4$ alkyl)amine, or with lithium bistrimethylsilylamide in HMPA or DMF, and then quenching the reaction with a compound of the formula $GOSO_2OG$ or G—X wherein X is bromo, chloro or $SO_3CF_3$.

The compounds of formula IV wherein D is chloro and $ZR_5$ is $NHR_5$ may be prepared from compounds of formula V:

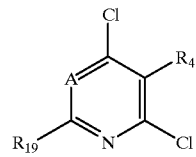

V wherein A and $R_4$ are as defined with reference to formula I and $R_{19}$ is as defined above, by reaction with $R_5NH_2$. The reaction is in tetrahydrofuran or dimethylsulfoxide at about 0° C. to about 150° C., preferably 50° to 130° C. The compounds of formula IV wherein D is chloro and Z is O, S, $CHR_{21}$ wherein $R_2$, is an electron deficient group such as cyano, C(=O)R, COOR, wherein R is $C_1$–$C_4$ alkyl, benzoyl or allyl, or $SO_n$— phenyl wherein n=0, 1 or 2 may be prepared by reacting compounds of formula V with $R_5OH$, $R_5SH$, $R_5NH_2$ or $R_5CHR_{21}$. The reaction proceeds in the presence of a base which is capable of deprotonating $R_5ZH$, such as sodium hydride, potassium hydride, potassium carbonate, lithium or sodium bis(trimethylsilyl)amide, lithium or sodium dialkylamide, sodium or potassium ($C_1$–$C_4$ alkoxide) or n-butyllithium, with or without other organometal halides such as copper (I) bromide, iodide or chloride, copper (II) oxide, copper (I) oxide, copper metal and trialkyltinchloride. Examples of solvents that may be used are tetrahydrofuran, dimethylsulfoxide, acetonitrile, methylene chloride, 1-methyl-2-pyrrolidinone, pyridine, quinoline, N,N-dialkylacetamides, 2,4,6-trimethylpyridine, N,N-dialkylformamides, e.g., N,N-dimethylformamide (DMF), hexamethyl phosphoramide and toluene. The reaction temperature may range from about 0° C. to about 180° C., and is preferably from about 0° to about 150° C.

Compounds of the formula IV wherein A is $CR_7$, D is chloro and Z is O, S, $CHR_{21}$ may be prepared by reduction of compounds of formula X, depicted below, wherein $R_7$ and Z are as defined immediately above, with a reducing agent such as phosphorous trichloride in an appropriate solvent such as methylene chloride or chloroform at temperature from about 0° C. to about 100° C., preferably from about room temperature to about the reflux temperature of the solvent.

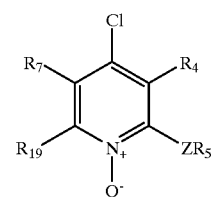

X

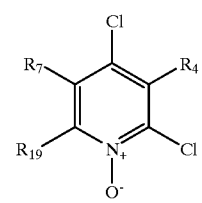

XI

Compounds of the formula X may be prepared from compounds of the formula XI, depicted above, wherein $R_4$ is as defined as it is for formula I and $R_{19}$ is as defined above (i.e., methyl or ethyl), by reaction with a compound of the formula $R_5OH$, $R_5SH$ or $R_5CHR_{21}$. This reaction proceeds in the presence of a base which is capable of deprotonating $R_5ZH$, such as sodium hydride, potassium hydride, lithium, sodium or potassium bis(trimethylsilyl)amide, lithium, sodium or potassium dialkylamide, sodium or potassium $C_1$–$C_4$alkoxide, or n-butyllithium. Suitable solvents include tetrahydrofuran, dioxane, dimethylsulfoxide, 1-methyl-2-pyrrolidinone, pyridine, N,N-di-($C_1$–$C_4$ alkyl)acetamides, acetamide, N,N-di-($C_1$–$C_4$ alkyl)formamides, acetonitrile, methylene chloride, touluene and xylene. Suitable reaction temperatures may range from about $-78°$ C. to about $150°$ C., and are preferably between about $40°$ C. to about $150°$ C.

Compounds of the formula XI may be prepared by reacting the corresponding compounds of formula V wherein A is —$CR_7$ and $R_4$ and $R_{19}$ are defined as above, with an oxidizing agent such as m-chloroperbenzoic acid, peracetic acid or pertrifluoroacetic acid, in a solvent such as methylene chloride, chloroform, acetic acid, DMF, methanol or a mixture of one or more of the foregoing solvents, at a temperature from about $0°$ C. to about $100°$ C., preferably from about room temperature to about $60°$ C.

When $R_4$ is an electron withdrawing group such as a $NO_2$, —COO($C_1$–$C_4$ alkyl), —COOH, CN or —CO($C_1$–$C_4$)alkyl, the reaction order for the coupling reactions that introduce the B and $ZR_5$ groups in the synthesis of compounds of formula I may be reversed. The B group may be introduced before the $ZR_5$ coupling step using the methods analogous to those described above. For example, compounds of the formula I wherein $R_4$ is an election deficient group may be prepared by reacting a compound of the formula XII with a compound of the formula $HZR_5$. Compounds of the formula XII may be prepared by reacting a compound of the formula V wherein A is $CR_7$ and $R_{19}$ and $R_4$ are defined as above with a compound of the formula B"H in the presence of a base.

Compounds of the formula IV wherein D is chloro and Z is —N($C_1$–$C_4$ alkyl) may be prepared by reacting the corresponding compounds wherein Z is NH with a base, at a temperature from about $-78°$ C. to about $100°$ C., preferably from about $0°$ C. to about room temperature, followed by quenching with $C_1$–$C_4$ alkyl iodide or bromide. Suitable bases include, for example, sodium hydride, lithium or sodium bis(trimethylsilyl)amide, lithium or sodium dialkylamide, and n-butyllithium. Suitable solvents include, for example, tetrahydrofuran, dimethylsulfoxide, toluene, benzene or methylene chloride.

Compounds of the formula IV wherein D is chloro, hydroxy or OP wherein P is a standard protecting group for hydroxy and Z is —$CR_{13}R_{14}$ may be prepared by alkylation, using an $R_{13}$ containing alkylating agent such as $R_{13}I$, compounds of the formula IV wherein Z is —$CHR_{21}$ in the presence of a base that is capable of deprotonating the proton in the Z group, as mentioned above, followed by quenching with an $R_{14}$ containing alkylating agent such as $R_{14}I$. Heating compounds of the formula IV wherein D is chloro or hydrogen and Z is —CH(CN) in about 85% phosphoric acid at about the reflux temperature yields the corresponding compounds of formula IV wherein D is hydroxy and Z is $CH_2$. Deprotonation of the compounds of formula IV wherein Z is $CH_2$ with a base, such as described above for deprotonation of $R_5ZH$, followed by quenching with a suitable electrophile such as a ($C_1$–$C_6$ alkyl)iodide, iodine, bromine, acetylchloride, formaldehyde, acetone, p-tolyl—N-fluoro—N-($C_1$—$C_6$ alkyl)sulfonamide, nitrobenzene, $C_1$—$C_6$ alkylnitrite, ethylene oxide or dihaloethane yields the corresponding compounds of formula IV wherein Z is —$CHR_{13}$, —CH(OH), cyclopropyl or —C(NOH). Further alkylation of compounds wherein Z is —$CHR_{13}$, e.g., as described immediately above, with an alkylating agent of the formula $R_{14}I$, produces the corresponding compounds wherein Z is —$C(R_{13}R_{14})$.

Conversion of —$C(R_5)NOH$ or —CH(OH)$R_5$ to $C(O)R_5$ may be accomplished by known methods. Hydrogenation or reduction of compounds wherein Z is —C═NOH provides compounds wherein Z is —$CHNH_2$. Some of the intermediates may require a protecting or deprotecting procedure to control the reaction selectivity using standard organic chemistry.

Compounds of the formula V wherein A is N (hereinafter referred to as compounds of the formula VB) or A is $CR_7$ (i.e., compounds of the formula VA), and $R_4$ and $R_{19}$ are defined as they are for formula I, may be prepared by reacting the corresponding compounds of formulae VIB and VIA, respectively, with 1 equivalent or an excess of $POCl_3$ at a temperature from about room temperature to about $180°$ C., preferably at the reflux temperature, with or without a solvent. Compounds of formula VIA may be prepared by the methods analogous to those described in the literature and well known to those skilled in the art. (See *Helv. Chimica Acta.*, 25, p. 1306–1313 (1942)).

Compounds of formula VIB may be prepared by reacting 1 equivalent of the HCl salt of $R_{19}C(═NH)(NH_2)$, 1 equivalent of $R_4CH(COO—(C_1-C_2$ alkyl))$_2$, and 2 equivalents of a base such as a sodium alkoxide, e.g., sodium methoxide in a mixture of an alcohol (e.g., methanol), and acetone at a temperature from about $50°$ C. to about $200°$ C., preferably at the reflux temperature.

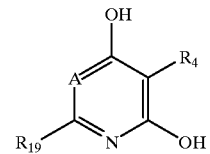

VIA, A = $CR_7$
VIB, A = N

When compounds of this invention contain one or more chiral centers, it is understood that the invention includes the racemic mixtures as well as all individual enantiomers and diastereomers of such compounds, and mixtures thereof.

The acid addition salts of compounds of the formulae I, II and III (the active compounds of this invention) can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The active compounds of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formulae I, II and III and their pharmaceutically acceptable carriers can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for compounds of the formulae I, II or III and their salts will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastrointestinal diseases, anorexia nervosa, hemorrhagic stress and drug and alcohol withdrawal symptoms will generally range from about 0.1 to about 50 mg/kg body weight of the patient to be treated.

Methods that may be used to determine the CRF antagonist acivity of the active compounds of this invention and their pharmaceutically acceptable salts are described in *Endocrinology*, 116, 1653–1659 (1985) and *Peptides*, 10, 179–188 (1985). The binding activities for compounds of formulae I, II and III, expressed as $IC_{50}$ values, generally range from about 0.5 nanomolar to about 10 micromolar.

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform (CDCl$_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

The following abbreviations are used in the Examples: Ph=phenyl; iPr=isopropyl; HRMS=high resolution mass spectrum.

EXAMPLE 1

A. Butyl-(6-chloro-2,5-dimethyl-pyrimidin-4-yl)-ethylamine

A mixture of 2,5-dimethyl-4,6-dichloro-pyrimidine (0.999 g, 5.64 mmol) in 5 ml of acetonitrile was treated with triethylamine (0.571 g, 5.65 mmol) and N-butyl-ethyl-amine (0.570 g, 5.65 mmol) and heated at reflux overnight. The mixture was cooled, diluted with water and dilute hydrogen chloride, and extracted with ethyl acetate. The organic layer was neutralized with saturated potassium carbonate, washed with brine, dried and concentrated to give 0.877 g (64%) of title compound as a yellow oil. $^1$H NMR (CDCl$_3$) δ0.90 (t, 3H), 1.15 (t, 3H), 1.22–1.36(m, 2H), 1.5–1.6(m, 2H), 2.20 (s, 3H), 2.45 (s, 3H), 3.25–3.48 (m, 4H) ppm.

B. N-Butyl—N-ethyl-2,5-dimethyl-N'-(2,4,6-trimethylphenyl)-pyrimidine-4,6-diamine A mixture of butyl-(6-chloro-2,5-dimethyl-pyrimidin-4-yl)-ethylamine (398 mg, 1.65 mmol), 2,4,6-trimethylaniline (4.04 g, 30 mmol) and diisopropyl-ethyl-amine (200 mg, 1.55 mmol) was heated at 210 to 230° C. overnight. The mixture was quenched with water and dilute hydrogen chloride, and extracted with ethyl acetate. The organic layer was neutralized with saturated potassium carbonate, washed with brine, dried and concentrated to give a dark oil. The oil was distilled to give 579 mg of dark oil which was then purified through silica gel column chromatography using 1:1 hexane to chloroform as eluent to give 327 mg of title compound as a yellow solid. $^1$H NMR (CDCl$_3$) δ0.92 (t, 3H), 1.14 (t, 3H), 1.2–1.4 (m, 2h), 1.45–1.60 (m, 2H), 1.85 (s, 3H), 2.16 (s, 6H), 2.30 (s, 3H), 2.33 (s, 3H), 3.2–3.4 (m, 4H), 5.8 (brs, 1H), 6.90 (s, 2H) ppm.

EXAMPLE 2

A. Butyl-(6-chloro-2-methyl-pyrimidin-4-yl)-ethylamine

A mixture of 2-methyl-4,6-dichloro-pyrimidine (1.63 g, 10 mmol) In 5 ml of acetonitrile was treated with N-butyl-ethyl-amine (2.000 g, 20 mmol) and heated at reflux for 0.5 hours. The mixture was cooled, diluted with water and extracted with ethyl acetate. The organic layer was washed with brine, dried and concentrated to give 2.271 g (100%) of title compound as a light-brown oil. $^1$H NMR (CDCl$_3$) δ0.93 (t, 3H), 1.13 (t, 3H), 1.22–1.36 (m, 2H), 1.45–1.6 (m, 2H), 2.43 (s, 3H), 3.25–3.60 (m, 4H), 6.15 (s, 1H) ppm.

B. N-Butyl—N-ethyl-2-methyl-N'-(2,4,6-trimethylphenyl)-pyrimidine-4,6-diamine

A mixture of butyl-(6-chloro-2-methyl-pyrimidin-4-yl)-ethylamine (1.006 g, 4.42 mmol), and 2,4,6-trimethylaniline (3 ml) was heated at reflux overnight. The mixture was quenched with water and extracted with ethyl acetate. The organic layer was dried and concentrated to give 2.862 g of a brown oil. The oil was purified through silica gel column chromatography to give 981 mg (68%) of title compound as a yellow oil. $^1$H NMR (CDCl$_3$) δ0.80 (t, 3H), 1.1–1.3 (m, 2H), 1.3–1.5 (m, 2H), 2.17 (s, 6H), 2.27 (s, 3H), 2.41 (s, 3H), 3.2 (m, 2H), 3.36 (m, 2H), 4.66 (s, 1H), 6.90 (s, 2H) ppm.

EXAMPLE 3

A. Butyl-(6-chloro-2-methyl-5-ethyl-pyrimidin-4-yl)-ethylamine

A mixture of 2-methyl-5-ethyl-4,6-dichloro-pyrimidine (1.009 g, 5.28 mmol) in 5 ml of acetonitrile was treated with triethylamine (0.571 g, 5.65 mmol) and N-butyl-ethyl-amine (0.540 g, 5.31 mmol) and heated at reflux overnight. The mixture was diluted with water and dilute hydrogen chloride, and extracted with ethyl acetate. The organic layer was neutralized with saturated potassium carbonate and washed with brine, dried and concentrated to give 1.193 g of yellow oil which was purified through silica gel column chromatography to give 1.157 g (86%) of title compound as a yellow oil. $^1$H NMR (CDCl$_3$) δ0.90 (t, 3H), 1.13 (t, 3H), 1.18 (t, 3H), 1.1–1.33 (m, 2H), 1.4–1.6 (m, 2h), 2.41 (s, 3H), 2.62 (q, 2H), 3.25–3.48 (m, 4H) ppm.

B. N-Butyl-N-ethyl-2-methyl-5-ethyl-N'-(2,4,6-trimethylphenyl)-pyrimidine-4,6-diamine A mixture of butyl-(6-chloro-2-methyl-5-ethyl-pyrimidin-4-yl)-ethylamine (200 mg, 0.78 mmol) and 2,4,6-trimethylaniline (0.963 g, 7.1 mmol) was heated at reflux for 4 hours. The mixture was quenched with water and extracted with ethyl acetate. The organic layer was washed with saturated potassium carbonate and brine, dried and concentrated to give a dark oil. The oil was distilled to give 579 mg of the dark oil which was then purified through silica gel column chromatography using chloroform as eluent to give the title compound as a brown oil. $^1$H NMR (CDCl$_3$) δ0.93 (t, 3H), 1.14 (t, 3H), 1.1–1.4 (m, 4H), 1.45–1.60 (m, 2H), 2.17 (s, 6H), 2.30 (s, 3H), 2.33 (s, 3H), 3.2–3.4 (m, 4H), 6.90 (s, 2H) ppm.

EXAMPLE 4

2-Methyl-5-nitro-N,N'-bis-(2,4,6-trimethylphenyl)-pyrimidine-4,6-diamine

A mixture of 2-methyl-5-nitro-4,6-dichloropyrimidine (0.513 g, 2.47 mmol) in 6 ml of acetonitrile was treated with 2,4,6-trimethylaniline (0.333 g, 2.46 mmol) and triethylamine (1 ml) and stirred at room temperature for 4 hours. The mixture was quenched with water and extracted with ethyl acetate. The organic layer was washed with brine, dried and concentrated to give 0.622 g of bright yellow solid. The solid was purified through silica gel column chromatography to give (6-chloro-2-methyl-5-nitro-pyrimidin-4-yl)-(2,4,6-trimethylphenyl) amine and the title compound. $^1$H NMR (CDCl$_3$) for 6-(chloro-2-methyl-5-nitro-pyrimidin-4-yl)-(2,4,6-trimethylphenyl)amine δ 2.16 (s, 6H), 2.33 (s, 3H), 2.43 (s, 3H), 6.95 (s, 2H), 8.79 (s, 1H) ppm. $^1$H NMR (CDCl$_3$) for 2-methyl-5-nitro-N,N'-bis-(2,4,6-trimethylphenyl)-pyrimidine-4,6-diamine: d 2.11 (s, 3H), 2.22 (s, 12H), 2.33 (s, 3H), 6.96 (s, 4H), 10.44 (s, 2H) ppm.

EXAMPLE 5

N-Butyl-N-ethyl-2-methyl-5-nitro-N'-(2,4,6-trimethylphenyl)-pyrimidine-4,6-diamine A mixture of 6-(chloro-2-methyl-5-nitropyrimidin-4-yl)-(2,4,6-trimethylphenyl)amine (838 mg, 2.10 mmol) and N-ethyl-n-butyl-amine (555 mg, 5.48 mmol) in 15 ml acetonirile was heated at reflux for 2 hours. The mixture was quenched with water and extracted with ethyl acetate. The organic layer was washed with brine, dried and concentrated to give 0.837 g of yellow oil. The solid was purified through silica gel column chromatography using 1:1 hexane to chloroform as eluent to give 753 mg of the title compound as a yellow oil. $^1$H NMR (CDCl$_3$) δ0.95 (t, 3H), 1.26 (t, 3H), 1.2–1.4 (m, 2H), 1.55–1.75 (m, 2H), 2.17 (s, 6H), 2.23 (s, 3H), 2.31 (s, 3H), 3.4–3.6 (m, 4H), 6.93 (s, 2H), 9.43 (s, 1H) ppm.

EXAMPLE 6

The following compounds were prepared by a method analogous to that of Examples 3 or 5 starting with an appropriate amine and appropriate (6-chloro-2-methyl-5-substituted-pyrimidin-4-yl)-(2,4,6-trimethylphenyl)amine.

N-Propyl-N-ethyl-2-methyl-5-nitro-N'-(2,4,6-trimethylphenyl)-pyrimidine-4,6-diamine $^1$H NMR (CDCl$_3$) δ0.93 (t, 3H), 1.26 (t, 3H). 1.6–1.8 (m, 2H), 2.17 (s, 6H), 2.23 (s, 3H). 2.31 (s, 3H), 3.4-3.55 (m, 4H), 6.93 (s, 2H), 9.41 (s, 1H) ppm.

N-Butyl-5-ethyl-2-methyl-N'-(2,4,6-trimethylphenyl)-pyrimidine-4,6-diamine $^1$H NMR (CDCl$_3$) δ0.98 (t, 3H), 1.12 (t, 3H), 1.3–1.5 (m, 2H), 1.5–1.7 (m, 2H), 2.17 (s, 3H), 2.30 (s, 3H), 3.4–3.5 (m, 2H), 4.30 (brs, 1H), 5.65 (brs, 1H), 6.91 (s, 2H) ppm.

5,N-Diethyl-2-methyl-N'-(2,4,6-trimethylphenyl)-pyrimidine-4,6-diamine $^1$H NMR (CDCl$_3$) δ1.09 (t, 3H), 1.25 (t, 3H), 2.17 (s, 3H), 2.30 (s, 3H), 2.31 (s, 3H), 3.4–3.6 (m, 2H), 4.35 (brs, 1H), 6.90 (s, 2H) ppm.

EXAMPLE 7

N-Butyl-N-ethyl-2-methyl-N'-(2,4,6-trimethylphenyl)-pyrimidine-4,5,6-triamine A mixture of N-butyl-N-ethyl-2-methyl-5-nitro-N'-(2,4,6-trimethylphenyl)-pyrimidine-4,6-diamine (242 mg, 0.65 mmol) and platinum oxide (35 mg) in 50 ml ethanol was hydrogenated at 40 psi for 24 hours. The mixture was filtered through celite and concentrated to dryness to give 217 mg of yellow oil. The oil was purified through silica gel column chromatography to give 135 mg (61%) of title compound. $^1$H NMR (CDCl$_3$) δ0.91 (t, 3H), 1.09 (t, 3H), 1.2–1.4 (m, 2H), 1.4–1.6 (m, 2H), 2.18 (s, 6H), 2.30 (s, 3H), 2.34 (s, 3H), 3.0 (brs, 2H), 3.1–3.3 (m, 4H), 5.89 (s, 1H), 6.92 (s, 2H) ppm.

EXAMPLE 8

The following compounds were prepared by the method of Example 7 by hydrogenation of the corresponding 5-nitro derivatives.

N-Propyl-N-ethyl-2-methyl-N'-(2,4,6-trimethylphenyl)-pyrimidine-4,5,6-triamine $^1$H NMR (CDCl$_3$) δ0.89 (t, 3H), 1.09 (t, 3H), 1.45–1.60 (m, 2H), 2.18 (s, 6H), 2.30 (s, 3H), 2.34 (s, 3H), 3.80 (brs, 2H), 3.1–3.30 (m, 4H), 5.95 (brs, 1H), 6.92 (s, 2H) ppm.

2-Methyl-N,N'-bis-(2,4,6-trimethylphenyl)-pyrimidine-4,5,6-triamine $^1$H NMR (CDCl$_3$) δ2.04 (brs, 2H), 2.21 (s, 12H), 2.22 (s, 3H), 2.30 (s, 6H), 6.30 (s, 2H), 6.92 (s, 4H) ppm.

EXAMPLE 9

6-(Ethyl-propyl-amino-2-methyl-9-(2,4,6-trimethylphenyl)-7,9-dihydropurin-8-one A mixture of N-propyl-N-ethyl-2-methyl-N'-(2,4,6-trimethyl-phenyl)-pyrimidine-4,5,6-triamine (120 mg, 0.35 mmol) and triethylamine (87 mg, 0.86 mmol) in 5 ml of dry tetrahydrofuran was treated with triphosgene (41 mg, 0.14 mmol) at 0° C. Precipitate formed immediately and the reaction mixture was warmed to room temperature. After stirring for 30 minutes the mixture was filtered. The filtrate was concentrated to dryness to give 125 mg (100%) of title compound of a greenish color. $^1$H NMR (CDCl$_3$) δ0.90 (t, 3H), 1.21 (t, 3H), 1.65 (m, 2H), 2.10 (s, 6H), 2.34 (s, 3H), 2.39 (s, 3H), 3.48 (dd, 2H), 3.58 (q, 2H), 6.99 (s, 2H), 9.63 (s, 1H) ppm.

EXAMPLE 10

6-(Ethyl-propyl-amino)-2,7-dimethyl-9-(2,4,6-trimethylphenyl)-7,9-dihydropurin-8-one A mixture of the title compound of Example 9 (54 mg, 0.15 mmol) in 3 ml of dry tetrahydrofuran was treated with sodium hydride (9 mg, 0.23 mmol, 60% in oil) at room temperature. The mixture was then treated with 0.02 ml of methyl iodide and stirred at room temperature overnight. The mixture was quenched with water and extracted with ethyl acetate. The organic layer was dried and concentrated to give 60 mg of brown oil. The oil was purified through silica gel column chromatography using chloroform as eluent to give 56 mg of the title compound as a yellow oil which crystallized on standing. $^1$H NMR (CDCl$_3$) δ0.92 (t, 3H), 1.17 (t, 3H), 1.63 (m, 2H), 2.06 (s, 6H), 2.33 (s, 3H), 2.46 (s, 3H), 3.32 (dd, 2H), 3.40 (q, 2H), 3.63 (s, 3H), 7.00 (s, 2H) ppm.

EXAMPLE 11

The following compounds were prepared by the method of Example 10 by reacting the title compound of Example 9 with an appropriate alkyl iodide.

7-Ethyl-6-(ethyl-proryl-amino)-2-methyl-9-(2,4,6-trimethylphenyl)-7,9-dihydropurin-8-one $^1$H NMR (CDCl$_3$) δ0.92 (t, 3H), 1.14 (t, 3H), 1.23 (m, 3H), 1.58 (m, 2H), 2.04 (s, 6H), 2.31 (s, 3H), 2.45 (s, 3H), 3.32 (dd, 2H), 3.36 (q, 2H), 4.08 (q, 2H), 7.00 (s, 2H) ppm.

6-(Ethyl-propyl-amino)-2-methyl-7-propyl-9-(2,4,6-trimethylphenyl)-7,9-dihydropurin-8-one $^1$H NMR (CDCl$_3$) δ0.87 (t, 3H), 0.90 (t, 3H), 1.15 (t, 3H), 1.5–12.8 (m, 4H), 2.05 (s, 6H), 2.33 (s, 3H), 2.47 (s, 3H), 3.32 (dd, 2H), 3.38 (q, 2H), 4.01 (q, 2H), 7.00 (s, 2H) ppm.

EXAMPLE 12

[4—Chloro-2-methyl-6-(2,4,6-trimethylphenylamino)-pyrimidin-5-yl-acetic acid ethyl ester A mixture of (2-methyl-4,6-dichloro-pyrimidine-5-yl)-acetic acid ethyl ester (1.470 g, 5.9 mmol) and 2,4,6-trimethylaniline (2.56 ml, 17.7 mmol), in 15 ml of dimethylsulfoxide was heated at 120° C. overnight and 138° C. for 5 hours. The mixture was quenched with water and extracted with ethyl acetate. The organic layer was washed with brine, dried and concentrated to give a brown oil. The oil was purified through silica gel column chromatography to give 1.070 g (52%) of the title compound as a tan solid. $^1$H NMR (CDCl$_3$) δ1.30 (t, 3H), 2.14 (s, 6H), 2.32 (s, 3H), 2.37 (s, 3H), 3.79 (s, 2H), 4.23 (q, 2H), 7.00 (s, 2H), 7.02 (s, $_1$H) ppm.

EXAMPLE 13

A. 4—Chloro-2-methyl-7-(2,4,6-trimethylphenylamino)-5,7-dihydro-pyrrolo-[2,3-d]pyimidin-6-one A mixture of the title compound of Example 12 (960 mg, 2.76 mmol) and p-toluene sulfonic acid (105 mg, 0.55 mmol) in 10 ml of toluene was heated at reflux under Dean—Stark trap for 8 hours. The mixture was quenched with water and extracted with ethyl acetate. The organic layer was washed with brine, dried and concentrated to give 800 mg of a brown mass which was purified through silica gel column chromatography to give 348 mg (42%) of the title compound as a yellow powder. $^1$H NMR (CDCl$_3$) δ2.06 (s, 6H), 2.34 (s, 3H), 2.56 (s, 3H), 3.75 (s, 2H), 7.02 (s, 2H) ppm.

B. 4-(1-Hydroxymethyl-propylamino)-2-methyl-7-(2,4, 6-trimethylphenyl)-5,7-dihydro-pyrrolo[2,3-d]pyrimidine-6-one A mixture of the compound prepared under A (168 mg, 0.557 mmol) and (S)-2-amino-butanol (0.27 ml, 2.78 mmol) in 5 ml of dimethyl sulfoxide was heated at 145° C. for 5 hours. The mixture was quenched with water and extracted with ethyl acetate. The organic layer was washed with brine, dried and concentrated to give an oil. The oil was purified through silica gel column chromatography, followed by recrystallization with diethyl ether to give 166 mg of the title compound as a grey solid.

$^1$H NMR (CDCl$_3$) δ1.25 (t, 6H), 1.5–1.8 (m, 2H), 2.07 (s, 6H), 2.31 (s, 3H), 2.37 (s, 3H), 3.50 (s, 2H), 3.4–3.9 (m, 2H), 4.0 (m, 1H), 4.* (d, 1H), 7.00 (s, 2H) ppm.

EXAMPLE 14

4-Diethylamino-2-methyl-7-(2,4,6-trimethylphenvl)-5,7-dihydro-pyrrolo[2,3-d]pyrimidin-6-one The title compound was prepared by the method of Example 13B with diethylamine instead of (S)-2-amino-butanol. $^1$H NMR (CDCl$_3$) ε1.02 (t, 3H), 2.08 (s, 6H), 2.31 (s, 3H), 2.37 (s, 3H), 3.55 (q, 4H), 3.85 (s, 2H), 6.95 (s, 2H) ppm.

EXAMPLE 15

A. 4-Chloro-2,5,5-trimethyl-7-(2,4,6-trimethylphenylamino)-5,7-dihydro-pyrrolo[2,3-d]pyrmidin-6-one and 4-Chloro-2,5-dimethyl-7-(2,4,6-trimethylphenyl)-5,7-dihydro-pyrrolo[2,3-d]pryrimidin-6-one A mixture of 4-chloro-2-methyl-7-(2,4,6-trimethylphenylamino)-5,7-dihydro-pyrrolo[2,3-d]pyrimidin-6-one (93 mg, 0.31 mmol) and sodium hydride (14 mg, 0.34 mmol, 60% in oil) in tetrahydrofuran (THF) was stirred for 5 minutes, then treated with an excess of methyl iodide and stirred for 1 hour. The mixture was quenched with water and extracted with ethyl acetate. The organic layer was washed with brine, dried and concentrated to give an oil. The oil was purified through silica gel column chromatography to give 32 mg of 4-chloro-2,5,5-trimethyl-7-(2,4,6-trimethylphenyl-amino)-5,7-dihydro-pyrrolo[2,3-d]pyrimidin-6-one and 64 mg of 4-chloro-2,5-dimethyl-7-(2,4,6-trimethyl)-phenylamino)-5,7-dihydro-pyrrolo[2,3-d]pyrimidin-6-one.

$^1$H NMR (CDCl$_3$) (4-chloro-2,5,5-trimethyl-7-(2,4,6-trimethylphenylamino)-5,7-dihydropyrrolo[2,3-d]pyrimidin-6-one) δ1.61 (s, 6H), 2.03 (s, 6H), 2.32 (s, 3H), 2.53 (s, 3H), 7.00 (s, 2H) ppm.

$^1$H NMR (CDCl$_3$) (4-chloro-2,5-dimethyl-7-(2,4,6-trimethylphenylamino)-5,7-dihydropyrrolo[2,3-d]pyrimidin-6-one) δ1.65 (d, 2H), 2.03 (s, 3H), 2.06 (s, 3H), 2.34 (s, 3H), 2.56 (s, 3H), 3.72 (q, 1H), 7.00 (s, 2H) ppm.

B. 4-1-hydroxymethylpropylamino)-2,5,5-trimethyl-7-(2,4,6-trimethylphenyl)-5,7-dihydropvrrolo[2,3-d]pyrimidin-6-one The title compound was prepared by the method of Example 13B from 4-chloro-2,5,5trimethyl-7-(2,4, 6trimethylphenylamino)-5,7-dihydro-pyrrolo[2,3-d]pyrimidin-6-one) and (S)-2-amino-butanol in dimethylsulfoxide at 140° C. $^1$H NMR (CDCl$_3$) δ1.02 (t, 3H), 1.53 (s, 6H), 1.5–1.8 (m, 2H), 2.04 (s, 6H), 2.32 (s, 3H), 2.38 (s, 3H), 3.6–3.9 (m, 2H), 4.0 (m, 1H), 4.5 (d, 1H), 5.25 (brs, 1H), 7.00 (s, 2H) ppm.

EXAMPLE 16

5-Hydroxy-4-(1-hydroxymethylpropylamino)-2.5-dimethyl-7-(2,4,6-trimethlphenyl)-5,7-dihydropyrrolo[2.,-d]pyrimidin-6-one The title compound was prepared by the method of Example 13B from 4chloro-2,5-dimethyl-7-(2,4,6-trimethylphenylamino)-5,7-dihydro-pyrrolo[2,3-d]pyrimidin-6-one) and (S)-2-amino-butanol in dimethylsulfoxide (DMSO) at 1400C. Two diastereomers were obtained. The spectra for both diastereomers are shown below:

One isomer: $^1$H NMR (CDCl$_3$) δ1.03 (t, 3H), 1.55–1.75 (m, 2H), 1.77 (s, 3H), 2.05 (s, 3H), 2.07 (s, 3H), 2.32 (s, 3H), 2.37 (s, 3H), 3.55–3.85 (m, 2H), 4.0 (m, 1H), 5.1 (d, 1H), 5.3 (brs, 1H), 7.00 (s, 2H) ppm.

The other isomer: $^1$H NMR (CDCl$_3$) δ1.03 (t, 3H), 1.55–1.75 (m, 2H), 1.73 (s, 3H), 2.02 (s, 3H), 2.05 (s, 3H), 2.32 (s, 3H), 2.36 (s, 3H), 3.58 (dd, 1H), 3.77 (dd, 1H), 4.1 (m, 1H), 5.03 (d, 1H), 7.00 (s, 2H) ppm.

EXAMPLE 17

5-Methoxy-4-(butyl-ethyl-amino)-2,5-dimethyl-7-(2,4,6-trimethylphenyl)-5,7-dihydro-pyrrolo[2,3-d]pyrimidin-6-one 5-Hydroxy-4-(butyl-ethyl-amino)-2,5-dimethyl-7-(2,4,6-trimethylphenyl)-5,7-dihydro-pyrrolo[2,3-d]pyrimidin-6-one was prepared by the method analogous to that of Example 16 starting with 4-chloro-2,5-dimethyl-7-(2,4,6-trimethylphenylamino)-5,7-dihydro-pyrrolo[2,3-d]pyrimidin-6-one) and N-butyl-ethyl-amine in DMSO at 140° C. Methylation of 5-hydroxy-(butyl-ethyl-amino)-2,5-dimethyl-7-(2,4,6-trimethylphenyl)-5,7-dihydro-pyrrolo[2,3-d]pyrimidin-6-one with sodium hydride and methyl iodide using the method of Example 10 provides the title compound. $^1$H NMR (CDCl$_3$) δ6.97 (d, 2H), 3.5–4.0 (m, 4H), 3.23 (s, 3H), 2.34 (s, 3H), 2.32 (s, 3H), 2.12 (s, 3H), 2.03 (s, 3H), 1.69 (s, 3H), 1.6–1.8 (m, 2H), 1.3–1.5 (m, 2H), 1.24 (t, 3H), 0.99 (t, 3H) ppm.

EXAMPLE 18

4-(Butyl-ethyl-amino)-2-methyl-7-(2,4, 6-trimethylphenyl)-5.,-dihydro-pyrrolo[2,3-d]pyrimidin-6-one The title compound was prepared by the method analogous to that of Example 13 (B) starting with 4-chloro-2-methyl-7-(2,4,6-trimethylphenylamino)-5,7-dihydro-pyrrolo[2,3-d]pyrimidin-6-one) and N-butyl-ethyl-amine in DMSO at 135° C. for 2.5 hours to give an oil. $^1$H NMR (CDCl$_3$) 7.00 (s, 2H), 3.85 (s, 2H), 3.62 (q, 2H), 3.53 (t, 2H), 2.35 (s, 3H), 2.32 (s, 3H), 2.10 (s, 3H), 1.55–1.70 (m, 2H), 1.35–1.50 (m, 2H), 1.25 (t, 3H), 1.00 (t, 3H) ppm.

EXAMPLE 19

4-(Butyl-ethyl-amino)-2,5-dimethyl-7-(2,4,6-trimethylphenyl)-5,7-dihydro-pyrrolo[2,3-d]pyrimidin-6-one A solution of 4-(butyl-ethyl-amino)-2-methyl-7-(2,4,6-trimethylphenyl)-5,7-dihydro-pyrrolo[2,3-d]pyrimidin-6-one (285 mg, 0.78 mmol) In 5 ml of dry THF was treated with lithium bis(trimethylsilyl)amide (1.05 mmol) at −78° C. and stirred for 5 minutes. The mixture was quenched with methyl iodide (0.054 ml, 0.858 mmol) at −78° C. After stirring for 10 minutes, the mixture was warmed to 0° C. and stirred at that temperature for 20 minutes. The mixture was quenched with saturated ammonium chloride and extracted with ethyl acetate. The organic layer was washed with brine, dried and concentrated to give a purple form. The form was purified through silica gel column chromatography to give 4-(butyl-ethyl-amino)-2,5-dimethyl-7-(2,4,6-trimethylphenyl)-5,7-dihydro-pyrrolo[2,3-d]pyrimidin-6-one (120 mg) as a purple glass, 4-(butyl-ethyl-amino)-2,5,5-trimethyl-7-(2,4,6-trimethylphenyl)-5,7-dihydro-pyrrolo[2,3-d]pyrimidin-6-one (35 mg) as a purple glass, and 98 mg of a mixture of the two components as a purple glass.

$^1$H NMR (CDCl$_3$) (4-(butyl-ethyl-amino)-2,5-dimethy-7-(2,4,6-trimethylphenyl)-5,7-dihydro-pyrrolo[2,3-d]pyrimidin-6-one) δ6.96 (s, 2H), 3.7–3.9 (m, 2H), 3.51 (q,1H), 3.15–3.4 (m, 2H), 2.34 (s, 3H), 2.30 (s, 3H), 2.08 (s, 3H), 2.05 (s, 3H), 1.53 (d, 3H), 1.5–1.65 (m, 2H), 1.3–1.4 (m, 2H), 1.17 (t, 3H), 0.95 (t, 3H) ppm.

$^1$H NMR (CDCl$_3$) (4-(butyl-ethyl-amino)-2,5,5-trimethy-7-(2,4,6-trimethylphenyl)-5,7-dihydro-pyrrolo[2,3-d]pyrimidin-6-one) δ6.98 (s, 2H), 3.45 (q, 2H), 3.34 (t, 2H), 2.34 (s, 3H), 2.33 (s, 3H), 2.06 (s, 6H), 1.55–1.7 (m, 2H), 1.3–1.45 (m, 2H), 1.23 (t, 3H), 0.99 (t, 3H) ppm.

EXAMPLE 20

Butyl-[2,5-dimethyl-7-(2,4,6-trimethylphenyl)-6,7-dihydro-5H-pyrrolo[2,3-d]pyrimidin-4-yl]-ethylamine A solution of (4-butyl-ethyl-amino)-2,5-dimethyl-7-(2,4,6-trimethylphenyl)-5,7-dihydro-pyrrolo[2,3-d]pyrimidin-6-one) (111 mg, 0.292 mmol) in dry THF was treated with lithium aluminum hydride at room temperature. The resulting mixture was heated at reflux for 5 hours. After standard work-up, 97 mg of crude material as an oil was obtained. The oil was purified through a chromatotron using 10% ethyl acetate in hexane as eluent to give butyl-[2,5-dimethyl-7-(2,4,6-trimethylphenyl)-6,7-dihydro-5H-pyrrolo[2,3-d]pyrimidin-4-yl]-ethylamine as a clear pale yellow oil. $^1$H NMR (CDCl$_3$) δ6.91 (d, 2H), 3.7–3.9 (m, 2H), 3.2–3.4 (m, 4H), 2.5 (q, 1H), 2.28 (s, 6H), 2.22 (s, 3H), 2.05 (s, 3H), 1.5–1.7 (m, 2H), 1.3–1.5 (m, 5H), 1.17 (t, 3H), 0.97 (t, 3H) ppm. High MS (C23H34N4) calc. 366.2776, found 366.27622.

EXAMPLE 21

4-(Butyl-ethyl-amino)-2,5,5-trimethyl-7-(2,4,6-trimethylphenyl)-6.7-dihydro-5H-pyrrolo[2,3-d]pyrimidin-6-ol The title compound was prepared by the method of Example 20 starting from (4-(butyl-ethyl-amino)-2,5,5-trimethyl-7-(2,4,6-trimethylphenyl)-5,7-dihydro-pyrrolo[2,3-d]pyrimidin-6-one) to give a pale yellow solid, mp 142–145° C.; $^1$H NMR (CDCl$_3$) δ6.95 (d, 2H), 4.90 (s, 1H), 3.1–3.4 (m, 4H), 2.4 (brs, 1H), 2.33 (s, 3H), 2.31 (s, 3H), 2.21 (s, 3H), 2.17 (s, 3H), 1.50 (s, 3H), 1.45 (s, 3H), 1.25–1.60 (m, 4H), 1.11 (t, 3H), 0.93 (t, 3H) ppm.

EXAMPLE 22

Butyl-ethyl-[6-methoxy-2,5,5-trimethyl-7-(2,4,6-trimethylphenyl)-6,7-dihydro-5H-pyrrolo[2,3-d]pyrimidin-4yl]-amine To a solution of 4-(butyl-ethyl-amino)-2,5,5-trimethyl-7-(2,4,6-trimethylphenyl)-6,7-dihydro-5H-pyrrolo[2,3-d]

pyrimidin-6-ol] (20 mg, 0.05 mmol) in 1 ml of dry THF was treated with sodium hydride (60% in oil, 4 mg, 0.1 mmol) and then methyl iodide (0.3 ml) was added at room temperature. After stirring at room temperature for 2.5 hours, the mixture was quenched with saturated ammonium chloride and extracted with ethyl acetate. The organic layer was washed with brine, dried and concentrated to give 26 mg of crude material. After silica gel column purification with 10% ethyl acetate in hexane, 19 mg of a colorless oil of the title compound was obtained. $^1$H NMR (CDCl$_3$) δ6.92 (s, 1H), 6.89 (s, 1H), 4.48 (s, 1H), 3.1–3.3 (m, 4H), 3.11 (s, 3H), 2.32 (s, 3H), 2.28 (s, 3H), 2.20 (s, 3H), 2.19 (s, 3H), 1.45 (s, 3H), 1.44 (s, 3H), 1.4–1.52 (m, 2H), 1.2–1.4 (m, 2H), 1.10 (t, 3H), 0.90 (t, 3H) ppm.

EXAMPLE 23

4-(Butyl-ethyl-amino)-2-methyl-7-(2,4,6-trimethylphenyl)-7H-pyrrolo[2,3-d]pyrimidine-5,6-dione To a solution of 4-(butyl-ethyl-amino)-2-methyl-7-(2,4,6-trimethyphenyl)-5,7-dihydro-pyrrolo[2,3-d]pyrimidin-6-one (76 mg, 0.207 mmol), POCl$_3$ (0.039 ml, 0.415 mmol), triethylamine (0.059 ml), and dimethylamine (1 ml) in 2 ml acetonitrile was heated at reflux for 1 hour. The mixture was quenched with water and extracted with ethyl acetate. The organic layer was dried and concentrated to give a brown form (105 mg). After silica gel column chromatography, the title compound was isolated as a yellow glass (10 mg). $^1$H NMR (CDCl$_3$) δ7.00 (s, 2H), 3.954–15 (m, 2H), 3.65–3.85 (m, 2H), 2.38 (s, 3H), 2.32 (s, 3H), 2.10 (s, 6H), 1.55–1.75 (m, 2H), 1.35–1.55 (m, 2H), 1.25 (t, 3H), 1.00 (t, 3H) ppm.

EXAMPLE 24

N-Butyl-N-ethyl-2,5,N'-trimethyl-N'-(2,4,6-trimethylphenyl)-pyrimidine-4,6-diamine A mixture of(6-chloro-2,5-dimethyl-pyrimidin-4-yl)-methyl-(2,4,6-trimethylphenyl)-amine (200 mg) and N-butyl-ethylamine (0.3 ml) in 1 ml of DMSO was heated in oil bath of 160° C. for 15 hours. The mixture was quenched with water and extracted with ethyl acetate. The organic layer was separated, dried and concentrated to give the crude material. After silica gel column purification using chloroform as eluent, the title compound was obtained as an oil. $^1$H NMR (CDCl$_3$) δ6.83 (s, 2H), 3.22 (s, 3H), 3.12 (m, 4H), 2.44 (s, 3H), 2.26 (s, 3H), 2.01 (s, 6H), 1.35–1.42 (m, 2H), 1.1–1.25(m, 2H), 1.00 (t, 3H), 0.90 (t, 3H) ppm.

EXAMPLE 25

[2,5-Dimethyl-6-(tetrahydrofuran-3-yloxy)-pyrimidin-4-yl]-(2,4,6-trimethylphenyl)-amine A mixture of 3-hydroxy-tetrahydrofuran (0.5 ml) and sodium hydride (60% in oil, 53 mg, 1.33 mmol) in dry THF was stirred at room temperature for 5 minutes, (6-chloro-2,5-dimethyl-pyrimidin-4-yl)-(2,4,6-trimethylphenyl)-amine (107 mg, 0.388 mmol) was added. The mixture was heated at reflux for 15 hours. The mixture was quenched with water and extracted with ethyl acetate. The organic layer was separated, dried and concentrated to give a yellow oil. The oil was purified through silica gel column chromatography using 20% ethyl acetate in hexane as eluent to give 48 mg of the title compound as off-white crystals, mp 126–128° C. $^1$H NMR (CDCl$_3$) δ6.89 (s, 2H), 5.60 (brs, 2H), 3.8–4.0 (m, 4H), 2.27 (s, 6H), 2.13 (s, 6H), 2.1–2.25 (m, 2H), 1.93 (s, 3H) ppm.

EXAMPLE 26

2-(S)-[2,5-Dimethyl-6-(2,4,6-trimethylphenoxy)-pyrimidin-4-ylamino]-butan-ol

A mixture of 4-chloro-2,6-dimethyl-6-(2,4,6-trimethylphenyoxy)-pyrimidine (30 mg) and 2-(S)-amino-1-butanol (0.5 ml) in 0.5 ml of DMSO was heated at 130° C. for 4 hours. The mixture was quenched with water and extracted with ethyl acetate. The organic layer was separated, dried and concentrated to give a crude material. The crude residue was purified through silica gel column chromatography to give 24 mg of the title compound as white crystals. High MS for (C$_{19}$H$_{27}$N$_3$O$_2$) calc. 329.2103, found 329.21249; IR(KBr) 3400, 2940,1580 cm$^{-1}$; $^1$H NMR (CDCl$_3$) δ6.841 (s, 2H), 5.72 (brs, 1H), 4.45 (d, 1H), 3.82–3.96 (m, 1H), 3.72–3.9 (m, 1H), 3.5–3.6 (m, 1H), 2.27 (s, 3H), 2.21 (s, 3H), 2.08 (s, 3H), 2.02 (s, 6H), 1.4–1.7 (m, 2H), 1.03 (t, 3H) ppm.

EXAMPLE 27

4-(1-Ethyl-propoxy)-2,5-dimethyl-6-(2.4.6-trimethylphenoxy)-pyrimidine

A mixture of 3-pentanol (0.3 ml) and sodium hydride (60% in oil, 32 mg, 0.81 mmol) in DMSO was stirred at room temperature for 5 minutes. 4—Chloro-2,5-dimethyl-6-(2,4,6-trimethylphenyoxy)-pyrimidine (150 mg, 0.54 mmol) was added and the resulting mixture was heated at 150° C. for 5 hours. The mixture was quenched with water and extracted with ethyl acetate. The organic layer was separated, dried and concentrated to give a beige solid. The solid was purified through silica gel column chromatography using 20% chloroform in hexane as eluent to give the title compound as white crystals, mp 93.5–95.5° C. $^1$H NMR (CDCl$_3$) δ6.85 (s, 2H), 5.11 (t, 1H), 2.27 (s, 3H), 2.26 (s, 3H), 2.11 (s, 3H), 2.03 (s, 6H), 1.68 (p, 4H), 0.92 (t, 6H) ppm.

EXAMPLE 28

[[6-(Butyl-N-ethylamino)-2-methylpyrimidinyl]-(2,4,6-trimethylphenyl)-amino]-acetic acid ethyl ester A mixture of [(6-chloro-2-methylpyrimidin-4-yl)-(2,4,6-trimethylpheny)-amino]-acetic acid ethyl ester (85 mg, 0.244 mmol) and N-butyl-ethylamine (0.17 ml, 1.1 mmol) in 4 ml DMSO was heated at 135° C. for 15 hours. An additional 1 ml of N-butyl-ethylamine was added and the reaction was heated at that temperature for an additional 15 hours (tlc showed no starting material). The mixture was quenched with water and extracted with ethyl acetate. The organic layer was separated, dried and concentrated to give 123 mg of a light amber oil. The oil was purified through silica gel chromatotron using 5% ethyl acetate in hexane as eluent to give 92 mg (91%) of the title compound as a white glass. $^1$H NMR (CDCl$_3$) δ6.94 (s, 2H), 4.69 (s, 1H), 4.23 (s, 2H), 4.22 (q, 2H), 3.35 (q, 2H), 3.15 (t, 2H), 2.36 (s, 3H), 2.31 (s, 3H), 2.21 (s, 6H), 1.3–1.5 (m, 2H), 1.34 (t, 3H), 1.1–1.3 (m, 2H), 1.01 (t, 3H), 0.80 (t, 3H) ppm.

EXAMPLE 29

4-(1-Ethyl-propoxy)-3,6-dimethyl-2-(2,4,6-trimethyl-phenoxy)-pyridine

To a solution of 3-pentanol (0.2 ml, 0.5205 mol) in DMSO (1 ml) was added 60% sodium hydride in oil (30 mg) in a portionwise. After stirring at room temperature for 5 min, a solution of 4-chloro-2,5-dimethyl(2,4,6-trimethylphenoxy)-pyridine (98 mg) in 0.5 ml of dry THF was added and the resulting mixture was heated at 130° C. for 5 hours. The mixture was quenched with water and extracted with ethyl acetate. The organic layer was separated, dried and concentrated to give a yellow solid. The solid was purified through silica gel column chromatography using 20% chloroform in hexane to chloroform as eluent to give 7 mg of the title compound as white crystals, mp 72.5–74° C. $^1$H NMR (CDCl$_3$) δ6.84 (s, 2H), 6.26 (s, 1H), 4.16 (m, 1H), 2.27 (s, 3H), 2.17 (s, 6H), 2.04 (s, 6H), 1.69 (m, 4H), 0.95 (t, 6H) ppm.

The mesylate salt of 4-(1-ethyl-propoxy)-3,6-dimethyl-2-(2,4,6-trimethyl-phenoxy)-pyridine was prepared by addition of 1 equivalent of methanesulfonic acid in ethyl acetate. The white crystals formed from ethyl acetate. Mp 117–119° C.

EXAMPLE 30

[6-(Butyl-ethyl-amino)-2,5-dimethylpyrimidin-4-yl]-(2,4,6-trimethylphenyl)-acetonitrile A solution of mesitylacetonitrile (66 mg, 0.41 mmol) in 1 ml of DMSO was treated with NaH (60% in oil, 20 mg, 0.50 mmol) and stirred at room temperature for 20 minutes, butyl-(6-chloro-2,5-dimethylpyrimidin-4-yl)-ethylamine (100 mg, 0.414 mmol) was added and the resulting mixture was heated at 130° C. for 15 hours. The mixture was quenched with water and extracted with ethyl acetate. The organic layer was separated, dried and concentrated to give 160 mg of brown oil. The oil was purified through silica gel column chromatography using 5% ethyl acetate in hexane as eluent to give the title compound as a brown oil. $^1$H NMR (CDCl$_3$) δ 6.83 (s, 2H), 5.49 (s, $^1$H), 3.2–3.4 (m, 2H), 3.0–3.2 (m, 2H), 2.51 (s, 3H), 2.24 (s, 3H), 2.21 (s, 6H), 1.66 (s, 3H), 1.35–1.50 (m, 2H), 1.1–1.3 (m, 2H), 1.05 (t, 3H), 0.84 (t, 3H) ppm.

EXAMPLE 31

2-[6-(1-Ethyl-propoxy)-2,5-dimethylpyrimidin-4-yl]-2-(2,4,6-trimethylphenyl)-propionitrile To a solution of 3-pentanol (140 mg, 1.59 mmol) in 2 ml of dry THF was added sodium hydride (60% in oil, 38 mg) and the mixture was stirred at room temperature for 5 minutes. 2-(6—Choro-2,5-dimethylpyrimidin-4-yl)-2-(2,4,6-trimethylphenyl)-propionitrile (100 mg, 0.319 mmol) was added to the reaction mixture, and the resulting mixture was heated at reflux for 4 hours. The mixture was quenched with water and extracted with ethyl acetate. The organic layer was separated, dried and concentrated to give a brown oil (170 mg). The residue was purified through chromatotron using 20% ethyl cetate in hexane as eluent to give a mixture of two isomers as a yellow glass form and oth having a M+ of 365 from GC/Ms. $^1$H NMR (CDCl$_3$) δ6.8 and 6.76 (s, 2H), 4.08 and 3.96 (m, $^1$H), 3.25 and 3.22 (s, 3H), 2.36 and 2.30 (s, 3H), 2.21, 2.20 and 2.06 (s, total of 9H), 1.5–1.7 (m, 4H), 1.04 (s, 3H), 0.96 and 0.90 (t, 3H) ppm.

EXAMPLE 32

4-(1-Ethyl-propoxy)-2,5-dimethyl-6-(2,4,6-trimethyl-benzyl)-pyrimidine

The title compound was prepared by the method analogous to that in Example 32 starting with 4-Chloro-2,5-dimethyl-6-(2,4,6-trimethyl-benzyl)-pyrimidine and 3-pentanol. White crystals, mp. 82–84° C.

The title compounds of Example 33-39 were prepared by a method analogous to that of Example 27, starting with the appropriate 4-chloro-2-methyl-5-substituted 6-substituted-phenoxy)-pyrimidine and 3-pentanol.

EXAMPLE 33

4-(2,4-Dimethyl-phenoxy)-6-(1-ethyl-propoxy)-2,5-dimethyl-pyrimidine $^1$H NMR (CDCl$_3$) δ6.8–7.0 (m, 3H), 5.13 (m, 1H), 2.30 (s, 6H), 2.10 (s, 3H), 2.09 (s, 3H), 1.68 (m, 4H), 0.92 (t, 6H) ppm.

EXAMPLE 34

4-(2,6-Dimethyl-phenoxy)-6-(1-ethyl-propoxy)-2,5-dimethyl-pyrimidine $^1$H NMR (CDCl$_3$) δ7.04 (m, 3H), 5.12 (m, 1H), 2.25 (s, 3H), 2.13 (s, 3H), 2.07 (s, 6H), 1.66 (m, 4H), 0.92 (t, 6H) ppm.

EXAMPLE 35

4(1-Ethyl-propoxy)-2-methyl-6-(2,4,6-trimethyl-phenoxy)-pyrimidine-5-carbonitrile mp 128–130° C., $^1$H NMR (CDCl$_3$) δ6.8 (s, 2H), 5.18 (m, 1H), 2.30 (s, 3H), 2.21 (s,3H), 2.00 (s,6H), 1.4–1.58 (m, 4H), 0.90 (t, 6H) ppm.

EXAMPLE 36

5-tert-Butyl-4-(1-ethyl-propoxy)-2-methyl-6-(2,4,6-trimethyl-phenoxy)-pyrimidine $^1$H NMR (CDCl$_3$) δ6.85 (s, 2H), 5.25 (m, 1H), 2.29 (s, 3H), 2.20 (s, 3H), 2.03 (s, 6H), 1.65–1.80 (m, 4H), 1.52 (s, 9H), 0.90 (t, 6H) ppm.

EXAMPLE 37

4-(1-Ethyl-propoxy)-5-isopropyl-2-methyl-6-(2,4,6-trimethyl-phenoxy)-pyrimidine $^1$H NMR (CDCl$_3$) δ6.85 (s, 2H), 5.17 (m, 1H), 3.50 (m, 1H), 2.27 (s, 3H), 2.23 (s, 3H), 2.03 (s, 6H), 1.69 (m, 4H), 1.33 (s, 3H), 1.31 (s, 3H), 0.92 (t, 6H) ppm.

EXAMPLE 38

5-Bromo-4-(1-ethyl-propoxy)-2-methyl-6-(2,4,6-trimethyl-phenoxy)-pyrimidine $^1$H NMR (CDCl$_3$) δ6.86 (s, 2H), 5.16 (m, 1H), 2.29 (s, 3H), 2.28 (s, 3H), 2.06 (s, 6H), 1.65–1.80 (m, 4H), 1.52 (s, 9H), 0.95 (t, 6H) ppm.

EXAMPLE 39

5-Chloro-4-(1-ethyl-propoxy)-2-methyl-6-(2,4,6-trimethyl-phenoxy)-pyrimidine $^1$H NMR (CDCl$_3$) δ6.86 (s, 2H), 5.16 (m, 1H), 2.28 (s, 3H), 2.27 (s, 3H), 2.06 (s, 6H), 1.65–1.80 (m, 4H), 1.52 (s, 9H), 0.94 (t, 6H) ppm.

The title compounds of Examples 4041 were prepared by a method analogous to that described in Example 24, starting from 4-chloro-2,5-dimethyl-6-(2,4,6-trimethylphenoxy)-pyrimidine and the appropriate amine.

EXAMPLE 40

[2,5-Dimethyl-6-(2,4,6-trimethyl-phenoxy)-pyrimidin-4-yl (1-ethyl-propyl)-amine $^1$H NMR (CDCl$_3$) δ6.84 (s, 2H), 4.10 (m, 2H, NH and CH), 2.27 (s, 3H), 2.21 (s, 3H), 2.04 (s, 9H), 1.3–1.6 (m, 4H), 0.91 (t, 6H) ppm.

EXAMPLE 41

Butyl-[2,5-dimethyl-6-(2,4,6-trimethyl-phenoxy)-pyrimidin-4-yl]-ethyl-amine $^1$H NMR (CDCl$_3$) δ6.87 (s, 2H), 3.76 (m, 2H), 3.68 (t, 2H), 2.73 (s, 3H), 2.28 (s, 6H), 1.99 (s, 6H), 1.5–1.7 (m, 4H), 1.27 (t, 3H), 0.94 (t, 3H) ppm.

The title compounds of Examples 42-54 were prepared by a method analogous to that described in Example 29, starting with the appropriate 4-chloro-2-methyl-6-(substituted phenoxy or thiophenoxy)-pyridine and the appropriate alcohol.

EXAMPLE 42

2-(4-Bromo-2,6-dimethyl-phenoxy)-4-(1-ethyl-prpoxy)-3,6-dimethyl-pyridine $^1$H NMR (CDCl$_3$) δ7.18 (s, 2H), 6.30 (s, 1H), 4.22 (m, 1H), 2.20 (s, 6H), 2.05 (s, 6H), 1.73 (m, 4H), 1.00 (t, 6H) ppm.

EXAMPLE 43

2-(4-Chloro-2,6-dimethyl-phenoxy)-4-(1-ethyl-propoxy)-3,6-dimethyl-pyridine $^1$H NMR (CDCl$_3$) δ7.05 (s, 2H), 6.31 (s, 1H), 4.20 (m, 1H), 2.20 (s, 6H), 2.08 (s, 6H), 1.73 (m, 4H), 0.99 (t, 6H) ppm.

EXAMPLE 44

3-Ethyl-4-(1-ethyl-propoxy)-6-methyl-2-(2,4,6-trimethyl-phenoxy)-pyridine $^1$H NMR (CDCl$_3$) δ6.85 (s, 2H), 6.26 (s, 1H), 4.18 (m, 1H), 2.73(q,2H), 2.28 (s, 3H), 2.17 (s, 3H), 2.05 (s, 6H), (m, 4H), 1.18 (t, 3H), 0.96 (t, 6H) ppm.

EXAMPLE 45

4-(1-ethyl-propenyloxy)-3,6-dimethyl-2-(2,4,6-trimethyl-phenoxy)-pyridine (A mixture of cis and trans isomers)

$^1$H NMR (CDCl$_3$) δ6.85 (s, 2H), 6.30 (s, 0.3H), 6.21 (s, 0.7H), 5.10 (m, 0.7H), 4.95 (m, 0.3H), 2.27 (s, 3H), 2.24 (s, 2.1H), 2.19 (s, 0.9H), 2.14 (s, 3H), 2.05 (s, 6H), 1.65 (d, 0.9H), 1.50 (d, 2.1H), 1.08 (t, 1.8H), 1.05 (t, 4.2H) ppm.

EXAMPLE 46

Methanesulfonicacid salt of 4-(1-ethyl-propoxy)-2,3,5-trimethyl-6-(2,4,6-trimethyl-phenoxy)-pyridine Mp 58–60° C. $^1$H NMR (CDCl$_3$) δ6.90 (s, 2H), 4.20 (m, 1H), 2.70 (s, 3H), 2.61 (s, 3H), 2.28 (s, 3H), 2.16 (s, 3H), 2.08 (s, 6H), 1.5–1.8 (m, 4H), 0.96 (t, 6H) ppm.

EXAMPLE 47

4-(1-Ethyl-propoxy)-6-methyl-2-(2,4.6-trimethyl-phenoxy)-nicotinic acid methyl ester $^1$H NMR (CDCl$_3$) δ6.84 (s, 2H), 6.39 (s, 1H), 5.04 (m, 1H), 3.85 (s, 3H), 2.27 (s, 3H), 2.23 (s, 3H), 2.05 (s, 6H), 1.5–1.7 (m, 4H), 0.95 (s, 6H) ppm.

EXAMPLE 48

4-(1-Ethyl-propoxy)-2-methyl-6-(2,4,6-trimethyl-phenoxy)-pyridine $^1$H NMR (CDCl$_3$) δ6.90 (s, 2H), 6.34 (d, J=2 Hz, 1H), 5.70 (d, J=2 Hz, $_1$H), 4.05 (m, 1H), 2.40 (s, 3H), 2.30 (s, 3H), 2.11 (s, 6H), 1.62 (m, 4H), 0.89 (t, 6H) ppm.

EXAMPLE 49

3,6-Dimethyl-4-(tetrahydro-furan-3-yloxy)-2-(2,4,6-trimethyl-phenoxy)-pyridine $^1$H NMR (CDCl$_3$) δ6.88 (s, 2H), 6.25 (s, 1H), 4.99 (m, 1H), 3.9–4.1 (m, 4H), 2.31 (s, 3H), 2.23 (s, 3H), 2.20 (s, 3H), 2.1–2.3 (m, 2H), 2.07 (s, 6H) ppm.

EXAMPLE 50

4-(1-Methoxymethyl-propoxy)-3.6-dimethyl-2-(2,4,6-trimethyl-phenoxy)-Pyridine $^1$H NMR (CDCl$_3$) δ6.88 (s, 2H), 6.38 (s, 1H), 4.42 (m, 1H), 3.5–3.7 (m, 2H), 3.42 (s, 3H), 2.31 (s, 3H), 2.21 (s, 6H), 2.07 (s, 6H), 1.7–1.85 (m, 2H), 1.02 (t, 3H) ppm.

EXAMPLE 51

3-[3,6-Dimethyl-2-(2,4,6-trimethyl-phenoxy)-pyridin-4-yloxy]-pentan-2-ol $^1$H NMR (CDCl$_3$) δ6.88 (s, 2H), 6.34 (s, 1H), 4.25–4.45 (m, 1 HO, 3.6–3.8 (m,$^1$H), 2.30 (s, 3H)2.21 (s, 3H), 2.20 (s, 3H), 2.06 (s, 6H), 1.2–1.4 (m, 5HO, 1.07 (t, 3H) ppm.

EXAMPLE 52

4-sec-Butoxy-3,6-dimethyl-2-(2,4,6-trimethyl-phenoxy)-pyridine $^1$H NMR (CDCl$_3$) δ6.88 (s, 2H), 6.31 (s, 1H), 4.35 (m, 1H), 2.30 (s, 3H), 2.21 (s, 3H), 2.19 (s, 3H), 2.07 (s, 6H0, 1.7–1.9 (m, 2H), 1.34 (d, 3H), 1.01 (t, 3H) ppm.

EXAMPLE 53

2-(2,4-Dimethyl-phenylsulfanyl)-4-(1-ethyl-propoxy)-3,6-dimethyl-pyridine

Golden oil. $^1$H NMR (CDCl$_3$) δ7.19 (d, j=8 Hz,1HO, 7.06 (s, 1H), 6.94 (d, J=8Hz,1H), 6.42 (s, 1H), 4.19 (m, 1H), 2.34 (s, 3H), 2.33 (s, 3H), 2.32 (s, 3H), 2.18 (s, 3H), 1.69 (m, 4H), 0.95 (t, 6H) ppm.

EXAMPLE 54

4-(1-Ethyl-propoxy)-3,6-dimethyl-2-(2,4,6-trimethyl-phenylsulfanyl)-pyridine $^1$H NMR (CDCl$_3$) δ6.97 (s, 2H), 6.30 (s, 1H), 4.15 (m, 1H), 2.35 (s, 3H), 2.30 (s, 3H), 2.23 (s, 3H), 2.20 (s, 3H), 1.68 (m, 4H), 0.95 (t, 6H) ppm.

EXAMPLE 55

2-(4-Ethyl-2,6-dimethyl-phenoxy)-4-(1-ethyl-propoxy)-3,6-dimethyl-pyridine

To a solution of 2.5 N n-BuLi in hexane (0.47 ml, 1.18 mmol) in 5ml of dry THF was added a solution of 2-(4-bromo-2,6-dimethyl-phenoxy)-4-(1-ethyl-prpoxy)-3,6- dimethyl-pyridine (465 mg, 1.18 mmol) in 5 ml of dry THF at −78° C. After stirring at that temperature for 5 min, an excess of ethyl iodide (0.4 ml) was added and the resulting mixture was stirred at −78° C. for 30 min, then at 0° C. for 15 min. The mixture was quenched with saturated ammonium chloride and extracted with ethyl acetate. The organic layer was dried and concentrated to give a light brown oil The oil was purified through silica gel column chromatography using chloroform as eluent to give 260 mg of the title compound as white solid. $^1$H NMR (CDCl$_3$) δ6.90 (s, 2H), 6.38 (s, 1H), 4.20 (m, 1H), 2.61(q,2H), 2.24 (s, 3H), 2.21 (s, 3H), 2.10 (s, 6H), 1.70 (m, 4H), 1.30 (t, 3H), 0.98 (t, 6H) ppm.

The title compounds of Examples 56-62 were prepared by a method analogous to that described in Example 55, starting from n-BuU and 2-(4-bromo-2,6-dimethyl-phenoxy)-4-(1-ethyl-prpoxy)-3,6-dimethyl-pyridine, followed by quenching with an appropriate electrophile.

EXAMPLE 56

4-[4-(1-Ethyl-propoxy)-3,6-dimethyl-pyridin-2-yloxy]-3,5-dimethyl-benzaldehyde $^1$H NMR (CDCl$_3$) δ9.94 (s, 1H), 7.61 (s, 2H), 6.32 (s, 1H), 4.20 (m, 1H), 2.21 (s, 3H), 2.16 (s, 9H)1.70 (m, 4H), 0.98 (t, 6H) ppm.

EXAMPLE 57

2-(2,6-Dimethyl-4-propyl-phenoxy)4-(1-ethyl-propoxy)-3,6-dimethyl-pyridine $^1$H NMR (CDCl$_3$) δ6.88 (s, 2H), 6.30 (s, 1H), 4.20 (m, 1H), 2.54(dd,2H), 2.22 (s, 3H), 2.20 (s, 3H), 2.09 (s, 6H), 1.6–1.8 (m, 6H), 0.9–1.1 (m, 9H) ppm.

EXAMPLE 58

2-(2,6-Dimethyl-phenoxy)4-(1-ethyl-propoxy)-3,6-dimethyl-pyridine $^1$H NMR (CDCl$_3$) δ7.06 (m, 3H), 6.30 (s, 1H), 4.20 (m, 1H), 2.21 (s, 6H), 2.11 (s, 6H), 1.73 (m, 4H), 0.99 (t, 6H) ppm.

EXAMPLE 59

2{4-[4-(1-Ethyl-propoxy)-3,6-dimethyl-pyridin-2-yloxy]-3,5-dimethyl-phenyl}-propan-2-ol $^1$H NMR (CDCl$_3$) δ7.15 (s, 2H), 6.25 (s, 1H), 4.20 (m, 1H), 2.20 (s, 3H), 2.19 (s, 3H), 2.10 (s, 6H), 1.85 (brs, $^1$H),1.70 (m, 4H), 1.60 (s, 6H), 0.95 (t, 6H) ppm.

EXAMPLE 60

4-(1-Ethyl-propoxy)-2-(4-iodo-2,6-dimethyl-phenoxy)-3,6-dimethyl-pyridine $^1$H NMR (CDCl$_3$) δ7.39 (s, 2H), 6.30 (s, 1H), 4.19 (m, 1H), 2.20 (s, 3H), 2.18 (s, 3H), 2.05 (s, 6H), 1.72 (m, 4H), 0.98 (t, 6H) ppm.

EXAMPLE 61

4-[4-(1-Ethyl-propoxy)-3,6-dimethyl-pyridin-2-yloxy]-3,5-dimethyl-phenol $^1$H NMR (CDCl$_3$) δ7.85 (brs, 1H), 6.36 (s, 1H), 6.24 (s, 2H), 4.24 (m,1H), 2.39 (s, 3H), 2.20 (s, 3H), 2.02 (s, 6H), 1.74 (m, 4H), 1.00 (t, 6H) ppm.

EXAMPLE 62

1-{4-[4-(1-Ethyl-propoxy)-3,6-dimethyl-pyridin-2-yloxy]-3,5-dimethyl-phenyl}-pyrrolidin-2-one $^1$H NMR (CDCl$_3$) δ7.30 (s, 2H), 6.30 (s, 1H), 4.20 (m, 1H), 3.88 (t, 2H), 2.61 (t, 2H) ppm.

EXAMPLE 63

{4-[4-(1-Ethyl-propoxy)-3,6-dimethyl-pyridin-2-yloxy]-3,5-dimethyl-phenyl}-methanol A mixture of 4-[4-(1-ethyl-propoxy)-3,6-dimethyl-pyridin-2-yloxy]-3,5-dimethyl-benzaldehyde (114 mg, 0.41 mmol) and sodium borohydride (63 mg, 1.6 mmol) in 3 ml of methanol was stirred at room temperature for 2 hours. The reaction mixture was quenched with water and extracted with ethyl acetate. The organic layer was dried and concentrated to give yellow oil. The oil was purified through silica gel using chloroform as eluent to give 70 mg of the title compound as a colorless oil. $^1$H NMR (CDCl$_3$) δ7.04 (s, 2H), 6.32 (s,1H), 4.55 (s, 2H), 4.21 (m, 1H), 2.30 (brs, 1H), 2.22 (s, 3H), 2.21 (s, 3H), 2.12 (s, 6H), 1.73 (m, 4H), 0.91 (t, 6H) ppm.

EXAMPLE 64

4-(1-Ethyl-propoxy)-2-(4-methoxy-2,6-dimethyl-phenoxy)-3,6-dimethyl-pyridine

To a solution of 4-[4-(1-ethyl-propoxy)-3,6-dimethyl-pyridin-2-yloxy]-3,5-dimethyl-phenol (40 mg, 0.12mmol) in 3 ml of dry THF was added 10 mg of 60% sodium hydride in oil at room temperature. After stirring for 5 min, 0.3 ml of methyl iodide was added and the resulting mixture was stirred at room temperature overnight. The mixture was quenched with water and extracted with ethyl acetate. The organic layer was dried and concentrated to give a yellow solid. The solid was purified through silica gel column chromatography using hexane to 1:1 chloroform:hexane as eluent to yield 20 mg of the title compound as yellow solid. $^1$H NMR (CDCl$_3$) δ6.66 (s, 2H), 6.28 (s, 1H), 4.20 (m, 1H), 3.79 (s, 3H), 2.20 (s, 3H), 2.19 (s, 3H0, 2.08 (s, 6H), 1.71 (m, 4H), 0.97 (t, 6H) ppm.

EXAMPLE 65

4-(1-Ethyl-propoxy)-2-(4-isopropoxy-2.6-dimethyl-phenoxy)-3,6-dimethyl-pyridine

To a solution of 4-[4-(1-ethyl-propoxy)-3,6-dimethyl-pyridin-2-yloxy]-3,5-dimethyl-phenol (58 mg, 0.176 mmol) in 3 ml of dry THF was added triphenylphosphine (70 mg, 0.264 mmol) and isopropanol (60 mg, 0.22 mmol). The resulting mixture was stirred at room temperature for 5 min, diethyl azodicarboxylate (46 mg, 0.264 mmol) was added. The mixture was stirred at room temperature overnight. An additional 20 mg of diethyl azodicarboxylate was added and the mixture was stirred for an additional 4 hours. The mixture was quenched with water and extracted with methylene chloride. The organic layer was dried and concentrated to give an oil. The oil residue was purified through silica gel column chromatography using 1:1 hexane:chloroform to 1:2 hexane: chloroform as eluent to give 38 mg (58%) of the title compound as a colorless oil. $^1$H NMR (CDCl$_3$) δ6.60 (s, 2H), 6.28 (s, 1H), 4.50 (m, 1H), 4.18 (m, 1H), 2.20 (s, 3H), 2.19 (s, 3H), 2.079s,6H), 1.71 (m, 4H), 1.34 (d, 6H), 0.98 (t, 6H) ppm.

The title compounds of Examples 66-67 were prepared by a method analogous to that described in Example 64, starting with an appropriate pyridine-3,6 dimethylphenol or pyridine-3,5-dimethyl-phenyl methanol with a base, followed by quenching with an appropriate alkyl halide.

EXAMPLE 66

2-(4-Ethoxy-2,6-dimethyl-phenoxy)4-(1-ethyl-propoxy)-3.6-dimethyl-pyridine $^1$H NMR (CDCl$_3$) δ6.60 (s, 2H), 6.28 (s, 1H), 4.19 (m, 1H), 3.99(q,2H), 2.19 (s, 3H), 2.18 (s, 3H), 2.07 (s, 6H), 1.74 (m, 4H), 1.40 (t, 3H), 0.97 (t, 6H) ppm.

EXAMPLE 67

4-(1-Ethyl-propoxy)-2-(4-methoxymethyl-2,6-dimethyl-phenoxy)-3,6-dimethyl-pyridine Mp 58–60° C. $^1$H NMR (CDCl$_3$) δ7.05 (s, 2H), 6.30 (s, 11H), 4.41 (s, 2H), 4.19 (m, 1H), 3.42 (s, 3H), 2.21 (s, 3H), 2.18 (s, 3H), 2.11 (s, 6H), 1.72 (m, 4H), 0.98 (s, 6H) ppm.

EXAMPLE 68

[3,6-Dimethyl-2-(2,4,6-trimethyl-phenoxy)-pyridin-4-yl]-ethyl-amine

A mixture of 4-chloro-3,6-dimethyl-2-(2,4,6-trimethylphenoxy)-pyridine (1.330 g, 4.822 mmol) and 20 ml of ethyl amine in 13 ml of 1-methyl-2-pyrrolidinone was heated at 150° C. at 250 psi overnight in a pressure reactor. The reaction was heated an additional 24 hours at 175° C. and 300 psi. The reaction mixture cooled to room temperature and diluted with water and extracted with ethyl acetate. The organic layer was dried and concentrated to give a brown oil. The oil residue was purified through silica gel column chromatography using chloroform to 2% methanol in chloroform as eluent to give 0.820 g (60%) of the title compound as a white solid, mp 115–116° C.

$^1$H NMR (CDCl$_3$) δ6.87 (s, 2H), 6.11 (s, 1H), 3.85 (t, 1H), 3.24 (m, 2H), 2.30 (s, 3H), 2.17 (s, 3H), 2.13 (s, 3H), 2.08 (s, 6H), 1.32 (t, 3H) ppm.

The title compounds of Examples 69–71 were prepared by the method analogous to that described in Example 68 starting with an appropriate 4-chloro-2-substituted phenoxy-pyridine and an appropriate amine.

EXAMPLE 69

[3,6-Dimethyl-2-(2,4,6-trimethyl-phenylsulfanyl)-Dyridinyl]-(1-ethyl-propyl)-amine Mp 108–110° C. $^1$H NMR (CDCl$_3$) δ6.95 (s, 2H), 6.09 (s, 1H), 3.63 (d, 1H), 3.28 (m, 1H), 2.36 (s, 6H), 2.30 (s, 3H), 2.17 (s, 3H), 2.11 (s, 3H), 1.4–1.75 (m, 4H0, 0.93 (t, 6H) ppm. The hydrogen chloride salt, mp 148–150° C.; $^1$H NMR (CDCl$_3$) δ6.95 (s, 2H), 6.30 (s, 1H), 5.75 (d, $^1$H), 3.38 (m, 1H), 2.69 (s, 3H), 2.33 (s, 6H), 2.28 (s, 3H0, 2.02 (s, 3H), 1.72 (m, 4H), 0.93 (t, 6H) ppm.

EXAMPLE 70

2-(4-Chloro-2,6-dimethyl-phenoxy)-3,6-dimethyl-pyridin-4-yl]-ethyl-amine; white solid $^1$H NMR (CDCl$_3$) δ7.04 (s, 2H), 6.13 (s, 1H), 3.88 (t, 1H), 3.24 (m, 2H), 2.17 (s, 3H), 2.17 (s, 3H), 2.08 (s, 6H), 1.32 (t, 3H) ppm.

EXAMPLE 71

[3,6-dimethyl-2-(2,4,6-trimethyl-phenylsulfanyl)-pyridin-4-yl]-ethyl-amine

Tan crystals, mp 114–116° C. $^1$H NMR (CDCl$_3$) δ6.94 (s, 2H), 6.12 (s, 1H), 3.76 (t, 1H), 3.21 (m, 2H), 2.35 (s, 6H), 2.30 (s, 3H), 2.19 (s, 3H), 2.10 (s, 3H), 1.29 (t, 3H) ppm.

EXAMPLE 72

[3,6-Dimethyl-2-(2,4,6-trimethyl-phenoxy)-pyridin-4-yl]-ethyl-propyl-amine

To a solution of [3,6-dimethyl-2-(2,4,6-trimethyl-phenoxy)-pyridin-4yl]-ethyl-amine (7.00 g, 24.6 mmol) in 100 ml of dry THF was added 1.0 M lithium bis (trimethylsilyl)amide in hexane (32 ml, 32 mmol) at –78° C. After stirring at that temperature for 10 min, the reaction mixture was treated with iodopropane (13 ml, 125 mmol) at –70° C. After stirring at that temperature for 20 min, the dry ice bath was removed and the reaction mixture was stirred at room temperature for 3 hours. The reaction mixture was quenched with water and extracted with ethyl acetate. The organic layer was dried and concentrated to give an oil. The oil residue was purified through silica gel column chromatography using 1:1 chloroform:hexane to chloroform as eluent to give 5.04 g (62.5%) of [3,6-dimethyl-2-(2,4,6-trimethyl-phenoxy)-pyridin-4-yl]-ethyl-propyl-amine as yellow solid; $^1$H NMR (CDCl$_3$) δ6.88 (s, 2H), 6.41 (s, 1H), 3.11(q,2H), 3.03(dd,2H), 2.30 (s, 3H), 2.25 (s, 3H), 2.19 (s, 3H), 2.07 (s, 6H), 1.55 (m, 2H), 1.08 (t, 3H), 0.90 (t, 3H) ppm. The corresponding HCl salt, white crystals; mp 167–169° C.; $^1$H NMR (MeOH-d4) δ7.00 (s, 2H), 6.75 (s, 1H), 3.54(q,2H), 3.43 (t, 2H), 2.35 (s, 3H), 2.31 (s, 3H), 2.27 (s, 3H), 2.08 (s, 6H), 1.69 (m, 2H), 1.25 (t, 3H0, 0.94 (t, 3H) ppm;

The title compounds of Examples 73–79 were prepared by the method analogous to that described in Example 72 starting with an appropriate 2-(substituted phenoxy or thiophenoxy)-pyridin4-yl-ethyl amine and a base (lithium bis(trimethylsilyl)amide or lithium diisopropylamide), followed by quenching with an appropriate alkyl halide.

EXAMPLE 73

[3,6-dimethyl-2-(2,4,6-trimethyl-phenoxy)-pyridin-4-yl]-diethyl-amine $^1$H NMR (CDCl$_3$) δ6.87 (s, 2H), 6.40 (s, 1H), 3.10(q,4H), 2.30 (s, 3H), 2.24 (s, 3H), 2.19 (s, 3H), 2.06 (s, 6H), 1.08 (t, 6H) ppm. The HCl salt, white crystals, mp 180–181° C.; $^1$H NMR (CD$_3$OD) δ7.01 (s, 2H), 6.78 (s, 1H), 3.58(q,4H), 2.38 (s, 3H), 2.32 (s, 6H), 2.10 (s, 6H), 1.28 (t, 6H) ppm.

EXAMPLE 74

[3,6-Dimethyl-2-(2,4,6-trimethyl-phenoxy)-pyridin-4-yl]-ethyl-methyl-amine $^1$H NMR (CDCl$_3$) δ6.86 (s, 2H), 6.38 (s, 1H), 3.05(q,2H), 2.75 (s, 3H), 2.29 (s, 3H), 2.25 (s, 3H), 2.18 (s, 3H), 2.06 (s, 6H), 1.18 (t, 3H) ppm. The HCl salt, mp 173–174° C.

EXAMPLE 75

Butyl-[3,6-dimethyl-2-(2,4,6-trimethyl-phenoxy)-pyridin-4-yl]-ethyl-amine $^1$H NMR (CDCl$_3$) δ6.88 (s, 2H), 6.41 (s, 1H), 3.0–3.3 (m, 4H), 2.31 (s, 3H), 2.25 (s, 3H), 2.19 (s, 3H), 2.08 (s, 6H), 1.3–1.6 (m, 4H), 1.09 (t, 3H), 0.93 (t, 3H) ppm.

EXAMPLE 76

Butyl-[2-(4-chloro-2,6-dimethyl-phenoxy)-3,6-dimethyl-pyridin-4-yl]-ethyl-amine $^1$H NMR (CDCl$_3$) δ7.03 (s, 2H), 6.39 (s, 1H), 3.09(q,2H), 3.01(dd,2H), 2.21 (s, 3H), 2.16 (s, 3H), 2.05 (s, 6H), 1.4–1.6

(m, 2H), 1.25–1.40 (m, 2H), 1.06 (t, 3H), 0.87 (t, 3H) ppm. The HCl salt, mp 177–178° C.; ¹H NMR(DMSO-d6) δ7.20 (s, 2H), 6.74 (s, 1H), 3.1–3.4 (m, 4H), 2.24 (s, 3H), 2.17 (s, 3H), 2.00 (s, 6H), 1.4–1.6 (m, 2H), 1.25–1.40 (m, 2H), 1.05 (t, 3H), 0.86 (t, 3H) ppm.

EXAMPLE 77

[2-(chloro-2,6-dimethyl-phenoxy)-3,6-dimethyl-pyridin-4-yl]-ethyl-propyl-amine

¹H NMR (CDCl₃) δ7.04 (s, 2H), 6.41 (s, 1H), 3.11(q,2H), 3.00 (m, 2H), 2.24 (s, 3H), 2.17 (s, 3H), 2.07 (s, 6H), 1.54 (m, 2H), 1.08 (t, 3H), 0.90 (t, 3H) ppm. The HCl salt, white crystals, mp 74–76° C. ¹H NMR(CD3OD) δ7.23 (s, 2H), 6.81 (s, 1H), 3.58(q,2H), 3.46 (m, 2H), 2.38 (s, 3H), 2.31 (s, 3H), 2.13 (s, 6H), 1.6–1.8 (m, 2H), 1.26 (t, 3H), 0.96 (t, 3H) ppm.

EXAMPLE 78

[2-(4-chloro-2,6-dimethyl-phenoxy)-3,6-dimethyl-pyridin-4-yl]-diethyl-amine

¹H NMR (CDCl₃) δ7.05 (s, 2H), 6.41 (s, 1H), 3.11(q,4H), 2.24 (s, 3H), 2.18 (s, 3H), 2.07 (s, 6H), 1.09 (t, 6H) ppm. The HCl salt, white crystals, mp 184–185° C. ¹H NMR(CD3OD) δ7.23 (s, 2H), 6.81 (s, 1H), 3.56(q,4H), 2.37 (s, 3H), 2.33 (s, 3H), 2.12 (s, 6H), 1.26 (t, 6H) ppm.

EXAMPLE 79

[3,6-Dimethyl-[2-(2,4,6-trimethyl-phenylsulfanyl)-pyridin-4-yl]-ethyl-propyl-amine ¹H NMR (CDCl₃) δ6.95 (s, 2H), 6.45 (s, 1H), 3.02 (q,2H), 2.97 (dd,2H), 2.35 (s, 6H), 2.31 (s, 3H), 2.21 (s, 3H), 2.20 (s, 3H), 1.49 (m, 2H), 1.02 (t, 3H), 0.86 (t, 3H) ppm. The HCl salt, white crystals, mp 110–112° C.; ¹H NMR (CDCl₃) δ6.92 (s, 2H), 6.51 (s, 1H), 3.27 (q,2H), 3.19 (dd,2H), 284 (s, 3H), 2.32 (s, 6H), 2.28 (s, 3H), 1.82 (s, 3H), 1.52 (m, 2H), 1.15 (t, 3H), 0.84 (t, 3H) ppm.

EXAMPLE 80

N-[3,6-Dimethyl-2-(2,4,6-trimethyl-phenoxy)-pyridin-4-yl]-N-ethyl-2,2,2-trifluoro-acetamide To a solution of [3,6-dimethyl-2-(2,4,6-trimethyl-phenoxy)-pyridin-4-yl]-ethylamine (200 mg, 0.7 mmol) in dry methylene chloride was added triethylamine (0.1 ml, 0.73 mmol) and trifluoroacetic anhydride (0.11 ml, 0.74 mmol) and stirred at room temperature for 2 hours. The reaction mixture was quenched with water and extracted with ethyl acetate. The organic layer was dried and concentrated to give the crude material. The crude material was purified through silica gel column chromatography using 25% hexane in chlorofor as eluent to give 225 mg (83%) of the title compound as white crystals, mp 110–111° C., ¹H NMR (CDCl₃) δ6.91 (s, 2H), 6.57 (s, 1H), 4.16 (m, 1H), 3.39 (m, 1H), 2.32 (s, 3H), 2.27 (s, 3H), 2.24 (s, 3H), 2.07 (s, 3H), 2.05 (s, 3H), 1.26 (t, 3H) ppm.

EXAMPLE 81

3,6-Dimethyl-2-(2,4,6-trimethyl-phenoxy)-pyridin-4-yl]-ethyl-(2,2,2-trifluoro-ethyl)-amine To a solution of N-[3,6-Dimethyl-2-(2,4,6-trimethyl-phenoxy)-pyridin-4-yl]-N-ethyl-2,2,2-trifluoro-acetamide (292 mg, 0.77 mmol) in 15 ml of dry THF was added 2M BH₃.DMS in THF (0.96 ml, 1.92 mmol) at room temperature. The resulting mixture was heated at reflux overnight. The mixture was quenched with water and extracted with ethyl acetate. The organic layer was dried and concentrated to give 300 mg of white solid. The solid was recrystallized from hexane and 2 drops of methanol to give white crystals (298 mg, 96%). ¹H NMR (CDCl₃) 66.85 (s, 2H), 6.47 (s, 1H), 3.70 (q,2H), 3.25 (q,2H), 2.32 (s, 3H), 2.27 (s, 3H), 2.20 (s, 3H), 2.05 (s, 3H), 1.13 (t, 3H) ppm. The HCl salt, white crystals, mp 73–74° C. ¹H NMR(CD₃OD) δ6.97 (s, 1H), 6.96 (s, 2H), 4.09 (q,2H), 3.46 (q,2H), 2.34 (s, 3H), 2.30 (s, 3H), 2.28 (s, 3H), 2.05 (s, 6H), 1.17 (t, 3H) ppm.

EXAMPLE 82

4-(1-Ethyl-propylamino)-methyl-2-(2,4,6-trimethyl-phenoxy)-nicotinic acid methyl ester A mixture of 4-chloro-6-methyl-2-(2,4,6-trimethyl-phenoxy)-nicotinic acid methyl ester (500 mg, 1.56 mmol) and 1-ethyl-propyl-amine (0.8 ml) in 1 ml of DMSO was heated at reflux for 15 hours. The mixture was quenched with sat. ammonium chloride and extracted with ethyl acetate. The organic layer was dried and concentrated to give 445.6 mg of yellow solid. The solid was purified through silica gel column chromatography using 1:1 ratio of chloroform:hexane as eluent to give (289 mg, 50%)of the title compound as white crystals, mp 98–102° C.; ¹H NMR (CDCl₃) δ8.04 (d, 1H), 6.85 (s, 2H), 6.06 (s, 1H), 3.85 (s, 3H), 3.32 (m, 1H), 2.28 (s, 3H), 2.10 (s, 3H), 2.07 (s, 3H), 1.62 (m, 4H), 0.95 (t, 6H) ppm.

EXAMPLE 83

4-(1-Ethyl-propylamino)-6-methyl-2-(2,4,6-trimethyl-phenoxy)-pyridin-3-yl]-methanol A mixture of 4-(1-ethyl-propylamino)-methyl-2-(2,4,6trimethyl-phenoxy)-nicotinic acid methyl ester (220 mg, 0.594 mmol) and 1 M lithium aluminum hydride in THF (4 ml, 4 mmol) in dry THF (3 ml) was heated at reflux for 10 min, then stirred at rt overnight. The mixture was quenched with 0.3 ml of water, 0.3 ml of 2N NaOH, then 0.8 ml of water and stirred at room temperature for 10 min. White solid formed and was filtered through celite. The filtrate was concentrate to dryness to give 207 mg (100%) of the title compound as white solid. ¹H NMR (CDCl₃) δ6.83 (s, 2H), 6.06 (s, 1H), 4.96 (d, 1H,NH), 4.88 (d, 2H), 3.28 (m, 1H), 2.26 (s, 3H), 2.11 (s, 3H), 2.04 (s, 6H), 1.4–1.6 (m, 4H), 1.4 (t, ₁H,OH), 0.93 (t, 6H) ppm.

EXAMPLE 84

4-(1-Ethyl-propylamino)-6-methyl-2-(2.4.6-trimethyl-phenoxy)-nicotinic acid

A mixture of 4-(1-Ethyl-propylamino)+methyl-2-(2,4,6trimethyl-phenoxy)-nicotinic acid methyl ester (16 mg, 0.043 mmol) and lithium hydroxide (30 mg) in dioxane (1 ml) and water (1 ml) was stirred at rt over night. The mixture wa squenched with water and adjusted to pH 7.0 and extracted with chloroform. The organic layer was dried and concentrated to give the crude material. The crude material was purified through silica gel column chromatography using 10% ethyl acetate in chloroform as eluent to give 7 mg of the title compound as white solid. ¹H NMR (CDCl₃) 69.12 (d, 1H), 6.87 (s, 2H), 6.16 (s, 1H), 3.35 (m, 1H), 2.29 (s, 3H), 2.10 (s, 3H), 2.07 (s, 6H), 1.4–1.6 (m, 4H), 0.94 (t, 6H) ppm.

EXAMPLE 85

[3-Chloromethyl-6-methyl-2-(2,4,6-trimethyl-phenoxy)-pyridin 4-yl]-(1-ethyl-propyl)-amine hydrogen chloride To a solution of 4-(1-ethyl-propylamino)-6-methyl-2-(2,4,6-trimethyl-phenoxy)-pyridin-3-yl]-methanol (40 mg, 0.117 mmol) in 0.3 ml of dry methylene chloride was added thionyl chloride (0.15 ml) and stirred at rt for 1 hr. The mixture was concentrated to dryness and pumped in vacuo to give white glass form. The glass form was trituated with ether to give the title compound (47 mg,100%) as a white solid. $^1$H NMR (CDCl$_3$) δ6.92 (s, 2H), 6.24 (s, 1H), 5.50 (d, 1H), 4.72 (s, 2H), 3.50 (m, 1H), 2.73 (s, 3H), 2.27 (s, 3H), 2.15 (s, 6H), 1.5–1.8 (m, 4H), 0.97 (t, 6H) ppm.

EXAMPLE 86

[3,6-Dimethyl-2-(2,4,6-trimethyl-phenoxy)-pyridin-4-yl]-(1-ethyl-propyl)-amine

To a solution of [3—Chloromethyl-6-methyl-2-(2,4,6-trimethyl-phenoxy)-pyridin-4-yl]-(1-ethyl-propyl)-amine (35 mg, 0.088 mmol) in dry THF (0.5 ml) was added 1M lithium aluminum hydride in THF (0.3 ml, 0.3 mmol) and the resulting mixture was stirred at rt for 1.5 hours. The mixture was quenched with 0.1 ml of water, 0.1 ml of 2N NaOH and 0.3 ml of water and stirred for 5 min. The mixture was filtered and washed with THF. The filtrate was concentrated to dryness. The residue was dissolved in chloroform and dried over anhydrous sodium sulfate, filtered, and concentrated to dryness to give 28 mg (100%) of oil. The oil was purified through silica gel column chromatography using chloroform as eluent to give 26 mg of the title compound as an oil. $^1$H NMR (CDCl$_3$) δ6.85 (s, 2H), 6.08 (s, 1H), 3.72 (d, NH,1H), 3.35 (m, 1H), 2.30 (s, 3H), 2.16 (s, 3H), 2.13 (s, 3H), 2.05 (s, 6H), 1.45-1.75 (m, 4H), 0.98 (t, 6H) ppm. The corresponding HCl salt was prepared and trituated with ether to give 20 mg of white solid. $^1$H NMR (CDCl$_3$) δ6.88 (s, 2H), 6.19 (s, 1H), 4.98 (brs, 1H), 3.50 (m, 1H), 2.71 (s, 3H), 2.26 (s, 3H), 2.12 (s, 6H), 2.00 (s, 3H), 1.5-1.8 (m, 4H), 0.95 (t, 6H) ppm.

EXAMPLE 87

(1-Ethyl-propyl)-[3-methoxymethyl-6-methyl-2-(2,4,6-trimethyl-phenoxy)-pyridin-4-yl]-amine To a solution of 4-(1-ethyl-propylamino)-6-methyl-2-(2,4,6-trimethyl-phenoxy)-pyridin-3-yl]-methanol (46 mg, 0.134 mmol) in dry THF (0.5 ml) was added 60% sodium hydride in oil (6 mg, 0.134 mmol) and stirred for 2 min. Methyl iodide (0.1 ml) was added and the mixture was stirred at room temperature overnight. The reaction mixture was quenched with water and extracted with ethyl acetate. The organic layer was dried and concentrated to give the title compound as an oil (40 mg, 84%). $^1$H NMR (CDCl$_3$) δ6.84 (s, 2H), 6.06 (s, 1H), 5.13 (d, 1H), 4.78 (s, 2H), 3.33 (s, 3H), 3.29 (m, 1H), 2.27 (s, 3H), 2.12 (s, 3H), 2.04 (s, 6H), 1.3–1.6 (m, 4H), 0.93 (t, 6H) ppm.

EXAMPLE 88

(1-Ethyl-propyl)-[6-methyl-3-nitro-2-(2,4,6-trimethyl-phenoxy)-pyridin-4yl]-amine To a mixture of (2-chloro-6-methyl-3-nitro-pyridin-4-yl)-(1-ethyl-propyl)-amine (80 mg, 0.31 mmol) and 2,4,6-trimethylphenol (43 mg, 0.31 mmol) in 2ml of dry THF was added potassium tert-butoxide (35 mg, 0.31 mmol) and the resulting mixture was stirred at rt overnight. The mixture was quenched with water and extracted with ethyl acetate. The organic layer was dried and concentrated to give a yellow solid. The solid was purified through silica gel column chromatography using 6:4 ratio of chloroform:hexane as eluent to give 91 mg (83%) of the title compound as yellow solid, mp 16–162° C. $^1$H NMR (CDCl$_3$) δ7.62 (d, 1H), 6.87 (s, 2H), 6.18 (s, 1H), 3.40 (m, 1H), 2.30 (s, 3H), 2.15 (s, 3H), 2.10 (s, 6H), 1.5–1.8 (m, 4H), 0.99 (t, 6H) ppm.

EXAMPLE 89

N4-(1-Ethyl-propyl)-6-methyl-3-nitro-N2-(2,4,6-trimethyl-phenyl)-pyridine-2,4-diamine A mixture of (2-chloro-6-methyl-3-nitro-pyridin-4-yl)-(1-ethyl-propyl)-amine (250 mg, 0.97 mmol) and 2,4,6-trimethylaniline (262 mg, 1.94 mmol) in 4 ml of dry DMSO was heated at 130° C. overnight. The mixture was quenched with water and extracted with ethyl acetate. The organic layer was dried and concentrated to give a yellow oil. The oil was purified through silica gel column chromatography to give 150 mg (43%) of the title compound as yellow solid, mp 104–107° C. $^1$H NMR (CDCl$_3$) δ10.36 (s, 1H), 9.24 (d, 1H), 6.93 (s, 2H), 5.86 (s, 1H), 3.45 (m, 1H), 2.32 (s, 3H), 2.18 (s, 6H), 2.13 (s, 3H), 1.55–1.80 (m, 4H), 0.99 (t, 6H) ppm.

EXAMPLE 90

N4-(1-Ethyl-propyl)-6-methyl-2-(2,4,6-trimethyl-phenoxy)-pyridine-3,4-diamine

A mixture of (1-ethyl-propyl)-[6-methyl-3-nitro-2-(2,4,6-trimethyl-phenoxy)-pyridin-4-yl]-amine (40 mg, 0.112 mmol) and 4 mg of 10% Pd/C in 10 ml of ethanol was hydrogenated at 50 psi overnight. The mixture was filtered through Celite® and the filtrate was concentrated to dryness to give a light berown crystals which was purified through silica gel column chromatography using 1:1 chloroform:hexane as eluent to give the title compound as golden crystals (36 mg, 97%), mp 105–107° C. $^1$H NMR (CDCl$_3$) δ6.88 (s, 2H), 6.11 (s, 1H), 4.00 (brs, 1H), 3.28 (m, 1H), 3.10 (brs, 2H), 2.31 (s, 3H), 2.16 (s, 3H), 2.10 (s, 6H), 1.45–1.75 (m, 4H), 0.98 (t, 6H) ppm. The corresponding HCl salt was prepared as white solid, mp 174–178° C., 1H NMR(D$_2$O) δ7.09 (s, 2H), 6.63 (s, 11H), 3.65 (m, 1H), 2.31 (s, 3H), 2.25 (s, 3H), 2.11 (s, 6H), 1.45–1.80 (m, 4H), 0.91 (t, 6H) ppm.

EXAMPLE 91

[2-(4-Chloro-2,6-dimethyl-phenoxy)-6-methyl-3-nitro-pyridin-4-yl]-(1-ethyl-propyl)-amine To a mixture of (2-chloro-6-methyl-3-nitro-pyridin-4-yl)-(1-ethyl-propyl)-amine (850 mg, 3.30 mmol) and 4-chloro-2,6-dimethylphenol (516 mg, 3.30 mmol) in 25 ml of dry THF was added potassium tert-butoxide (370 mg, 3.30 mmol) and the resulting mixture was stirred at room temperature overnight. The mixture was quenched with water and extracted with ethyl acetate. The organic layer was dried and concentrated to give a yellow solid (1.31 g). The solid was purified through silica gel column chromatography using 6:4 ratio of chloroform:hexane as eluent to give 1.10 g (88%) of the title compound as yellow solid, mp 152–154° C. $^1$H NMR (CDCl$_3$) δ7.65 (d, 1H), 7.05 (s, 2H), 6.21 (s, 1H), 3.41 (m, 1H), 2.15 (s, 3H), 2.11 (s, 6H), 1.5–1.8 (m, 4H), 0.99 (t, 6H) ppm.

EXAMPLE 92

2-(2,6-Dimethyl-phenoxy)-N4-(1-ethyl-propyl)-6-methyl-pyridine-3,4-diamine

A mixture of (1-ethyl-propyl)-[6-methyl-3-nitro-2-(4-chloro-2,6-dimethyl-phenoxy)-pyridin-4-yl]-amine (800 mg, 2.12 mmol) and 160 mg of 10% Pd/C in 150 ml of ethanol was hydrogenated at 50 psi overnight. The mixture was filtered through Celite® and the filtrate was concentrated to dryness to give a purple glass form (810 mg) which was purified through silica gel column chromatography using 1:1 chloroform:hexane as eluent to give the title compound as tan crystals (360 mg), mp 98–100° C. $^1$H NMR (CDCl$_3$) δ7.05 (m, 3H), 6.11 (s, 1H), 4.00 (brs, 1H), 3.28 (m, 11H), 3.09 (brs, 2H), 2.14 (s, 9H), 1.45–1.75 (m, 4H), 0.98 (t, 6H) ppm. The corresponding HCl salt was prepared as white solid, mp 158–162° C., $^1$H NMR(D$_2$O) δ7.27 (s, 3H), 6.67 (s, 1H), 3.65 (m, 1H), 2.27 (s, 3H), 2.16 (s, 6H), 1.45–1.80 (m, 4H), 0.93 (t, 6H) ppm.

EXAMPLE 93

N4-(1-Ethyl-propyl)-6-methyl-N2-(2,4,6-trimethyl-phenyl)-pyridine-2,3,4-triamine A mixture of N4-(1-ethyl-propyl)-6-methyl-3-nitro-N2-(2,4,6-trimethyl-phenyl)-pyridine-2,4-diamine (40 mg, 0.112 mmol) and 8 mg of 10% palladium/carbon (Pd/C) in 20 ml of ethanol was hydrogenated at 50 psi overnight. The mixture was filtered through celite and the filtrate was concentrated to dryness to give adark residue (40 mg). $^1$H NMR (CDCl$_3$) δ6.88 (s, 2H), 5.97 (s, 1H), 4.32 (d, 1H), 3.28 (m, 1H),2.27 (s, 3H), 2.26 (s, 3H), 2.18 (s, 6H), 1.45–1.75 (m, 4H), 0.93 (t, 6H) ppm. The corresponding di-HCl salt was prepared as a tan solid, mp 213–216° C., $^1$H NMR (DMSO-d6) δ11.1 (s, 1H), 8.48 (s, 1H), 6.98 (s, 2H), 6.73 (brs, $^1$H), 6.38 (s, 1H), 3.36 (m, 1H), 2.28 (s, 3H), 2.19 (s, 3H), 2.08 (s, 6H), 1.54 (m, 4H), 0.88 (t, 6H) ppm.

EXAMPLE 94

2-(4-Chloro-2,6-dimethyl-phenoxy)-N4-(1-ethyl-propyl)-6-methyl-pyridine-3,4-diamine A mixture of (1-ethyl-propyl)-[6-methyl-3-nitro-2-(4-chloro-2,6-dimethyl-phenoxy)-pyridin-yl]-amine (100 mg, 0.265 mmol) and iron (73 mg, 1.33 mmol) in 12 ml of AcOH/H$_2$O (1:1) and heated at 60° C. for 3 hours. The mixture was concentrated to dryness. The residue was diluted with water and extracted with ethyl acetate. The organic layer was dried and concentrated to give the title compound. $^1$ H NMR (CDCl$_3$) δ7.04 (s, 2H), 6.12 (s, 1H), 3.60 (brs, 2H), 3.28 (m, 1H), 2.14 (s, 3H), 2.10 (s, 6H), 1.45–1.80 (m, 4H), 0.97 (t, 6H) ppm.

EXAMPLE 95

N-(1-Ethyl-propyl)-2-methyl-5-nitro-N'-(2,4,6-trimethyl-pyridin-3-yl)-pyrimidine-4,6-diamine To a cooled solution of (6-chloro-2-methyl-5-nitro-pyrimidin-4-yl)-(2,4,6-trimethyl-pyridin-3-yl)-amine (88 mg, 0.29 mmol) in 1 ml of dry THF was added 1-ethyl-propyl-amine (80 mg, 0.92 mmol) at −78° C. The mixture was stirred at that temperature for 3 hrs, then warmed to −10° C. for 1 hour. The mixture was quenched with water and extracted with ethyl acetate. The organic layer was dried and concentrated to give the title compound (88 mg, 86%) as an orange solid, mp 151–152° C. $^1$H NMR (CDCl$_3$) δ9.16 (d, 1H), 6.92 (s, 1H), 4.35 (m, 1H), 2.50 (s, 3H), 2.39 (s, 3H), 2.18 (s, 3H), 2.16 (s, 3H), 1.5–1.80 (m, 4H), 0.94 (t, 6H) ppm.

EXAMPLE 96

(1-Ethyl-propyl)-[2-methyl-5-nitro-6-(2,4,6-trmethyl-pyridin-3yloxy)-pyrimidin-yl]-amine A solution of 3-hydroxy-2,4,6-trimethylpyridine (41 mg, 0.3 mmol) in 1 ml of dry THF was treated with 60% sodium hydride in oil (13 mg, 0.3 mmol) at rt. The reaction mixture was cooled to −78° C. and a solution of (6-chloro-2-methyl-5-nitro-pyrimidin-4-yl)-(1-ethyl-propyl)-amine (78 mg, 0.3 mmol) in 1 ml of dry THF was added. The reaction was stirred at −78° C. for 1 hour, quenched with water and extracted with ethyl acetate. The organic layer was dried and concentrated to give 91 mg (84%) of white solid of the title compound, mp 134–135° C. $^1$H NMR (CDCl$_3$) δ8.30 (d, 1H), 6.89 (s, 2H), 4.30 (m, 1H), 2.31 (s, 3H), 2.26 (s, 3H), 2.10 (s, 6H), 1.5–1.8 (m, 4H), 0.97 (t, 6H) ppm.

EXAMPLE 97

2-(4-Chloro-2,6-dimethyl-phenoxy)-N4-(1-ethyl-propyl)-6-methyl-pyridine-3,4-diamine A mixture of [2-(4-chloro-2,6-dimethyl-phenoxy)-6-methyl-3-nitro-pyridin-4-yl]-(1-ethyl-propyl)-amine (810 mg, 2.14 mmol) and iron (Fe) (594 mg, 10.72 mmol) in 96 ml of 1:1 of AcOH:H$_2$O was heated at reflux for 2 hours. Additional Fe (600 mg) was added. The mixture was heated for an additional 1.5 hours. The reaction mixture was concentrated to dryness. The residue was quenched with water, basified to pH 9.0 and filtered through celite. The filtrate was extracted with ethyl acetate. The organic layer was washed with brine, dried and concentrated to give the title compound as a yellow oil. The oil was purified through silica gel column chromatography using chloroform as eluent to give 570 mg of 2-(4-chloro-2,6-dimethyl-phenoxy)-N4-(1-ethyl-propyl)-6-methyl-pyridine-3,4-diamine as a tan solid, mp 72–74° C. $^1$H NMR(CDCl$_3$) δ7.04(s,2H), 6.11(s, 1H), 4.03(d,1H), 3.30(m,1H), 3.07(s,1H), 2.14(s,3H), 2.10 (s,6H), 1.4–1.75(m,4H), 0.97(t,6H)ppm. The corresponding di-HCl salt was prepared as a white solid, mp 208–210° C.

EXAMPLE 98

N-[4-(1-Ethyl-propylamino)-6-methyl-2-(2,4,6-trimethyl-phenoxy)-pyridin-3-yl]-acetamide A mixture of 2-(2,4,6-trimethyl-phenoxy)-N4-(1-ethyl-propyl)-6-methyl-pyridine-3, 4-diamine (250 mg, 0.763 mmol), acetic anhydride (72 mg, 0.763 mmol) and triethylamine (77 mg, 0.763 mmol) in 5 ml of methylene chloride was stirred at room temperature for 3 hours. The mixture was quenched with water and extracted with ethyl acetate. The organic layer was dried and concentrated to dryness to give 310 mg of the crude material. The crude material was purified through silica gel column chromatography using 2% methanol in chloroform as eluent to give 250 mg (89% yield) of N-[4-(1-ethyl-propylamino)-6-methyl-2-(2,4,6-trimethyl-phenoxy)-pyridin-3-yl]-acetamide as tan solid, mp 154–156° C. $^1$H NMR(CDCl$_3$) δ6.97(0.64H), 6.86(s,2H), 6.26(0.36H), 6.14(0.64H), 6.12(s,0.36H), 4.80(d,0.64H), 4.40(d,0.36H), 3.2–3.4(m,1H), 2.29(s,3H), 5 2.26(s,1.9H), 2.17(s,1.1H), 2.16(s,1.9H), 2.06(s,6H), 1.99(s,1.1H), 1.4–1.75(m,4H), 0.97(t,6H)ppm.

EXAMPLE 99

N-[2-(4-Chloro-2,6-dimethyl-phenoxy)-4-(1-ethyl-propylamino)-6-methyl-pyridin-3-yl]-acetamide The title compound (35 mg) was isolated as a side product from the reduction experiment described in the Example 97.

Compound can be prepared by standard acylation method by reacting 2-(4-chloro-2,6-dimethyl-phenoxy)-N4-(1-ethyl-propyl)-6-methyl-pyridine-3,4-diamine with acetic anhydride and triethylamine in methylene chloride. A tan solid was prepared, mp 161–164° C. $^1$H NMR(CDCl$_3$) δ7.04(s, 2H), 6.88(s,0.6H), 6.26(s,0.4H), 6.15(s,1H), 4.75(d,0.6H), 4.40(d,0.4H), 3.30(m,$_1$H), 2.27(s,1.8H), 2.15(s,3H), 2.06(s, 6H), 1.98(s,1.2H), 1.4–1.8(m,4H), 0.97(t,6H)ppm.

EXAMPLE 100

1-Ethyl-3-[4(1-ethyl-propoylamino)-6-methyl-2-(2, 4,6-trimethyl-phenoxy)-pyridin-3-yl]-urea $^1$H NMR(CDCl$_3$) δ6.85(s,2H), 6.11 (s,1H), 5.38(s,1H), 4.68(s,1H), 4.65(m,1H), 3.2–3.4(m,3H), 2.28(s,3H), 2.16(s, 3H), 2.08(s,6H), 1.4–1.7(m,4H), 1.10(t,3H), 0.93(t,6H)ppm.

EXAMPLE 101

N-14-(1-Ethyl-propyl)-2-methyl-N"-(2,4,6-trimethyl-pyridin-3-yl)-pyrimidine-4,5,6-triamine The title compound was prepared by hydrogenation of N-(1-ethyl-propyl)-2-methyl-5-nitro-N"-(2,4,6-trimethyl-pyridin-3-yl)-pyrimidine-4,6-diamine by the method analogous to that described in Example 93. $^1$H NMR(CDCl$_3$) δ6.9(s,1H), 6.25(brs,1H), 4.7(d,1H), 4.08(m,1H), 2.5(s,3H), 2.45(s,3H), 2.30(s,3H), 2.20(s,3H), 1.45–1.7(m,4H), 0.98(t, 6H) ppm.

EXAMPLE 102

N4(1-Ethyl-propyl)-2-methyl-6-(2,4,6-trimethyl-phenoxy)-pyrimidine-4,5-diamine

The title compound was prepared by hydrogenation of (1-ethyl-propyl)-[2-methyl-5-nitro-6-(2,4,6-trimethyl-phenoxy)-pyrimidin-4-yl]-amine by the method analogous to that described in Example 93. 1H NMR(CDCl$_3$) δ6.88(s, 2H), 4.52(d,1H), 4.10(m,1H), 35 2.94(brs,2H), 2.30(s,3H), 2.23(s,3H), 2.09(s,6H), 1.4–1.8(m,4H), 0.95(t,6H) ppm. The corresponding HCl salt, mp 248–250° C. $^1$H NMR(CD$_3$OD) δ6.91(s,2H), 4.00(m,1H), 2.39(s,3H), 2.28(s,3H), 2.07(s, 6H), 1.6–1.8(m,4H), 1.00(t,6H) ppm.

EXAMPLE 103

[6-(1-Ethyl-propoxy)-2-methyl-5-nitro-pyrimidin-4-yl-]-(2,4,6-trimethyl-phenyl-amine A mixture of 3-pentanol (0.5 ml) and 60% sodium hydride (NaH) in oil (89 mg, 2.22 mmol) in 2 ml of dry THF was stirred for 2 min, then treated with a solution of 6-(chloro-2-methyl-5-nitropyrimidin-14-y)-(2,4,6-trimethylphenyl)-amine(350 mg,1.14 mmol) in 3 ml of dry THF at –78° C. and stirred at that temperature for 1 hour, then stirred at room temperature overnight. The mixture was quenched with water and extracted with ethyl acetate. The organic layer was dried and concentrated to give the crude material which was purified through silica gel column chromatography using 2:1 of hexane/CHCl$_3$ as eluent to give 331 mg (85%) of the title compound as a yellow solid, mp 112–113° C. $^1$H NMR(CDCl$_3$) δ9.48(brs,1H), 6.49(s,2H), 5.37(m,$_1$H), 2.33(s,3H), 2.29(s,3H), 2.18(s,6H), 1.7–1.9(m,4H), 0.99(t, 6H) ppm.

EXAMPLE 104

N-(1-Ethyl-propyl)-2-methyl-5-nitro-N'-(2,4,6-trimethyl-phenyl)-pyrimidine-4,6-diamine The title compound was prepared by the method analogous to that described in Example 5 using 1-ethylpropylamine. $^1$H NMR(CDCl$_3$) δ10.48(s,1H), 9.25 (d,1H), 6.94(s,2H), 4.37(m,$_1$H), 2.32(s,3H), 2.21(s,3H), 2.18(s,6H), 1.5–1.8(m,4H), 0.97(t,6H)

EXAMPLE 105

6-(1-Ethyl-propoxy)-2-methyl-N4-(2,4,6-trimethyl-phenyl)-pyrimidine-4,5-diamine

The title compound was prepared by the method analogous to that described in Example 93 starting from [6-(1-ethyl-propoxy)-2-methyl-5-nitro-pyrimidin-4-yl]-(2,4,6-trimethyl-phenyl)-amine. $^1$H NMR(CDCl$_3$) δ6.92(s,2H), 5.96(s,1H), 5.12(m,1H), 2.85(brs, 1H), 2.31 (s,3H), 2.30(s, 3H), 2.19(s,6H), 1.70(m,4H), 0.94(t,6H) ppm.

EXAMPLE 106

6-(1-Ethyl-propoxy)-2-methyl-5-nitro-pyrimidin-4-yl]-(2,4,6-trimethyl-pyridin-3-yl)-amine The title compound was prepared by the method analogous to that described in Example 103 starting from (6-chloro-2-methyl-5-nitropyrimidin-4-yl)-(2,4,6-trimethyl-pyridin-3-yl)-amine and sodium 3-pentanoxide. $^1$H NMR (CDCl$_3$) δ9.45(s,1H), 6.95(s,1H), 5.35(m,1H), 2.53(s,3H), 2.41(s,3H), 2.29(s,3H), 2.18(s,3H),1.7–1.9(m,4H), 0.98(t, 6H) ppm.

EXAMPLE 107

N-(1-Ethyl-propyl)-2-methyl-N"-(2,4,6-trimethyl-phenyl)-pyrimidine-4,5,6-triamine The title compound was prepared by the method analogous to that described in Example 93 starting from N-(1-ethyl-propyl)-2-methyl-5-nitro-N'-(2,4,6-trimethyl-phenyl)-pyrimidin-4,6-diamine. $^1$H NMR(CDCl$_3$) δ6.90(s,2H), 6.10 (s,1H), 4.78(d,1H), 4.03(m,1H), 2.31 (s,3H), 2.29(s,3H), 2.20(s,6H), 1.4–1.6(m,4H), 0.91 (t,6H) ppm.

EXAMPLE 108

6-(1-Ethyl-propoxy)-2-methyl-9-(2,4,6-trimethyl-phenyl)-7,9-dihydro-purin-8-one

A mixture of 6-(1-ethyl-propoxy)-2-methyl-N4-(2,4,6-trimethyl-phenyl)-pyrimidine-4,5-diamine (182 mg, 0.554 mmol), triethylamine (39 mg, 0.388 mmol) and triphosgene (58 mg, 0.196 mmol) in 6 ml of dry THF was stirred at room temperature for 30 min. The mixture was quenched with water and extracted with chloroform. The organic layer was dried and concentrated to give 177 mg (90%) of the title compound as a white solid, mp 159–160° C. $^1$H NMR (CDCl$_3$) 68.50(s,1H),6.99(s,2H), 5.30(m,1H),2.47(s,3H), 2.32(s,3H), 2.08(s,6H), 1.73(m,4H), 0.94(t,6H) ppm.

EXAMPLE 109

6-(1-Ethyl-propoxy)-2-methyl-N4-(2,4,6-trimethyl-pyridin-3-yl)-pyrimidine-4,5-diamine The title compound was prepared by the method analogous to that described in Example 93 starting from 6-(1-ethyl-propoxy)-2-methyl-5-nitro-pyrimidin-yl]-(2,4,6-trimethyl-pyridin-3-yl)-amine. $^1$H NMR(CDCl$_3$) δ6.89(s, 1H), 5.97(s,1H), 5.29(m,1H), 2.90(brs,1H), 2.48(s,3H), 2.41 (s,3H), 2.26(s,3H), 2.17(s,3H), 1.68(m,4H), 0.93(t,6H) popm.

EXAMPLE 110

6-(1-Ethyl-propylamino)-2-methyl-9-(2,4,6-trimethyl-phenyl)-7,9-dihydro-purin-8-one The title compound was prepared by the method analogous to that described in Example 108 starting from N-(1- ethyl-propyl)-2-methyl-N'-(2,4,6-trimethyl-phenyl)-pyrimidine-4,5,6-triamine. $^1$H NMR(CDCl$_3$) δ6.59(s,2H), 5.28(d,1H), 3.92(m,1H), 2.40(s,3H), 2.32(s,3H), 2.08(s,6H), 1.25–1.45(m,4H), 0.80(t,6H)ppm.

EXAMPLE 111

N4-(1-Ethyl-propyl)-6,N3,N3-trimethyl-2-(2,4,6-trimethyl-phenoxy)-pyridine-3,4-diamine and N4-(1-Ethyl-propyl)-6,N3-dimethyl-2-(2,4,6-trimethyl-phenoxy)-pyridine-3,4-diamine To a solution of N4-(1-ethyl-propyl)6-methyl-2-(2,4,6trimethyl-phenoxy)-pyridine-3,4-diamine (0.250 g, 0.763 mmol) in dry THF (6 ml) was treated with 1M LiN(SiMe$_3$)$_2$ in THF (1.0 ml, 1.0 mmol) at −78° C. and stirred for 10 min. an excess of methyl iodide was added and the resulting mixture was stirred at room temperature overnight. The mixture was quenched with water and extracted with ethyl acetate. The organic layer was dried and concentrated to give a crude material. The crude material was purified through silica gel column chromatography using 5% ethyl acetate in hexane as eluent to give N4-(1-ethyl-propyl)-6,N3,N3-trimethyl-2-(2,4,6trimethyl-phenoxy)-pyridine-3,4-diamine and N4-(1-ethyl-propyl)-6,N3-dimethyl-2-(2,4,6trimethyl-phenoxy)-pyridine-3,4-diamine.

N4-(1-Ethyl-propyl)-6,N3,N3-trimethyl-2-(2,4,6-trimethyl-phenoxy)-pyridine-3,4-diamine: $^1$H NMR (CDCl$_3$) δ6.88(s,2H), 6.02(s,1H), 5.55(d,1H), 3.21 (m,1H), 2.79(s,6H), 2.30(s,3H), 2.10(s,3H), 2.09(s,6H), 1.4–1.75(m, 4H), 0.95(t,6H) ppm.

N4-(1-Ethyl-propyl)-6.N3-dimethyl-2-(2,4,6-trimethyl-phenoxy)-pyridine-3,4-diamine: $^1$H NMR(CDCl$_3$) δ6.89(s, 2H), 6.10(s,1H), 4.84(d,1H), 3.30(m,1H), 2.98(s,1H), 2.72 (s,3H), 2.32(s,3H), 2.16(s,3H), 2.12(s,6H), 1.45–1.70(m, 4H), 0.99(t,6H) ppm.

EXAMPLE 112

N4-(1-Ethyl-propyl)-6-methyl-2-(2,4,6-trimethyl-phenoxy)-pyrimidine-3-chloro-4-amine The title compound was prepared by the method analogous to those of Examples 33–39 starting from 3,4-dichloro-6-methyl-2-(2,4,6trimethyl-phenoxy)-pyrimidine and 1-ethyl-propylamine. $^1$H NMR(CDCl$_3$) δ6.87(s,2H), 4.97(d, 1H), 4.12(m,1H), 2.30(s,3H), 2.25(s,3H), 2.10(s,6H), 1.4–1.8(m,4H), 0.96(t,6H) ppm.

EXAMPLE 113

Butyl-{2,8-dimethyl-9-(2,4,6-trimethyl-phenyl)-9H-purin-6-yl}-ethyl-amine

A mixture of N-butyl-N-ethyl-2-methyl-N'-(2,4,6-trimethylphenyl)-pyrimidine-4, 5,6-triamine (105 mg, 0.63 mmol) and triethyl orthoacetate (0.204 g,1.25 mmol) and 10 mg of p-TsOH in toluene was heated reflux overnight. The mixture was concentrated to dryness and the residue was quenched with water and extracted with ethyl acetate. The organic layer was dried and concentrated to give yellow oil. The oil was purified through silica gel column chromatography using 1:1 of hexane:chloroform as eluent to give the title compound. $^1$H NMR(CDCl$_3$) δ7.01(s,2H), 3.9–4.1(m, 4H), 2.45(s,3H), 2.35(s,3H), 2.20(s,3H), 1.91 (s,6H), 1.6–1.8(m,2H), 1.35–1.5(m,2H), 1.29(t,3H), 0.99(t,3H) ppm.

Preparation A (6-Chloro-2,5-dimethylpyrimidin-4-yl-(2,4,6-trimethylphenyl)-amine A mixture of 2,5-dimethyl-4,6-dichloropyrimidine (1.77 g, 10 mmol) and trimethylaniline (2.70 9, 20 mmol) in 5 ml of DMSO was heated in an oil bath of 160° C. for 4 hours. The mixture was quenched with water and extracted with ethyl acetate. The organic layer was separated, dried and concentrated to give the crude material. After silica gel column purification, and trituration with hexane, white crystals (790 mg) were obtained; high MS calc, 275.1185, found 275.11667; IR(KBr) 3290, 3240, 2900, 1540 cm-1. 1 H NMR (CDCl$_3$) δ6.91 (s, 2H), 5.85 (s, 1H), 2.33 (s, 3H), 2.87 (s, 3H), 2.24 (s, 3H), 2.12 (s, 6H) ppm.

Preparation B (6-Chloro-2,5-dimethylpyrimidin-4-yl)-methyl-(2,4,6-trimethylphenyl)-amine A solution of (6-chloro-2,5-dimethylpyrimidin-4-yl)-(2,4,6-trimethylphenyl)-amine (276 mg, 1 mmol) in dry THF (2 ml) was treated with sodium hydride (60% in oil, 60 mg, 1.5 mmol) at room temperature. After stirring for 2 minutes, an excess of methyl iodide (0.5 ml) was added and the resulting mixture was stirred at room temperature for 20 minutes. The mixture was quenched with saturated ammonium chloride and extracted with ethyl acetate. The organic layer was separated, dried and concentrated to give a pale yellow solid (255 mg). $^1$H NMR (CDCl$_3$) δ6.85 (s, 2H), 3.26 (s, 3H), 2.50 (s, 3H), 2.27 (s, 3H), 2.03 (s, 6H), 1.39 (s, 3H) ppm.

Preparation C

4-Chloro-2,5-dimethyl-6-(2,4,6-trimethylphenyoxy)-pyrimidine

A solution of 2,4,6-trimethylphenol (2.720 g, 20 mmol) in 60 ml of dry THF was treated with NaH (60% in oil, 1.200 g, 30 mmol) at room temperature. After stirring at room temperature for 15 minutes, 2,5-dimethyl-4,6-dichloropyrimidine (3.34 g, 20 mmol) was added and the resulting mixture was heated at reflux for 15 hours. The mixture was quenched with saturated ammonium chloride and extracted with ethyl acetate. The organic layer was dried and concentrated to give 5.4528 g of beige solid. The solid was recrystallized from isopropanol to give 5.1345 g of pale yellow solid, mp 86–87° C.; high MS (C$_{15}$H$_{17}$ClN$_{20}$) calc. 276.1025, found 276.10359. $^1$H NMR (CDCl$_3$) δ6.87 (s, 2H), 2.37 (s, 6H), 2.28 (s, 3H), 2.01 (s, 6H) ppm.

Preparation D 2,4-Dichloro-3,6dimethylpyridine

A mixture of 2,4-dihydroxy-3,6-dimethylpyridine (2.86 9, 20.58 mmol), POCl$_3$ (15 ml) and N,N-diethylaniline (3.6 ml, 22.64 mmol) was heated at reflux for 3 hours. The mixture was cooled, poured into ice water and extracted with diethyl ether. The organic layer was dried and concentrated to give 3.02 g of the crude material. After silica gel column chromatography using chloroform as eluent, 1.3102 g of the title compound was obtained as a yellow oil. $^1$ H NMR (CDCl$_3$) δ7.07 (s, 1H), 2.43 (s, 3H), 2.39 (s, 3H) ppm.

Preparation E

4-Chloro-3,6-dimethyl-2-(2,4,6-trimethyl-phenyoxy)-pyridine

A solution of 2,4,6-trimethylphenol (450 mg, 3.31 mmol) in 2 ml of DMSO was treated with NaH (60% in oil, 180 mg, 4.5 mmol). After 5min, 2,4-Dichloro-3,6-dimethyl-pyridine (528 mg, 3 mmol) was added. The mixture was heated in the oil bath of 130° C. for 6 hours. The mixture was quenched with water and extracted with EtOAc. The organic layer was dried and concentrated to give 812.5 mg of crude material with two regioisomers. After silica gel column chromatography using 1:1 of CHCl$_3$:hexane as eluent, the title compound was isolated as white crystals (141 mg), mp 57–62° C.; high MS for C$_{16}$H$_{18}$ClNO: calc, 275.1072, found 275.70172; IR(KBr) 2951, 2920,1592, 1564 cm-1; $^1$H NMR (CDCl$_3$) δ6.87 (s, 2H), 6.77 (s, 1H), 2.39 (s, 3H), 2.29 (s, 3H), 2.18 (s, 3H), 2.03 (s, 6H) ppm. The regiochemistry was determined by X-ray structural analysis of the undesired regioisomer, 2-chloro-3,6-dimethyl-4-(2,4,6-trimethyl-phenyoxy)-pyridine.

To a solution of 4-chloro-2,5-dimethyl-(2,4,6-trimethyl-phenoxy)-pyridine 1-oxide (34 mg) in 1 ml dry methylene chloride was added 2M PCl$_3$ in methylene chloride (0.022 ml). After addition, the mixture was heated at reflux for 0.5 hours, cooled and concentrated to dryness. The residue was poured into ice-water and extracted with methylene chloride. The organic layer was washed with brine, neutralized with sat. sodium carbonate, dried and concentrated to give 47 mg of the crude material. The crude material was crystallized out upon standing to give 31 mg (95%) of white crystals of the title compound.

Preparation F (6—Chloro-2,5-dimethylpyrimidin-4-yl)-(2,4,6-trimethylphenyl)-acetonitrile To a solution of mesitylacetonitrile (0.900 g, 5.65 mmol) in 8 ml dry THF was added sodium hydride (60% in oil, 0.250 g, 6.21 mmol) and the mixture was stirred at room temperature for 40 minutes. 2,5-Dimethyl-4,6-dichloropyrimidine (1.000 g, 5.65 mmol) was added and the resulting mixture was heated at reflux for 5 hours. The mixture was quenched with water and extracted with ethyl acetate. The organic layer was dried and concentrated to give 1.800 g of a yellow oil. The oil residue was purified through silica gel column chromatography using 10% ethyl acetate in hexane as eluent to give 0.986 9 (58.3%) of the title compound as a white solid, mp 100–102° C. $^1$H NMR (CDCl$_3$) δ6.86 (s, 2H), 5.60 (s, 1H), 2.69 (s, 3H), 2.25 (s, 3H), 2.18 (s, 6H), 1.92 (s, 3H) ppm.

Preparation G 2-(6-Chloro-2,5-dimethylpyrimidin-4-yl)-2-(2,4,6-trimethylphenyl)-propionitrile A solution of (6-chloro-2,5-dimethylpyrimidin-4-yl)-(2,4,6-trimethylphenyl)-acetonitrile (0.250 g, 0.834 mmol) in 4 ml of dry THF was cooled to −78° C. and treated with lithium bistrimethylsilylamide (1.0 M in THF, 0.92 ml) and stirred at that temperature for 45 minutes. Methyl iodide (0.426 g, 3.00 mmol) was added. The reaction mixture was gradually warmed to room temperature and stirred for 1 hour. The reaction mixture was quenched with water and extracted with ethyl acetate. The organic layer was dried and concentrated to give a yellow oil. The oil residue was purified through silica gel chromatotron using ethyl acetate/hexane (4:6) as eluent to give 161 mg (62%) of yellow solid, mp 181–183° C. $^1$H NMR (CDCl$_3$) δ6.980 (s, 2H), 3.45 (s, 3H), 2.40 (s, 3H), 2.24 (s, 3H), 2.21 (s, 6H), 1.25 (s, 3H) ppm.

Preparation H

4-Hydroxy-2,5-dimethyl-6-(2,4,6-trimethyl-benzyl)-pyrimidine

A mixture of 6-chloro-2,5-dimethylpyrimidin-4-yl)-(2,4,6-trimethylphenyl)-acetonitrile (1.5 g, 5.0 mmol) and 60 ml of 85% phosphoric acid was heated at reflux for 2 hours. The mixture was cooled at rt and diluted with water and extracted with chloroform. The organic layer was washed with brine, dried and concentrated to give 1.21 g (95%) of the title compound as a white solid, mp 260–262° C.

Preparation I

4-Chloro-2,5-dimethyl-6-(2,4,6-trimethyl-benzyl)-pyrimidine

A mixture of 4-hydroxy-2,5-dimethyl-6-(2,4,6-trimethyl-benzyl)-pyrimidine (1.2 g, 4.68 mmol) and POCl$_3$ (25 ml) was heated at reflux for 1 hour. The mixture was cooled and evaporated to dryness. The residue was poured into ice-water and extracted with ethyl acetate. The organic layer was washed with brine, dried and concentrated to dryness to give 1.24 g (97%) of golden crystals, mp 82–84° C.

Preparation J

The following compounds were prepared by the methods analogous to that in Preparation C starting with 5-substituted-4,6-dichloro-2-methyl-pyrimidine and substituted phenol in tetrahydrofuran in the presence of a base (sodium hydride) at the temperature indicated below.

5-tert-Butyl-4-chloro-2-methyl-6-(2,4,6-trimethyl-phenoxy)-pyrimidine

The reaction was carried out at reflux in THF to give white crystals, mp 70–72° C., $^1$H NMR (CDCl$_3$) δ6.82 (s, 2H), 2.28 (s, 3H), 2.24 (s, 3H), 1.96 (s, 6H), 1.60 (s, 9H) ppm.

4-Chloro-5-isopropyl-2-methyl-6-(2,4,6-trimethyl-phenoxy)-pyrimidine

The reaction was carried at reflux in THF to give white crystals, mp 68–70° C. $^1$H NMR (CDCl$_3$) δ6.88 (s, 2H), 3.60 (m, 1H), 2.36 (s, 3H), 2.29 (s, 3H), 2.00 (s, 6H), 1.43 (s, 3H), 1.41 (s, 3H) ppm.

4,5-Dichloro-2-methyl-6-(2,4,6-trimethyl-phenoxy)-pyrimidine

The reaction run at room temperature to give white crystals, mp 68–70° C. $^1$H NMR (CDCl$_3$) δ6.88 (s, 2H), 2.41 (s, 3H), 2.29 (s, 3H), 2.04 (s, 6H) ppm.

4-Chloro-5-bromo-2-methyl-6-(2,4,6-trimethyl-phenoxy)-pyrimidine

The reaction was run at 0° C. to room temperature. $^1$H NMR (CDCl$_3$) δ6.88 (s, 2H), 2.41 (s, 3H), 2.29 (s, 3H), 2.03 (s, 6H) ppm.

4-Chloro-2-methyl-6-(2,4,6-trimethyl-phenoxy)-Pyrimidine-5-carbonitrile

The reaction was run at −40° C. to give yellow crystals, mp 89–91 ° C. $^1$H NMR (CDCl$_3$) δ6.89 (s, 2H), 2.51 (s, 3H), 2.29 (s, 3H), 2.04 (s, 6H) ppm.

Preparation K 2,4-Dichloro-3,6-diemthyl-pyridine 1-oxide

A mixture of 2,4-dichloro-3,6-dimethyl-pyridine (790 mg, 4.49 mmol) and 50% m-chloro-perbenzoic acid (1.544 g, 4.49 mmol) in 10 ml of chloroform was stirred at room temperature for 20 hours. The mixture was quenched with water, washed with saturated sodium thiosulfate and saturated sodium carbonate, brine and extracted with chloroform. The organic layer was dried and concentrated to give 954 mg of crude material. The material was purified through silica gel to give 662 mg of the title compound as a white crystals, mp 131–132° C. $^1$H NMR (CDCl$_3$) δ7.22 (s, 1H), 2.51 (s, 3H), 2.47 (s, 3H) ppm.

Preparation L

The following compounds were prepared by the method analogous to that described in Preparation K starting with an appropriate 2,4-dichloro-pyridine and an oxidizing agent.

2,4-Dichloro-6-methyl-1-oxy-nicotinic acid methyl ester

M.p. 90–91.5° C. $^1$H NMR (CDCl$_3$) 67.26 (s, 1H), 3.98 (s, 3H), 2.54 (s, 3H) ppm.

(2,4-Dichloro-6-methyl-1-oxy-pyridin-3-yl)methanol

M.p. 188–191° C. $^1$H NMR (CDCl$_3$) 67.13 (s, 1H), 4.87 (d, 2H), 2.47 (s, 3H), 2.38 (t, 1H, OH) ppm.

2,4-Dichloro-3,5,6-trimethyl-pyridine 1-oxide

M.p. 146–148° C. $^1$H NMR (CDCl$_3$) δ2.57 (s, 3H), 2.49 (s, 3H), 2.38 (s, 3H)) ppm.

2,4-Dichloro-6-methyl-pyridine 1-oxide

M.p. 100–102° C. $^1$H NMR (CDCl$_3$) δ7.42 (d, 1H), 7.22 (d, 1H), 2.55 (s, 3H) ppm.

Preparation M

4-Chloro-2,5-dimethyl-6-(2,4,6-trimethyl-phenoxy)-pyridine-1-oxide

To a solution of 2,4,6-trimethylphenol (415 mg, 3.05 mmol) in dry THF (20 ml) was treated with 60% sodium hydride in oil (122 mg, 3.05 mmol) at room temperature. After all H$_2$ was evolved, 2,4-dichloro-3,6-dimethyl-pyridine 1-oxide (585.4 mg, 3.05 mmol) was added and the resulting mixture was heated at reflux for 2 hours. The mixture was quenched with saturated ammonium chloride and extracted with ethyl acetate. The organic layer was dried and concentrated to dryness to give solid. The solid was recrystallized from pet ether to give 802 mg (90%) of the title compound as white crystals, mp 106–107° C. $^1$H NMR (CDCl$_3$) δ7.04 (s, 1H), 6.78 (s, 2H), 2.41 (s, 3H), 2.36 (s, 3H), 2.22 (s, 3H), 2.06 (s, 6H) ppm.

Preparation of N

The following compounds were prepared by the method analogous to that described in Preparation M starting with an appropriate 2,4-dichloro-pyridine-1-oxide with an appropriate phenol or thiophenol in the presence of a base (potassium tert-buoxide, sodium hydride, or potassium hydride) at temperature between room temperature to reflux in dry THF.

2-(4-Bromo-2,6-dimethyl-phenoxy)-4-chloro-3,6-dimethyl-pyridine 1-oxide

White crystals, mp 137–139° C. $^1$H NMR (CDCl$_3$) δ7.12 (s, 2H), 7.08 (s, 1H), 2.42 (s, 6H), 2.09 (s, 6H) ppm.

4-Chloro-2-(4-chloro-2,6-dimethyl-phenoxy)-3,6-dimethyl-pyridine 1-oxide $^1$H NMR (CDCl$_3$) δ7.08 (s, 1H), 6.97 (s, 2H), 2.42 (s, 6H), 2.09 (s, 6H) ppm, 4-Chloro-6-methyl-2-(2,4,6-trimethyl-phenoxy)-1-oxy-nicotinic acid methyl ester $^1$H NMR (CDCl$_3$) δ7.04 (s, 1H), 6.78 (s, 2H), 3.48 (s, 3H), 2.52 (s, 3H), 2.22 (s, 3H), 2.08 (s, 6H) ppm.

4-Chloro-2,3,5-trimethyl-6-(2,4,6-trimethyl-phenoxy)-pyridine 1-oxide

White crystals, mp 132–134° C. $^1$H NMR (CDCl$_3$) δ6.75 (s, 2H), 2.47 (s, 3H), 2.38 (s, 3H), 2.35 (s, 3H), 2.20 (s, 3H), 2.04 (s, 6H) ppm.

4-Chloro-2-methyl-6-(2,4,6-trimethyl-phenoxy)-pyridine 1-oxide

White crystals, mp 191–193° C. $^1$H NMR (CDCl$_3$) δ6.96 (s, 1H), 6.95 (s, 2H), 2.62 (s, 3H), 2.32 (s, 3H), 2.13 (s, 6H) ppm.

4-Chloro-2-(2,4-dimethyl-phenylsulfanyl)-3,6-dimethyl-pyridine 1-oxide white crystals, mp 148–151 ° C. $^1$ H NMR (CDCl$_3$) δ7.23 (s,1H), 7.02 (s,1H), 6.88 (s, 2H), 2.46 (s, 3H), 2.41 (s, 3H), 2.39 (s, 3H), 2.27 (s, 3H) ppm.

4-Chloro-2-(2,4,6-trimethyl-phenylsulfanyl)-3,6-dimethyl-pyridine 1-oxide

White crystals, mp 132–134° C. $^1$H NMR (CDCl$_3$) δ7.13 (s,1H), 6.91 (s, 2H), 2.46 (s, 3H), 2.31 (s, 6H), 2.27 (s, 3H), 2.10 (s, 3H) ppm.

Preparation of O

The following compounds were prepared by the method analogous to that described in Preparation E, second paragraph, starting with an appropriate 4-chloro-6-substituted phenoxy-pyridine 1-oxide and phosphorous trichloride.

2-(4-Bromo-2,6-dimethyl-phenoxy)-4-chloro-3,6-dimethyl-pyridine

White crystals. $^1$H NMR (CDCl$_3$) δ7.22 (s, 2H), 6.81 (s, 1H), 2.40 (s, 3H), 2.20 (s, 3H), 2.05 (s, 6H) ppm.

4-Chloro-2-(4-chloro-2,6-dimethyl-phenoxy)-3,6-dimethyl-pyridine

White crystals. $^1$H NMR (CDCl$_3$) δ7.07 (s, 2H), 6.81 (s, 1H), 2.41 (s, 3H), 2.20 (s, 3H), 2.06 (s, 6H) ppm.

4-Chloro-6-methyl-2-(2,4,6-trimethyl-phenoxy)-nicotinic acid methyl ester

Yellow crystals, mp 122–125° C. $^1$H NMR (CDCl$_3$) δ6.84 (s, 2H), 6.82 (s, 1H), 3.94 (s, 3H), 2.27 (s, 3H), 2.25 (s, 3H), 2.04 (s, 6H) ppm.

4-Chloro-2,3,5-trimethyl-6-(2,4,6-trimethyl-phenoxy)-pyridine

White crystals, mp 101–103° C. $^1$H NMR (CDCl$_3$) δ6.85 (s, 2H), 2.39 (s, 3H), 2.28 (s, 3H), 2.22 (s, 3H), 2.20 (s, 3H), 2.01 (s, 6H) ppm.

4-Chloro-2-methyl-6-(2,4,6-trimethyl-phenoxy)-pyridine

White crystals, mp 4648° C. $^1$H NMR (CDCl$_3$) δ6.92 (s, 2H), 6.84 (s, 1H), 2.62 (s, 3H), 2.32 (s, 3H), 2.13 (s, 6H) ppm.

4—Chloro-2-(2,4-dimethyl-phenylsulfanyl)-3,6-dimethyl-pyridine

White crystals, mp 148–151° C. $^1$H NMR (CDCl$_3$) δ7.23 (s, 1H), 7.02 (s, 1H), 6.88 (s, 2H), 2.46 (s, 3H), 2.41 (s, 3H), 2.39 (s, 3H), 2.27 (s, 3H) ppm.

4-Chloro-2-(2,4,6-trimethyl-phenylsulfanyl)-3,6-dimethyl-pyridine

White crystals, mp 132–134° C. $^1$H NMR (CDCl$_3$) δ7.13 (s, 1H), 6.91 (s, 2H), 2.46 (s, 3H), 2.31 (s, 6H), 2.27 (s, 3H), 2.10 (s, 3H) ppm.

Preparation P

2-Chloro-4-(1-ethyl-propylamino)-6-methyl-nicotinic acid methyl ester

A mixture of 2,4-dichloro-6-methyl-nicotinic acid methyl ester (2.228 g, 10.13 mmol) and 1-ethyl-propyl amine (1.762 g, 20.26 mmol) in DMSO (4 ml) was heated at 110° C. for 5 hours, then at room temperature overnight. The mixture was quenched with water and extracted with ethyl acetate. The organic layer was dried and concentratd to give 1.796 g of crude material. The crude material was purified through silica gel column chromatography using chloroform to 5% methanol in chloroform as eluent to give 1.167 g (43%) of the title compound as a colorless oil. $^1$H NMR (CDCl$_3$) 657.14 (brs, 1H), 6.27 (s, 1H), 3.86 (s, 3H), 3.27 (m, 1H), 2.33 (s, 3H), 1.3–1.6 (m, 4H), 0.88 (t, 6H) ppm.

Preparation Q

(2-Chloro-6-methyl-3-nitro-pyridin-4-yl)-(1-ethyl-propyl)-amine

A mixture of 2,4-dichloro-6-methyl-3-nitro-pyridine (250 mg, 1.21 mmol) and 1-ethyl-propyl amine (105 mg, 1.21 mmol) in DMSO (4 ml) was stirred at room temperature for 15 hours. The mixture was quenched with water and extracted with ethyl acetate. The organic layer was dried and concentratd to give 280 mg of yellow oil. The oil was purified through silical gel column chromatography using 65% chloroform in hexane as eluent to give 110 mg (35%) of the title compound as a yellow crystal, mp 82–84° C. $^1$H NMR (CDCl$_3$) δ6.57 (d, 1H), 6.46 (s, 1H), 3.39 (m, 1H), 2.42 (s, 3H), 1.4–1.8 (m, 4H), 0.94 (t, 6H) ppm

Preparation R

(6-Chloro-2-methyl-5-nitro-pyrimidin-4-yl)-(1-ethyl-propyl)-amine

A mixture of 2-methyl-5-nitro-4,6-dichloro-pyrimidine (208 mg, 1.00 mmol) and 1-ethyl-propyl-amine (87 mg, 1.03 mmol) in 2 ml of dry THF was stirred at –78° C. for 4 hours. The mixture was quenched with water and extracted with ethyl acetate. The organic layer was washed with brine, dried and concentrated to give a green oil. The oil was purified through silica gel column chromatography using chloroform to 1:1 hexane/chloroform as eluent to give the title compound (93 mg, 35%). $^1$ H NMR (CDCl$_3$) δ7.50 (brs, 1H), 4.29 (m, 1H), 2.51 (s, 3H), 1.4–1.8 (m, 4H), 0.92 (t, 6H) ppm.

Preparation S

(6-Chloro-2-methyl-5-nitro-pyrimidin-4-yl)-(2,4,6-trimethyl-pyridin-3-yl)-amine A solution of 2-methyl-5-nitro-4,6-dichloro-pyrimidine (208 mg, 1.00 mmol) in 2.5 ml of acetonitrile was treated with 2,4,6-trimethyl-3-amino-pyridine (273 mg, 2 mmol) stirred at room temperature 2 hours. The mixture was quenched with water and extracted with ethyl acetate. The organic layer was washed with brine, dried and concentrated to give red residue. The residue was purified through silica gel column chromatography using chloroform to 6% methanol in chloroform as eluent to give the title compound (110 mg, 36%) as an orange oil. $^1$H NMR (CDCl$_3$) δ8.78 (brs, 1H), 6.97 (s, 1H), 2.54 (s, 3H), 2.43 (s, 3H), 2.40 (s, 3H), 2.17 (s, 3H) ppm.

I claim:

1. A compound of the formula

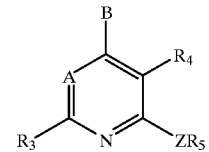

or a pharmaceutically acceptable salt thereof, wherein

A is —CR$_7$;

B is —NHCHR$_1$R$_2$, or —OCHR$_1$R$_2$;

Z is O;

R$_1$ is C$_1$–C$_4$ alkyl which may optionally contain one double or triple bond and which may optionally be substituted with one or two substituents selected independently from hydroxy and C$_1$–C$_4$ alkoxy;

R$_2$ is C$_1$–C$_{12}$ alkyl which may optionally contain one double or triple bond and which may optionally be substituted with from one to three C$_1$–C$_6$ alkoxy;

R$_3$ is methyl;

R$_4$ is hydrogen, methoxy, amino, nitro, —NH(C$_1$–C$_4$ alkyl), —N(CH$_3$)$_2$, —COOCH$_3$, or C$_1$–C$_4$ alkyl one optionally substituted by hydroxy, C$_1$–C$_3$ alkoxy, or chloro;

R$_5$ is phenyl or pyridyl, wherein each R$_5$ is substituted with two or three substituents, independently selected from fluoro, chloro, C$_1$–C$_6$ alkyl optionally containing one carbon—carbon double or triple bond, and C$_1$–C$_4$ alkoxy, and wherein one of said substituents can be further selected from hydroxy, iodo, bromo, formyl, and trifluoromethyl, and wherein said C$_1$–C$_6$ alkyl R$_5$ group may optionally be substituted with one fluoro, hydroxy, or C$_1$–C$_2$ alkoxy; and R$_7$ is hydrogen or methyl.

2. A compound according to claim 1 wherein B is —NHCHR$_1$R$_2$ or —OCHR$_1$R$_2$; R$_1$ is C$_1$–C$_6$ alkyl, which may optionally be substituted with one hydroxy or C$_1$–C$_2$ alkoxy group and may optionally contain one double or triple bond; and R$_2$ is C$_1$–C$_6$ alkyl which may optionally contain one carbon-carbon double or triple bond, wherein said C$_1$–C$_6$ alkyl may optionally be substituted with C$_1$–C$_2$ alkoxy.

3. A compound according to claim 1 wherein R$_2$ is C$_1$–C$_4$ alkyl which may optionally be substituted by C$_1$–C$_2$ alkoxy.

4. A compound according to claim 1 wherein R$_4$ is methyl, methoxy, —COOCH$_3$, amino or nitro.

5. A compound according to claim 1 wherein R$_5$ is phenyl substituted with two or three substituents.

6. A compound according to claim 1 wherein R$_5$ is pyridyl substituted with two or three substituents.

7. A compound according to claim 1, wherein R$_1$ and R$_2$ are independently selected from methyl, and ethyl.

8. A compound according to claim 7, wherein $R_1$ and $R_2$ are both ethyl.

9. A compound according to claim 1, wherein said compound is 2-(4-bromo-2,6-dimethyl-phenoxy)-4-(1-ethyl-propoxy)-3,6-dimethyl-pyridine;

2-(4-ethyl-2,6-dimethyl-phenoxy)4-(1-ethyl-propoxy)-3,6-dimethyl-pyridine;

3-ethyl-4-(1-ethyl-propoxy)-6-methyl-2-(2,4,6-trimethyl-phenoxy)-pyridine;

2-(2,6-dimethyl-4-propyl-phenoxy)4-(1-ethyl-propoxy)-3,6-dimethyl-pyridine;

4-(1-ethyl-propoxy)-2-(4-methoxy-2,6-dimethyl-phenoxy)-3,6-dimethyl-pyridine;

2-(4-ethoxy-2,6-dimethyl-phenoxy)4-(1-ethyl-propoxy)-3,6-dimethyl-pyridine;

2-(4-chloro-2,6-dimethyl-phenoxy)4-(1-ethyl-propoxy)-3,6-dimethyl-pyridine;

4-(1-methoxymethyl-propoxy)-3,6-dimethyl-2-(2,4,6-trimethyl-phenoxy)-pyridine;

4-(1-ethyl-propylamino)-6-methyl-2-(2,4,6-trimethyl-phenoxy)-nicotinic acid methyl ester;

[4-(1-ethyl-propylamino)-6-methyl-2-(2,4,6-trimethyl-phenoxy)-pyridin-3-yl]-methanol;

(1-ethyl-propyl)-[6-methyl-3-nitro-2-(2,4,6-trimethyl-phenoxy)-pyridin-4-yl]-amine;

N4-(1-ethyl-propyl)-6-methyl-2-(2,4,6-trimethyl-phenoxy)-pyridine-3,4-diamine;

[3-chloromethyl-6-methyl-2-(2,4,6-trimethyl-phenoxy)pyridin-4-yl]-(1-ethyl-propyl)-amine;

[3,6-dimethyl-2-(2,4,6-trimethyl-phenoxy)-pyridin-4-yl]-(1-ethyl-propyl)-amine;

(1-ethyl-propyl)-[3-methoxymethyl-6-methyl-2-(2,4,6-trimethyl-phenoxy)-pyridin-4-yl]-amine;

4-(1-ethyl-propoxy)-3,6-dimethyl-2-(2,4,6-trimethylphenoxy)-pyridine;

N4-(1-ethyl-propyl)-6,N3-dimethyl-2-(2,4,6-trimethyl-phenoxy)-pyridine-3,4-diamine; or N4-(1-ethyl-propyl)-6,N3, N3-trimethyl-2-(2,4,6-trimethyl-phenoxy)-pyridine-3,4-diamine;

or a pharmaceutically acceptable salt of one of the above compounds.

10. A compound according to claim 9, wherein said compound is 4-(1-ethyl-propoxy)-3,6-dimethyl-2-(2,4,6-trimethylphenoxy)-pyridine; or a pharmaceutically acceptable salt of said compound.

11. A compound according to claim 1, wherein said compound is 2-(4-bromo-2,6-dimethyl-phenoxy)-4-(1-ethyl-propoxy)-3,6-dimethyl-pyridine;

2-(4-ethyl-2,6-dimethyl-phenoxy)4-(1-ethyl-propoxy)-3,6-dimethyl-pyridine;

3-ethyl-4-(1-ethyl-propoxy)-6-methyl-2-(2,4,6-trimethyl-phenoxy)-pyridine;

2-(2,6-dimethyl-4-propyl-phenoxy)4-(1-ethyl-propoxy)-3,6-dimethyl-pyridine;

4-(1-ethyl-propoxy)-2-(4-methoxy-2,6-dimethyl-phenoxy)-3,6-dimethyl-pyridine;

2-(4-ethoxy-2,6-dimethyl-phenoxy)4-(1-ethyl-propoxy)-3,6-dimethyl-pyridine;

2-(4-chloro-2,6-dimethyl-phenoxy)4-(1-ethyl-propoxy)-3,6-dimethyl-pyridine;

4-(1-methoxymethyl-propoxy)-3,6-dimethyl-2-(2,4,6-trimethyl-phenoxy)-pyridine;

4-(1-ethyl-propylamino)-6-methyl-2-(2,4,6-trimethyl-phenoxy)-nicotinic acid methyl ester;

[4-(1-ethyl-propylamino)-6-methyl-2-(2,4,6-trimethyl-phenoxy)-pyridin-3-yl]-methanol;

(1-ethyl-propyl)-[6-methyl-3-nitro-2-(2,4,6-trimethyl-phenoxy)-pyridin-4-yl]-amine;

N4-(1-ethyl-propyl)-6-methyl-2-(2,4,6-trimethyl-phenoxy)-pyridine-3,4-diamine;

[3-chloromethyl-6-methyl-2-(2,4,6-trimethyl-phenoxy)pyridin-4-yl]-(1-ethyl-propyl)-amine;

[3,6-dimethyl-2-(2,4,6-trimethyl-phenoxy)-pyridin-4-yl]-(1-ethyl-propyl)-amine;

(1-ethyl-propyl)-[3-methoxymethyl-6-methyl-2-(2,4,6-trimethyl-phenoxy)-pyridin-4-yl]-amine;

4-(1-ethyl-propoxy)-3,6-dimethyl-2-(2,4,6-trimethylphenoxy)-pyridine;

N4-(1-ethyl-propyl)-6,N3-dimethyl-2-(2,4,6-trimethyl-phenoxy)-pyridine-3,4-diamine; or N4-(1-ethyl-propyl)-6, N3,N3-trimethyl-2-(2,4,6-trimethyl-phenoxy)-pyridine-3,4-diamine;

4-(1-ethyl-propenyloxy)-3,6-dimethyl-2-(2,4,6-trimethyl-phenoxy)-pyridine;

4-(1-ethyl-propoxy)-6-methyl-2-(2,4,6-trimethyl-phenoxy)-nicotinic acid methyl ester;

4-(1-ethyl-propoxy)-2-methyl-6-(2,4,6-trimethyl-phenoxy)-pyridine;

3-[3,6-dimethyl-2-(2,4,6-trimethyl-phenoxy)-pyridin-4-yloxy]-pentan-2-ol;

4-sec-butoxy-3,6-dimethyl-2-(2,4,6-trimethyl-phenoxy)-pyridine;

4-[4-(1-ethyl-propoxy)-3,6-dimethyl-pyridin-2-yloxy]-3,5-dimethyl-benzaldehyde;

2-(2,6-dimethyl-phenoxy)-4-(1-ethyl-propoxy)-3,6-dimethyl-pyridine;

2-{4-[4-(1-ethyl-propoxy)-3,6-dimethyl-pyridin-2-yloxy]-3,5-dimethyl-phenyl}-propan-2-ol;

4-(1-ethyl-propoxy)-2-(4-iodo-2,6-dimethyl-phenoxy)-3,6-dimethyl-pyridine;

4-[4-(1-ethyl-propoxy)-3,6-dimethyl-pyridin-2-yloxy]-3,5-dimethyl-phenol;

{4-[4-(1-ethyl-propoxy)-3,6-dimethyl-pyridin-3-yloxy]-3,5-dimethyl-phenyl}-methanol;

4-(1-ethyl-propoxy)-2-(4-isopropoxy-2,6-dimethyl-phenoxy)-3,6-dimethyl-pyridine;

4-(1-ethyl-propoxy)-2-(4-methoxymethyl-2,6-dimethyl-phenoxy)-3,6-dimethyl-pyridine;

[3-chloromethyl-6-methyl-2-(2,4,6-trimethyl-phenoxy)-pyridin4-yl]-(1-ethyl-propyl)-amine;

(1-ethyl-propyl)-[6-methyl-3-nitro-2-(2,4,6-trimethyl-phenoxy)-pyridin-4-yl]-amine;

[2-(4-chloro-2,6-dimethyl-phenoxy)-6-methyl-3-nitro-pyridin-4-yl]-(1-ethyl-propyl)-amine;

2-(2,6-dimethyl-phenoxy)-N4-(1-ethyl-propyl)-6-methyl-pyridine-3,4-diamine;

2-(4-chloro-2,6-dimethyl-phenoxy)-N4-(1-ethyl-propyl)-6-methyl-pyridine-3,4-diamine;

2-(4-chloro-2,6-dimethyl-phenoxy)-N4-(1-ethyl-propyl)-6-methyl-pyridine-3,4-diamine;

or a pharmaceutically acceptable salt of one of the above compounds.

12. A pharmaceutical composition for the treatment of (a) a disorder the treatment of which can be effected or facilitated by antagonizing CRF, including but not limited to disorders induced or facilitated by CRF, or (b) a disorder selected from inflammatory disorders, generalized anxiety disorder, panic, phobias, obsessive-compulsive disorder, post-traumatic stress disorder, sleep disorders induced by stress, pain perception, mood disorders, dysthemia, bipolar disorders, cyclothymia, fatigue syndrome, stress-induced headache, cancer, irritable bowel syndrome, Crohn's disease; spastic colon; human immunodeficiency virus infections, neurodegenerative diseases, gastrointestinal diseases, eating disorders, hemorrhagic stress, chemical dependencies and addictions, drug and alcohol withdrawal symptoms, stress-induced psychotic episodes, euthyroid sick syndrome, syndrome of inappropriate antidiarrhetic hormone, obesity; infertility, head traumas, spinal cord trauma, ischemic neuronal damage, excitotoxic neuronal damage, epilepsy, stroke, immune dysfunctions including stress induced immune dysfunctions, muscular spasms, urinary incontinence, senile dementia of the Alzheimer's type, multiinfarct dementia, amyotrophic lateral sclerosis, and hypoglycemia, in a mammal, comprising an amount of a compound according to claim 1 that is effective in the treatment of such disorder, and a pharmaceutically acceptable carrier.

13. A method for the treatment of (a) a disorder the treatment of which can be effected or facilitated by antagonizing CRF, including but not limited to disorders induced or facilitator by CRF, or (b) a disorder selected from inflammatory disorders, generalized anxiety disorder, panic, phobias, obsessive-compulsive disorder, post-traumatic stress disorder, sleep disorders induced by stress, pain perception, mood disorders, dysthemia, bipolar disorders, cyclothymia, fatigue syndrome, stress-induced headache, cancer, irritable bowel syndrome, Crohn's disease, spastic colon, human immunodeficiency virus infections, neurodegenerative diseases, gastrointestinal diseases, eating disorders, hemorrhagic stress, stress-induced psychotic episodes, euthyroid sick syndrome, syndrome of inappropriate antidiarrhetic hormone, obesity, infertility, head traumas, spinal cord trauma, ischemic neuronal damage, excitotoxic neuronal damage, epilepsy, stroke, immune dysfunctions including stress induced immune dysfunctions, muscular spasms, urinary incontinence, senile dementia of the Alzheimer's type, multiinfarct dementia, amyotrophic lateral sclerosis, chemical dependencies and addictions, drug and alcohol withdrawal symptoms, and hypoglycemia, in a mammal, comprising administering to a subject in need of said treatment an amount of a compound according to claim 1, that is effective in treating such disorder.

14. A pharmaceutical composition according to claim 12, wherein the inflammatory disorders are selected from rheumatoid arthritis, osteoarthritis, pain, asthma, psoriasis, and allergies; the pain perception is fibromyalgia; the mood disorders are depression, including major depression, single episode depression, recurrent depression, child abuse induced depression, and postpartum depression; the neurodegenerative diseases are selected from Alzheimer's disease, Parkinson's disease, and Huntington's disease; and the eating disorders are selected from anorexia nervosa and bulimia nervosa.

15. A method according to claim 13, wherein the inflammatory disorders are selected from rheumatoid arthritis, osteoarthritis, pain, asthma, psoriasis, and allergies; the pain perception is fibromyalgia; the mood disorders are depression, including major depression, single episode depression, recurrent depression, child abuse induced depression, and postpartum depression; the neurodegenerative diseases are selected from Alzheimer's disease, Parkinson's disease, and Huntington's disease; and the eating disorders are selected from anorexia nervosa and bulimia nervosa.

16. A process for preparing a compound of the formula I,

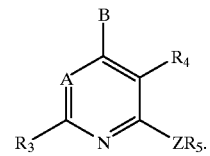

or a pharmaceutically acceptable salt thereof, wherein

A is —$CR_7$;

B is —$NHCHR_1R_2$, or —$OCHR_1R_2$;

Z is O;

$R_1$ is $C_1$–$C_6$ alkyl which may optionally contain one double or triple bond and which may optionally be substituted with one or two substituents selected independently from hydroxy or $C_1$–$C_4$ alkoxy;

$R_2$ is $C_1$–$C_{12}$ alkyl which may optionally contain one double or triple bond and which may optionally be substituted with from one to three $C_1$–$C_6$ alkoxy;

$R_3$ is methyl;

$R_4$ is hydrogen, methoxy, amino, nitro, —$NH(C_1$–$C_4$ alkyl), —$N(CH_3)_2$, —$COO(C_1$–$C_4$ alkyl), or $C_1$–$C_4$ one hydroxy, $C_1$–$C_3$ alkoxy or chloro; $R_5$ is phenyl or pyridyl and $R_5$ is substituted with two or three substituents independently selected from fluoro, chloro, $C_1$–$C_6$ alkyl, and $C_1$–$C_4$ alkoxy, and wherein one of said substituents can further be selected from hydroxy, iodo, bromo, formyl, and trifluoromethyl, and wherein said $C_1$–$C_6$ alkyl $R_5$ group may optionally be substituted with one fluoro or hydroxy; and $R_7$ is hydrogen or methyl;

or a pharmaceutically acceptable salt of such compound; comprising reacting a compound of the formula

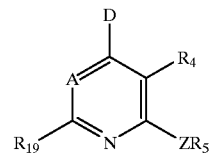

wherein $R_{19}$ is methyl or ethyl, D is chloro and A, Z, $R_4$ and $R_5$ are defined as above, with a compound of the formula BH, wherein B is defined as above, in the presence of a base; and then optionally converting the compound of formula I formed in such reaction into a pharmaceutically acceptable salt.

* * * * *

UNITED STATES PATENT AND TRADEMARK OFFICE
CERTIFICATE OF CORRECTION

PATENT NO. : 5,962,479
DATED : October 5, 1999
INVENTOR(S) : Yuhpyng L. Chen

It is certified that error appears in the above-identified patent and that said Letters Patent is hereby corrected as shown below:

Column 54,
Lines 36-37, delete "alkyl one optionally substituted by hydroxy;" and insert -- alkyl optionally substituted by one hydroxy, $C_1$-$C_3$ alkoxy, or chloro; -- in place thereof.

Column 58,
Lines 29-30, delete "$C_1$-$C_4$ alkyl one hydroxy, $C_1$-$C_3$ alkoxy, or chloro;" and insert -- $C_1$-$C_4$ alkyl optionally substituted by one hydroxy, $C_1$-$C_3$ alkoxy, or chloro; -- in place thereof.

Signed and Sealed this

Fifteenth Day of November, 2005

JON W. DUDAS
*Director of the United States Patent and Trademark Office*